US008920806B2

(12) United States Patent
De Kretser et al.

(10) Patent No.: US 8,920,806 B2
(45) Date of Patent: Dec. 30, 2014

(54) METHOD OF MODULATING INFLAMMATORY RESPONSE BY DOWNREGULATION OF ACTIVIN

(75) Inventors: David Morritz De Kretser, Surrey Hills (AU); David James Phillips, Hughesdale (AU); Kristian Lee Jones, Hawthorn East (AU); Robyn O'Hehir, Melbourne (AU); Shane Patella, Oakleigh (AU)

(73) Assignee: Paranta Biosciences Limited, Richmond, Victoria (AU)

( * ) Notice: Subject to any disclaimer, the term of this patent is extended or adjusted under 35 U.S.C. 154(b) by 1299 days.

(21) Appl. No.: 10/575,049

(22) PCT Filed: Oct. 6, 2004

(86) PCT No.: PCT/AU2004/001359
§ 371 (c)(1),
(2), (4) Date: Nov. 13, 2006

(87) PCT Pub. No.: WO2005/032578
PCT Pub. Date: Apr. 14, 2005

(65) Prior Publication Data
US 2007/0248609 A1    Oct. 25, 2007

(30) Foreign Application Priority Data

Oct. 6, 2003   (AU) ................................ 2003905461
Apr. 16, 2004  (AU) ................................ 2004902056
Aug. 24, 2004  (AU) ................................ 2004904834

(51) Int. Cl.
*A61K 39/00*   (2006.01)
*C07K 16/26*   (2006.01)
*A61K 38/17*   (2006.01)

(52) U.S. Cl.
CPC ............ *A61K 38/1709* (2013.01); *C07K 16/26* (2013.01)
USPC ......................... 424/184.1; 514/1.8; 514/21.2

(58) Field of Classification Search
None
See application file for complete search history.

(56) References Cited

U.S. PATENT DOCUMENTS

| | | | |
|---|---|---|---|
| 5,041,538 A | | 8/1991 | Ling et al. |
| 5,216,126 A | | 6/1993 | Cox et al. |
| 5,470,826 A | | 11/1995 | De Kretser et al. |
| 5,545,616 A | * | 8/1996 | Woodruff ........................... 514/8 |
| 2002/0028762 A1 | | 3/2002 | Kojima |
| 2002/0192216 A1 | * | 12/2002 | Lamb et al. ................. 424/145.1 |
| 2003/0162715 A1 | * | 8/2003 | Duan et al. ...................... 514/12 |
| 2005/0266519 A1 | | 12/2005 | Mellor |
| 2007/0135336 A1 | | 6/2007 | De Kretser et al. |
| 2007/0248609 A1 | | 10/2007 | De Kretser et al. |
| 2011/0129845 A1 | * | 6/2011 | O'Hehir ........................ 435/6.17 |

FOREIGN PATENT DOCUMENTS

| | | | |
|---|---|---|---|
| AU | 199923590 | | 10/1999 |
| JP | 2003 238440 | | 8/2003 |
| WO | WO 88/05789 | | 8/1988 |
| WO | WO 89/11862 | | 12/1989 |
| WO | WO 8911862 | * | 12/1989 |
| WO | WO 92/08480 A1 | | 5/1992 |
| WO | WO 94/09809 A1 | | 5/1994 |
| WO | WO 96/11259 | | 4/1996 |
| WO | WO 99/10364 | | 3/1999 |
| WO | WO 99/10364 A1 | | 4/1999 |
| WO | WO 01/05998 A1 | | 1/2001 |
| WO | WO 03/006057 | * | 1/2003 |
| WO | WO 03/066081 | | 8/2003 |
| WO | WO2013/059876 | * | 2/2013 |

OTHER PUBLICATIONS van Eyll et al. Shh-dependent differentiation of intestinal tissue from embryonic pancreas by activin A . Journal of Cell Science 117, 2077-2086 (2004).*
Russel et al. Activin A regulates growth and acute phase proteins in the human liver cell line, HepG2. Molecular and Cellular Endocrinology vol. 148, Issues 1-2, Feb. 25, 1999, pp. 129-136.*
Cho et al. Regulation of activin A expression in mast cells and asthma: its effect on the proliferation of human airway smooth muscle cells. J Immunol. Apr. 15, 2003;170(8):4045-52.*
Sidis et al. Follistatin-related protein and follistatin differentially neutralize endogenous vs. exogenous activin. Endocrinology, 143:1613-24, 2002.*
Liem et al. Regulation of the neural patterning activity of sonic hedgehog by secreted BMP inhibitors expressed by notochord and somites. Development. Nov. 2000;127(22):4855-66.*
Klein et al. Plasma follistatin concentrations increase following lipopolysaccharide administration in sheep. Clinical and Experimental Pharmacology and Physiology. (1996), 23(8), 754-755.*
Alban et al. Identification and characterization of the activin A gene in human mast cells and its possible role in airway remodeling. Journal of Allergy and Clinical Immunology, (Jan. 2002) vol. 109, No. 1 Supplement, pp. S31. 58th Annual Meeting of the American Academy of Allergy, Asthma and Immunology.*
Cho et al. Regulation of Activin A Expression in Mast Cells and Asthma:Its Effect on the Proliferation of Human Airway Smooth Muscle Cells. J Immunol. Apr. 15, 2003;170(8):4045-52.*

(Continued)

*Primary Examiner* — Maher Haddad
(74) *Attorney, Agent, or Firm* — Foley & Lardner LLP

(57) ABSTRACT

The present invention relates generally to a method of modulating an inflammatory response in a mammal and to agents useful for same. More particularly, the present invention relates to a method of modulating an inflammatory response in a mammal by modulating the functional activity of activin and thereby modulating the pro-inflammatory mediator cascade. The method of the present invention is useful, inter alia, in the treatment and/or prophylaxis of conditions characterized by an aberrant, unwanted or otherwise inappropriate inflammatory response including, inter alia, sepsis and inflammation of the airway. The present invention is further directed to methods for identifying and/or designing agents capable of modulating activin mediated regulation of the inflammatory response.

7 Claims, 24 Drawing Sheets

(56) References Cited

OTHER PUBLICATIONS

Patella et al. Follistatin attenuates early liver fibrosis: effects on hepatic stellate cell activation and hepatocyte apoptosis. Am J Physiol Gastrointest Liver Physiol. Jan. 2006;290(1):G137-44.*
de Winter J.P. et al., "Follistatins Neutralize Activin Bioactivity by Inhibition of Activin Binding to its Type II Receptors", *Molecular and Cellular Endocrinology* 116(1):105-114 (1996).
Yu E.W. et al., "Suppression of IL-6 Biological Activities by Activin A and Implications for Inflammatory Arthropathesis", *Clinical and Experimental Immunology* 112:126-132 (1998).
Jones K.L. et al., "Activin A Release into the Circulations is an Early Event in Systemic Inflammation and Precedes the Release of Follistatin", *Endocrinology* 141(5):1905-1908 (2000).
Phillips D.J. et al., "Evidence for Activin A and Follistatin Involvement in the Systemic Inflammatory Response", *Molecular and Cellular Endocrinology* 180(1-2):155-162 (2001).
Gribi R. et al., "Expression of Activin A in Inflammatory Arthropathies", *Molecular and Cellular Endocrinology* 180(1-2):163-167 (2001).
Murata T. et al., "Anti-activin A Antibody (IgY) Specifically Neutralizes Various Activin A Activities", *P.S.E.B.M* 211(1): 100-107 (1996).
Hubner G. et al., "Activin A: A Novel Player and Inflammatory Marker in Inflammatory Bowel Disease?", *Laboratory Investigation* 77(4): 311-318 (1997).
De Kretser D. M. et al., "Activin A and follistatin: their role in the acute phase reaction and inflammation", *Journal of Endocrinology* 161: 195-198 (1991).
Alexander C., et al., "Bacterial lipopolysaccharides and innate immunity", *Journal of Endotoxin Research* 7(3): 167-202 (2001).
Benayoun L. et al., "Airway Structural Alterations Selectively Associated with Severe Asthma", *American Journal of Respiratory and Critical Care Medicine* 167: 1360-1368 (2003).
Bernard D. J., "Both SMAD2 and SMAD3 Mediate Activin-Stimulated Expression of the Follicle-Stimulating Hormone β Subunit in Mouse Gonadotrope Cells", *Molecular Endocrinolgoy* 18(3): 606-623 (2004).
Billestrup N. et al., "Inhibition of somatotroph growth and growth hormone biosynthesis by activin in vitro", *Mol Endocrinol* 4(2): 356-362 (1990).
Brown C. W. et al., "Insertion of *Inhbb* into the *Inhba* locus rescues the *Inhba*-null phenotype and reveals new activin functions", *Nature Genetics* 25: 453-457 (2000).
Bunin B. A., "The combinatorial synthesis and chemical and biological evaluation of a 1,4-benzodiazepine library", *Proc. Natl. Acad. Sci. USA* 91: 4708-4712 (1994).
Corrigan A. Z. et al., "Evidence for an autocrine role of activin B within rat anterior pituitary cultures", *Endocrinology* 128(3): 1682-1684 (1991).
Coyle A. J., "Mice Lacking the IFN-γ Receptor Have an Imparied Ability to Resolve a Lung Eosinophilic Inflammatory Response Associated with a Prolonged Capacity of T Cells to Exhibit a Th2 Cytokine Profile", *The Journal of Immunology* 156: 2680-2685 (1996).
De Bleser P. J. et al., "Localization and Cellular Sources of Activins in Normal and Fibrotic Rat Liver", *Hepatology* 26: 905-912 (1997).
Demura R. et al., "Human Plasma Free Activin and Inhibin Levels During The Menstrual Cycle", *Journal of Clinical Endocrinology and Metabolism* 76(4): 1080-1082 (1993).
Demura R. et al., "Competitive Protein Binding Assay for Activin A/EDF Using Follistatin Determination of Activin Levels in Human Plasma", *Biochemical and Biophysical Research Communications* 185(3): 1148-1155 (1992).
De Witt S. H. et al., "Diversomers": An approach to nonpeptide, nonoligomeric chemical diversity, *Proc. Natl. Acad. Sci. USA* 90: 6909-6913 (1993).
Eramaa M. et al., "Activin A/Erythroid Differentiation Factor Is Induced during Human Monocyte Activation", *J. Exp. Med.* 176: 1449-1452 (1992).

Fodor S. P. A. et al., "Light-Directed, Spatially Addressable Parallel Chemical Synthesis", *Science* 251: 767-773 (1991).
Gilfillan C. P. et al., "Development and validation of a radioimmunoassay for follistatin in human serum", *Clinical Endocrinology* 41: 453-481 (1994).
Hardy C. L. et al., "Characterization of a Mosue Model of Allergy to a Major Occupational Latex Glove Allergen Hev b 5", *Am J Respir Crit Care Med* 167: 1393-1399 (2003).
Harrison C. A. et al., "An Activin Mutant with Disrupted ALK4 Binding Blocks Signaling via Type II Receptors", *The Journal of Biological Chemistry* 279(27): 28036-28044 (2004).
Hashimoto O. et al., "A Novel Role of Follistatin, an Activin-binding Protein, in the Inhibition of Activin Action in Rat Pituitary Cells", *The Journal of Biological Chemistry* 272(21): 13835-13842 (1997).
Hubner G. et al., "Serum Growth Factors and Proinflammatory Cytokines Are potent Inducers of Activin Expression in Cultured Fibroblasts and Keratinocytes", *Experimental Cell Research* 228: 106-113 (1996).
Hubner G. et al., "Strong Induction of Activin Expression after Injury Suggests an Important Role of Activin in Wound Repair", *Developmental Biology* 173: 490-498 (1996).
Jones R. L. et al., "Inhibin and activin subunits are differentially expressed in endometrial cells and leukocytes during the menstrual cycle, in early pregnancy and in women using progestin-only contraception", *Molecular Human Reproduction* 6(12): 1107-1117 (2000).
Keelan J. A. et al., "Activin A Exerts both Pro- and Anti-inflammatory Effects on Human term Gestational Tissues", *Placenta* 21: 38-43 (2000).
Khoury R. H. et al., "Serum Follistatin Levels in Women: Evidence against an Endocrine Function of Ovarian Follistatin", *Journal of Clinical Endocrinolgoy and Metabolism* 80(4): 1361-1368 (1995).
Kitaoka M. et al., "Activin-A: A Modulator of Multiple Types of Anterior Pituitary Cells Masafumi Kitaoka, Itaru Kojima and Etsuro Ogata", *Biochemical and Biophysical Research Communications* 157(1): 48-55 (1988).
Knight P. G. et al., "Development and application of a two-site enzyme immunoassay for the determination of 'total' activin-A concentrations inserum and follicular fluid", *Journal of Endocrinology* 148: 267-279 (1996).
Kobayashi T. et al., "Expression of Inhibin $\beta_A$, $\beta_B$, and Follistatin mRNAs in the Carbon Tetrachloride Induced Rat Liver Regeneration Model", *Biol. Pharm. Bull.* 23(6): 755-757 (2000).
Kohler et al., "Continuous cultures of fused cells secreting antibody of predefined specificity", *Nature* 256: 495-497 (1975).
Kumar R. K. et al., "Role of interleukin-13 in eosinophil accumulation and airway remodeling in a mouse model of chronic asthma", *Clin Exp Allergy* 32: 1104-1111 (2002).
Lee C. G. et al., "Interleukin-13 Induces Tissue Fibrosis by Selectively Stimulating and Activating Transforming Growth Factor $\beta_1$", *J. Exp. Med.* 194(6): 809-821 (2001).
Li X. et al., "Increased Vascularity of the Bronchial Mucosa in Mild Asthma", *Am J Respir Crit Care Med* 156: 229-233 (1997).
Loria P. et al., "Influence of age and sex on serum concentrations of total dimeric activin A", European *Journal of Endocrinology* 139: 487-492 (1998).
Maeshima K. et al., "Crucial Role of Activin A in Tubulogenesis of Endothelial Cells Induced by Vascular Endothelial Growth Factor", *Endocrinology* 145(8): 3739-3745 (2004).
Manthey C. L. et al., "Endotoxin-Induced Early Gene Expression in CSH?HeJ ($Lps^d$) Macrophages[1]", *The Journal of Immunology* 153: 2653-2663 (1994).
Matsuse T. et la., "Expression of Immunoreactive and Bioactive Activin A Protein in Adult Murine Lung after Bleomycin Treatment", *Am. J. Respir. Cell Mol. Biol.* 13: 17-24 (1995).
Matsuse T. et al., "Expression of Immunoreactive Activin A Protein in Remodeling Lesions Associated with Interstitial Pulmonary Fibrosis", *American Journal of Pathology* 148(3): 707-713 (1996).
Matzuk M. M. et al., "Functional analysis of activins during mammalian development", *Nature* 374: 354-356 (1995).
McFarlane J. R. et al., "Measurement of activin in biological fluids by radioimmunoassay, utilizing dissociating agents to remove the interference of follistatin", *Eur J. Endocrinol.* 134: 481-499 (1996).

(56) References Cited

OTHER PUBLICATIONS

Meunier et al., "Gonadal and extragonadal expression of inhibin α, βA, and βB subunits in various tissues preducts diverse functions", *PNAS 85*: 247-251 (1988).
Michael U. et al., "Rat Follistatin: Goonadal and Extragonadal Expression and Evidence for Alternative Splicing", *Biochemical and Biophysical Research Communications 173*(1): 401-407 (1990).
Michel U. et al., "Expresson of follistatin messenger ribonucleic acid in Sertoli cell-enriched cultures: regulation by epidermal growth factor and protein kinase C-depenent pathway but not by follicle-stimulating hormone and protein kinase A-dependent pathway" *Acta Endocrinologica 129*: 525-531 (1993).
Michel U. et al., "Productionof Follistatin in Porcine Endothelial Cells: Differential Regulation by Bacterial Compounds and the Synthetic Glucocorticoid RU 28362", *Endocrinology 137*(11): 4925-4934 (1996).
Michel U. et al., "Serum concentrations of activin and follistatin are elevated and run in parallel in patients with septicemia", *European Journal of Endocrinology 148*: 559-564 (2003).
Mohan A. et al., "Effect of cytokines and growth factors on the secretion of inhibin A, activin A and follistatin by term placental villous trophoblasts in culture", *European Journal of Endocrinology 145*: 505-511 (2001).
Nakamura T. et al., "Activin-Binding Protein from Rat Ovary Is Follistatin", *Science 247*: 836-838 (1990).
Nakamura T. et al., "Isolation and Characterization of Native Activin B", The Journal of Biological *Chemistry 267*(23): 16385-16389 (1992).
O'Connor A. E. et al., "Serum activin A and follistatin concentrations during human pregnancy: a cross-sectional and longitudinal study", *Human Reproduction 14*(3): 827-832 (1999).
Orsida B. E., "Vascularity in asthmatic airways: relation to inhaled steroid dose", *Thorax 54*: 289-295 (1999).
Petraglia F. et al., "Activin A and activin B measured in maternal serum, cord blood serum and amniotic fluid during human pregnancy", *Endocrine Journal 1*: 323-327 (1993).
Phillips D. J. et al., "Follistatin has a biphasic response but follicle-stimulating hormone is unchanged during an inflammatory episode in growing lambs", *Journal of Endocrinology 156*: 77-82 (1998).
Phillips D. J. et al., "Follistatin: A Multifunctional Regulatory Protein", *Frontiers in Neuroendocrinology 19*: 287-322 (1998).
Phillips D. J., "New developments in the biology of inhibins, activins and follistatins", *Trends in Endocrinology & Metabolism 12*(3): 94-96 (2001).
Phillips D. J., "Regulation of activin's access to the cell: why is Mother Nature such a control freak?", *BioEssays 22*: 689-696 (2000).
Poulaki V. et al., "Activin A in the Regulation of Corneal Neovascularization and Vascular Endothelial Growth Factor Expression", *American Journal of Pathology 164*(4): 1293-1302 (2004).
Robinson G. W. et al., "Inhibins and activins regulate mammary epithelial cell differentiation through mesenchmal-epithelial interactions", *Development 124*: 2701-2708 (1997).
Rosendahl A. et al., "Activation of the TGF-β/Activin-Smad2 Pathway during Allerigc Airway Inflammation", *Am J. Respir. Cell Mol. Biol.* 25:60-68 (2001).
Russell C. E. et a., "Activin A regulates growth and acute phase proteins in the human liver cell line, HepG2", *Molecular and Cellular Endocrinology 148*: 129-136 (1999).
Sakai R. et al., "The Measurement of Activin/EDF in Mouse Serum: Evidence for Extragonadal Production", *Biochemical and Biophysical Research Communications 188*(2): 921-926 (1992).
Sakamoto Y. et al., "Determination of free follistatin levels in sera of n ormal subjects and patients with various diseases", *European Journal of Endocrinology 135*: 345-351 (1996).
Schneider O. et al., "Comparative analysis of follistatin-, activin beta A- and activin beta B-mRNA steady-state levels in diverse porcine tissues by multiplex S1 nuclease analysis", European Journal of Endocrinology 142: 537-544 (2000).
Shao et al., "Regulation of Production of Activin A in Human Marrow Stromal Cells and Monocytes", *Exp Hematol 20*: 1235-1242 (1992).

Shao Li-En et al., "Contrasting Effects of Inflammatory Cytokines and Glucocorticoids on the Production of Activin A in Human Marrow Stromal Cells and Their Implications", *Cytokine 10*(3): 227-235 (1998).
Stein C. A. et al., "Oligodeoxynucleotides as Inhibitors of Gene Expression: A Review", *Cancer Research 48*: 2659-2668 (1988).
Takabe K. et al., "Adenovirus-Mediated Overexpression of Follistatin Enlarges Intact Liver of Adult Rats", *Hepatology 38*: 1107-1115 (2003).
Thomsen G. et al., "Activins Are Expressed Early in Xenopus Embryogenesis and Can Induce Axial Mesoderm and Anterior Structures", *Cell 63*: 485-493 (1990).
Tilbrook A. J. et al., "The testis is not the major source of circulating follistatin in the ram", *Journal of Endocrinology 149*: 55-63 (1996).
Tsuchida K. et al., "Activin isoforms signal through type I receptor serine/threonine kinase ALK7", *Molecular and Cellular Endocrinology 220*: 59-65 (2004).
Ulevitch R. J. et al., "Recognition of Gram-negative bacteria and endotoxin by the innate immune system", *Current Opinion in Immunology 11*: 19-22 (1999).
Vale W. et al., "Purification and characterization of an FSH releasing protein from porcine ovarian follicular fluid", *Nature 321*: 776-779 (1986).
Vale W. et al., "The Inhibin/Activin Family of Hormones and Growth Factors", Chapter 26, *Handbook of Experimental Physiology 95*: 211-248 (1990).
van der Krol A. R. et al., "Modulation of Eukaryotic Gene Expression by Complementary RNA or DNA Sequences", *BioTechniques 6*(10): 958-976 (1988).
Van Baalen B. et al., "Traumatic brain injury: classification of initial severity and determination of functional outcome", *Disability and Rehabilitation 25*(1): 9-18 (2003).
Van Dijk W., "Interleukin-6-Type Cytokine-induced Changes in Acute Phase Protein Glycosylation", *Annals New York Academy of Sciences 762*: 319-330 (1995).
Vassalli A. et al., "Activin/inhibin βB subunit gene disruption leads to defects in eyelid development and female reproduction", *Genes & Development 8*: 414-427 (1994).
Vihko K. et al., "Activin B: detection by an immunoenzymometric assay in human serum during ovarian stimulation and late pregnancy", *Human Reproduction 13*(4): 841-846 (1998).
Vihko K. K. et al., "Activin B in patients with granulose cell tumors: serum levels in comparison to inhibin", *Acta Obstet Gynecol Scand 82*: 570-574 (2003).
Wakatsuki M. et al., "Immunoradiometric Assay for Follistatin: serum Immunoreactive Follistatin Levels in Normal Adults and Pregnant Women", *Journal of Clinical Endocrinology and Metabolism 81*(2): 630-634 (1996).
Wilson J. W. et al., "The measurement of reticular basement membrane and submucosal collagen in the asthmatic airway", *Clinical and Experimental Allergy 27*: 363-371 (1997).
Woodruff T. K. et al., "Activin A and follistatin are dynamically regulated during human pregnancy", *Journal of Endocrinology 152*: 167-174 (1997).
Xu J. et al., "Inhibin Antagonizes Inhibition of Liver Cell Growth by Activin by a Dominant-negative Mechanism", *The Journal of Biological Chemistry 270*(11): 6308-6313 (1995).
Yu J. et al., "Induced expression of the new cytokine, activin A, in human monocytes: inhibition by glucocorticoids and retinoic acid", *Immunology 88*: 368-374 (1996).
Arthur M., "Fibrogenesis: Metalloproteinases and their inhibitors in liver fibrosis," *American Journal of Physiology—Gastrointestinal and Liver Physiology*, 279: G245-G249 (2000).
Bartholin, et al., "FLRG, an Activin-Binding Protein, is a New Target of TGF-beta Transcription Activation Through SMAD Proteins," *Oncogene*, 20(39):5409-19 (2001).
Date M., et al., "Differential expression of transforming growth factor β and its receptors in hepatocytes and nonparenchymal cells of rat liver after CCl4 administration," *Journal of Hepatalogy*, 28: 572-581 (1998).
Date M., et al., "Differential regulation of activin A for hepatocyte growth and fibronectin synthesis in rat liver injury," *J Hepatol.*, 32(2):251-260 (2000).

(56) References Cited

OTHER PUBLICATIONS

Dooley S., et al., "Expression of Smads during in vitro transdifferentiation of hepatic stellate cells to myofibroblasts," *Biochem. Biaphys. Res. Comm.*, 283:554-562 (2001).

Engelse M., et al., "Human activin A is expressed in the atherosclerotic lesion and promotes the contractile phenotype of smooth muscle cells," *Circulation Research*, 85: 931-939 (1999).

Friedman S., et al., "Hepatic lipocytes: the principal collagen-producing cells of normal rat liver," *Proc. Natl. Acad. Sci. USA*, 82(24):8681-8685 (1985).

Friedman S., et al., "Modulatin of transforming growth factor preceptors of rat lipocytes during the hepatic wound healing response. Enhanced binding and reduced gene expression accompany cellular activation in culture and in vivo," *J. Biol. Chem.*, 269(4):10551-10558 (1994).

Friedman S., et al., "Molecular mechanisms of hepatic fibrosis and principles of therapy," *J. Gastroenterol.*, 32(3): 424-430 (1997).

George, et al., "In vivo inhibition of rat stellate cell activation by soluble transforming growth factor p type II receptor: A potential new therapy for hepatic fibrosis," *Proc. Natl. Acad. Sci. USA*, 96(22):12719-24 (1999).

Harada K., et al., "Serum immunoreactive activin A levels in normal subjects and patients with various diseases," *J. Clin. Endocrinal. Metab.*, 81(6):2125-2130 (1996).

Huang X., et al., "Expression changes of activin A in the development of hepatic fibrosis," *World Journal af Gastroenterology*, 7:37-41 (2001) (abstract).

Huang X., et al., *Zhonghua Ganzangbing Zazhi* (*Chinese J. of Hepatology*), 10(2):85-89 (2002) (abstract).

Hubner G., et al., "Activin A—a novel player and inflammatory marker in inflammatory bowel disease," *Lab. Invest.*, 77:311-318 (1977).

Hully J.R., et al., "Induction of apoptosis in the murine liver with recombinant human activin A," *Hepatology*, 20:854-862 (1994).

Inoue S., et al., "Expression of follistatin, an activin-binding protein, in vascular smooth muscle cells and arteriosclerotic lesions," *Arteriosclerosis and Thrombosis*, 13(12):1859-1864 (1993).

Kay M., et al., "Liver regeneration: prospects for therapy based on new technologies," *Molecular Medicine Today*, 108-115 (1997).

Kogawa K., et al., "Immunohistochemical localization of follistatin in rat tissues," *Endocrinol. Japan*, 38(4): 383-391 (1991).

Kogure K., et al., "A single intraportal administration offollistatin accelerates liver regeneration in partially hepatectomized rats," *Gastrenterology*, 108(4):1136-1142 (1995).

Kogure K., et al., "Immediate onset ofDNA synthesis in remnant rat liver after 90% hepatectomy by an administration of follistatin," *J. Hepatol.*, 29(6):977-984 (1998).

Kogure K., et al., "Intravenous administration of follistatin: delivery to the liver and effect on the liver regeneration after partial hepatectomy," *Hepatology*, 24(2):361-366 (1996).

Kogure K., et al., "The role of activin and transforming growth factor β in the regulation of organ mass in the rat liver," *Hepatology*, 31(4):916-921 (2000).

Kojima I., et al., "Role of the activin-foJlistatin system in the morphogenesis and regeneration of the renal tubules," *Molecular and Cellular Endocrinology*, 180:179-182 (2001).

Kotsuji T., et al., "Effects of activin A on the growth of neurofibroma-derived cells from a patient with neurofibromatosis type I," *Dermatology*, 201:277 (2000).

Kozaki K., et al., "Activin/follistatin and atherosclerosis—A review," *J. Atherosclerosis and Thrombosis*, 5:36-40 (1998).

Kozian D.,et al., "The activin-binding protein follistatin regulates autocrine endothelial cell acrtivity and induces angiogenesis," *Lab. Invest.*, 76(2): 267-276 (1997).

Laping N., "Therapeutic uses of smad protein inhibitors: selective inhibition of specific TGF-β activities," *Drugs*, 2: 907-914 (1999).

Lee D., et al., "The hepatitis B virus encoded oncoprotein pX amplifies TGF-β family signaling through direct interaction with Smad4: potential mechanism of hepatitis B virus-induced liver fibrosis," *Genes & Dev.*, 15(4): 455-466 (2001).

Maeshima A., et al., "Hepatocyte growth factor induces branching tubulogenesis in MDCK cells by modulating the activin-follistatin system," *Kidney International*, 58:1511-1522 (2000).

Matsuda Y.,et al., "Preventative and therapeutic effects in rats of hepatocyte growth factor infusion on liver fibrosis/cirrhosis," *Hepatology*, 26(1):81-89 (1977).

Michalopoulos G., et al., "Liver Regeneration," *Science*, 276:60-66 (1996).

Molloy C., et al., "Novel cardiovascular actions of the activins," 1. *Endocrin..* 161:179-185 (1995).

Munz B., et al. "A novel role of activin in inflammation and repair," 1. *Endocrin.*, 161-187-193,(1995).

Nakamura T., et al., "Inhibition of transforming growth factor p prevents progression of liver fibrosis and enhances hepatocyte regeneration in dimethylnitrosamine-treated rats," *Hepatology*, 32(2):247-255 (2000).

Nieto N., et al., "CYP2EI-mediated oxidative stress induces collagen type I expression in rat hepatic stellate cells," *Hepatology*, 30(4):987-996 (1999).

Ogawa K., et al., "Activin A stimulates type IV collagenase (matrix metalloproteinase-2) production in mouse peritoneal macrophages," *J. Immunol.*, 165:2997-3003 (2000).

Ohga E., et al., "Activin receptors are expressed on human lung fibroblast and activin A facilitates fibroblast-mediated collagen gel contraction," *Life Sciences*, 66:1603-1613 (2000).

Ohga E., et al., "Effects of Activin A on Proliferation and Differentiation of Human Lung Fibroblasts," *Biochemical and Biophysical Research Communications*, 228(2):391-396 (1996).

Okuno M., et al., "Prevention of Rat Hepatic Fibrosis by the Protease Inhibitor, Camostat Mesilate, via Reduced Generation of Active TGF-p," *Gastroenterology*, 120(7):1784-1800 (2001).

Patella S., et al. "Characterization of serum activin-A and follistatin and their relation to virological and histological detenninants in chronic viral hepatitis." *J. Hepatol.*, 34(4):576-583, (2001).

Phillips DJ., et al., "A sensitive and specific in vitro bioassay for activin using a mouse plasmacytoma cell line, MPC-II," *J. Endocrin.*, 162(1):111-116 (1999).

Pianko S., et al., "Hepatocyte apoptosis is increased in chronic HCV infection and alcohol use," Abstract from Annual Meeting of American Gastroenterological Association and American Association for the Study of Liver Diseases, May 11-14, 1997.

Pinzani M., et al., "Transfonning growth factor-p I regulates platelet-derived growth factor receptor p subunit in human liver fat-storing cells," *Hepatology*, 21(1):232-239 (1995).

Pirisi M., et al. "Evaluation of circulating activin-A as a serum marker of hepatocellular carcinoma," *Cancer Detect & Prev.*, 24(2):150-155 (2000).

Qi Z., et al., "Blockade of type β transfonning growth factor signaling prevents liver fibrosis and dysfunction in the rat," *PNAS*, 96:2345-2349 (1999).

Ramm G., et al., "Vitamin A-poor lipocytes: a novel desmin-negative lipocyte subpopulation, which can be activated to myofibroblasts," *Am. J. Physiol.*, 269(4 Pt I):G532-41 (1995).

Ritvos O., et al., "Activin disrupts epithelial branching morphogenesis in developing glandular organs of the mouse," *Mech. & Devel.*, 50:229-245 (1995).

Rosenbaum J., et al., "Fibroblast growth factor 2 and transforming growth factor β1 interactions in human livermyofibroblasts," *Gastroenterology*, 109(6):1986-1996 (1995).

Sakurai T, et al., "Activin A stimulates mitogenesis in Swiss 3T3 fibroblasts without activation of mitogen-activated protien kinases," *J. Bioi. Chern.*, 269: 14118-22 (1994).

Schwall R., et al., "Activin induces cell death in hepatocytes in vivo and in vitro," *Hepatology*, 18(2):347-356 (1993).

Urbanek et al., "Thirty-seven candidate genes for polycystic ovary syndrome: Strongest evidence for linkage is with follistatin," *PNAS USA*, 96:8573-78 (1999).

Phillips & Woodruff, "Inhibin: actions and signaling," *Growth factors*, 22:13-18 (2004).

De Kretser, et al., "Inhibins, activins and follistatin in reproduction," *Human reproduction update*, 8:529-41 (2002).

(56) References Cited

OTHER PUBLICATIONS

Matzuk, et al., "Development of cancer cachexia-like syndrome and adrenal tumors in inhibin-deficient mice," *PNAS USA*, 91:8817-21 (1994).
Matzuk, et al., "Multiple defects and perinatal death in mice deficient in follistatin," *Nature*, 374:360-63 (1995).
Bilezikjian, et al., "Pituitary actions of ligands of the TGF-β family: activins and inhibins," *Reproduction*, 132:207-15 (2006).
Shimonaka, et al., "Follistatin binds to both activin and inhibin through the common beta-subunit," *Endocrinology*, 128:3313-15 (1991).
Aleman-Muench & Soldevila, "When versatility matters: activins/inhibins as key regulators of immunity," *Immunology and cell biology*, In press (2011).
Licona-Limón, et al., "Activins and inhibins: novel regulators of thymocyte development," *Biochemical and biophysical research communications*, 381:229-35 (2009).
Broxmeyer, et al., "Selective and indirect modulation of human multipotential and erythroid hematopoietic progenitor cell proliferation by recombinant human activin and inhibin," *PNAS USA*, 85:9052-56 (1988).
Jones, et al., "Activin A is a critical component of the inflammatory response, and its binding protein, follistatin, reduces mortality in endotoxemia," *PNAS USA*,104:16239-44 (2007).
Patella, et al., "Follistatin attenuates early liver fibrosis: effects on hepatic stellate cell activation and hepatocyte apoptosis," *American journal of physiology: Gastrointestinal and liver physiology*, 290:G137-44 (2006).
Boehm,"Design principle of adaptive immune systems," *Nature Reviews. Immunology*, 11:307-17 (2011).
Benabdallah, et al., "Overexpression of follistatin in human myoblasts increases their proliferation and differentiation, and improves the graft success in SCID mice," *Cell transplantation*, 18:709-18 (2009).
Kanamoto, et al., "Beneficial effects of follistatin in hepatic ischemia-reperfusion injuries in rats," *Digestive diseases and sciences*, 56:1075-81 (2011).
Larson, et al., "Scarless fetal wound healing: a basic science review," *Plastic and reconstructive surgery*, 126:1172-80 (2010).
Mukherjee, et al., "FSTL3 deletion reveals roles for TGF-62 family ligands in bludose and fat homeostasis in adults," *PNAS USA*, 104(4):1348-53 (2007).
Sidis, et al., "Biological activity of Follistatin Isoforms and FSTL-3 is Dependent on Differential Cell Surface Binding and Specificity for Activin, Myostatin and BMPs," *Endocrinology*, 147(7)3586-97 (2006).
Sugiyama M., et al., "Expression of activin A is increased in cirrhotic and fibrotic rat livers," *Gastroenterology*, 114(3):550-558 (1998).
Takabe K., et al., "Recombinant adenovirus vector encoding follistatin: A potential tool to stimulate liver regeneration," AASLD Abstract No. 351 from *Hepatology*, Oct. 1999.
Thomas T., et al., "Inhibins, activins, and follistatins: Expression of mRNAs and cellular localization in tissues from men with benign prostatic hyperplasia," *The Prostate*, 34(1): 34-43 (1998).
"Ulcerative Colitis," From National Institute of Diabetes and Digestive and Kidney Diseases (NIH Publication No. 95-1597, Apr. 1992).
Wang E., et al., "Indentification of naturally occurring follistatin complexes in human biological fluids," *Bioi. Reprod.*, 60:8-13 (1999).
Website: "Facts about pulmonary fibrosis and interstitial lung disease," American Lung Association website, originally www.lullgusa. orgldiseases/pulmfibrosis on Nov. 7, 2000—enclosed version downloaded from http://209.208.158.222/diseases/pulmfibrosis.html on Jul. 1, 2004.

Website: Nadel, M., "Crohn's Disease (Granulomatous Ileitis and Colitis)", Internet site: http://155.37.5.42/TMGEN/67062160.htm on Dec. 6, 2000. (downloaded on Jun. 25, 2004).
Yasuda H., et al., "Activin A: An autocrine inhibitor of initiation ofDNA synthesis in rat hepatocytes," *J. Clin. Invest.*, 92(3):491-1496 (1993).
Yasuda H., et al., "Antifibrogenic effect of a deletion variant of hepatocyte growth factor on liver fibrosis in rats," *Hepatology*, 24(3): 636-642 (1996).
Yuen M.F., et al., "Transforming growth factor-β1, activin and follistatin in patients with hepatocellular carcinoma and patients with alcoholic cirrhosis," *Scand. J. Gastroenterol.*, 37(2):233-238 (2002).
Zhu J, et al., "Rapamycin inhibits stellate cell proliferatin in vitro and limits fibrogenesis in an in vivo model of liver fibrosis," *Gastroenterology*, 117(5):1198-1204 (1999).
Azuma T, et al., *Hepatology*, 34(4-2):395A (2001) (abstract).
Murata T , et al., Anti-activin A antibody (IgY) specifically neutralizes various activin A activities,: *Proc. Soc. for Exp. Biol. and Med.*, 211(1):100-07 (1996).
De Kretser DM, et al., "Activin A and Follistatin: Their role in the acute phase reaction and inflammation," *J. of Endocrinology*, 161(1):195-98 (1999).
Van Eyll J, et al., "Shh-dependent differentiation of intestinal tissue from embryonic pancreas by Activin A," *J. of Cell Science*, 117(10):2077-86, 2004.
Hedger M, et al., "The regulation and functions of activin and follistatin in inflammation and immunity," *Vitam Horm*, 85:255-97 (2011).
Lin S-Y, et al., "Regulation of Ovarian Function by the TGF-β Superfamily and Follistatin," *Reproduction*, 126: 133-48 (2003).
Amthor H, et al., "Follistatin Regulates Gone Morphogenetic Protein-7 (BMP-&) Activity to Stimulate Embryonic Muscle Growth," *Developmental Biology*, 243:115-27 (2002).
Zhang Y-Q et al., "Regulation of the Expression of Follistatin in Rat Hepatocytes," *Biochimica et Biophysica Acta*, 1354:204-10 (1997).
Gamer L, et al., "GDFI 1 is a Negative Regulator of Chondrogenesis and Mygenesis in the Developing Chick Limb," *Developmental Biology*, 229:407-20 (2001).
Patel K, et al., "Molecules in Focus: Follistatin," *The International J. of Biochemistry and Cell Biology*, 30:1087-93 (1998).
Iemura S-I, et al., "Direct Binding of Follistatin to a Complex of Bone-Morphogenetic Protein and its Receptor Inhibits Ventral and Epidermal Cell Fates in Early Xenopus Embryo," *PNAS USA*, 95:9337-42 (1998).
Wankell M, et al., "Impaired Wound Healing in Transgenic Mice Overexpressing the Activin Antagonist Follistatin in the Epidermis," *The EMBO Journal*, 20:5361-72 (2001).
U.S. Appl. No. 10/755,545 First Office Action, pp. 1-15, 2007.
U.S. Appl. No. 10/755,545 Second Office Action, pp. 1-17, 2008.
U.S. Appl. No. 10/755,545 Third Office Action, pp. 1-26, 2008.
U.S. Appl. No. 12/399,610 First Office Action, pp. 1-14, 2010.
Alcolado R., et al., "Pathogenesis of live fibrosis," *Clin. Sci. (Cotch)*, 92(2):103-112 (1997).
Greco B., et al., "Atherosclerotic Ischemic Renal Disease," *Amer. J. Kidney Diseases*, 9(2)167-187 (1997).
Ichikawa T., et al., "Transforming growth factor β and activin tonically inhibit DNA synthesis in the rat liver," *Hepatology*, 34(5):918-925 (2001).
Ishak K., et al., "Histological grading and staging of chronic hepatitis," *J Hepatol.*, 22(6):696-699 (1995)
Issa R., et al., "Apoptosis of hepatic stellate cells: involvement in resolution of biliary fibrosis and regulation by soluble growth factors," *Gut*, 48(4) 548-557 (2001).
Reimann T., et al., "Transfonning growth factor-βI induces activation of Ras, Raf-I, MEK and MAPK in rat hepatic stellate cells," *FEBS Lett.*, 403(1):57-60 (1997).

\* cited by examiner (A)

(B)

(C)

(D)

(E)

.5FS represents the level of TNFα or IL-6 in mice 30 minutes after administration of follistatin alone (i.e. no LPS)

.5FS represents the level of TNFα or IL-6 in mice 30 minutes after administration of follistatin alone (i.e. no LPS)

METHOD OF MODULATING INFLAMMATORY RESPONSE BY DOWNREGULATION OF ACTIVIN

FIELD OF THE INVENTION

The present invention relates generally to a method of modulating an inflammatory response in a mammal and to agents useful for same. More particularly, the present invention relates to a method of modulating an inflammatory response in a mammal by modulating the functional activity of activin and thereby modulating the pro-inflammatory mediator cascade. The method of the present invention is useful, inter alia, in the treatment and/or prophylaxis of conditions characterised by an aberrant, unwanted or otherwise inappropriate inflammatory response including, inter alia, sepsis and inflammation of the airway. The present invention is further directed to methods for identifying and/or designing agents capable of modulating activin mediated regulation of the inflammatory response.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Mammals are required to defend themselves against a multitude of pathogens including viruses, bacteria, fungi and parasites, as well as non-pathogenic insults such as tumours and toxic, or otherwise harmful, agents. In response, effector mechanisms have evolved which are capable of mounting a defense against such antigens. These mechanisms are mediated by soluble molecules and/or by cells.

In the context of these effector mechanisms, inflammation is a complex multifaceted process in response to disease or injury which is regulated by the release of a series of cytokines (Alexander et al, 2001, *J Endotoxin Res* 7:167-202). These cytokines are classified in general terms as pro- or anti-inflammatory cytokines and the critical balance between release and activity of cytokines with opposing actions regulates the inflammatory response to prevent it from becoming overt or understated.

If the inflammatory response continues unchecked and is overt then the host may suffer associated tissue damage and in severe cases this may present as septic shock and multi-organ failure can occur (Ulevitch et al., 1999, *Curr Opin Immunol* 11:19-22). Conversely, a poor or understated inflammatory response may mean uncontrolled infection resulting in chronic illness and host damage. Regulation of the inflammatory response is important at both the systemic level and the local level.

The discovery of the detailed processes of inflammation has revealed a close relationship between inflammation and the immune response. There are five basic indicators of inflammation, these being redness (rubor), swelling (tumour), heat (calor), pain (dolor) and deranged function (functio laesa). These indicators occur due to extravasation of plasma and infiltration of leukocytes into the site of inflammation. Consistent with these indicators, the main characteristics of the inflammatory response are therefore:

(i) vasodilation—widening of the blood vessels to increase the blood flow to the infected area;

(ii) increased vascular permeability—this allows diffusible components to enter the site;

(iii) cellular infiltration—this being the directed movement of inflammatory cells through the walls of blood vessels into the site of injury;

(iv) changes in biosynthetic, metabolic and catabolic profiles of many organs; and (v) activation of cells of the immune system as well as of complex enzymatic systems of blood plasma.

The degree to which these characteristics occur is generally proportional to the severity of the injury and/or the extent of infection.

The inflammatory response can be broadly categorised into several phases. The earliest, gross event of an inflammatory response is temporary vasoconstriction, i.e. narrowing of blood vessels caused by contraction of smooth muscle in the vessel walls, which can be seen as blanching (whitening) of the skin. This is followed by several phases that occur over minutes, hours and days later, as follows:

(i) The acute vascular response follows within seconds of a tissue insult and lasts for some minutes. It is characterised by vasodilation and increased capillary permeability due to alterations in the vascular endothelium, leading to increased blood flow (hyperaemia) that causes redness (erythema) and the entry of fluid into the tissues (oedema).

(ii) If there has been sufficient damage to the tissues, or if infection has occurred, the acute cellular response takes place over the next few hours. The hallmark of this phase is the appearance of granulocytes, particularly neutrophils, in the tissue. These cells first attach themselves to the endothelial cells within the blood vessels (margination) and then cross into the surrounding tissue (diapedesis). If the vessel is damaged, fibrinogen and fibronectin are deposited at the site of injury, platelets aggregate and become activated and clot formation occurs.

(iii) If damage is sufficiently severe, a chronic cellular response may follow over the next few days. A characteristic of this phase of inflammation is the appearance of a mononuclear cell infiltrate composed of macrophages and lymphocytes. The macrophages are involved in microbial killing, in clearing up cellular and tissue debris, and are also thought to play a significant role in remodelling tissue.

(iv) Over the next few weeks, resolution may occur wherein normal tissue architecture is restored. Blood clots are removed by fibrinolysis. If it is not possible to return the tissue to its original form, scarring may occur from in-filling with fibroblasts, collagen, and new endothelial cells. Generally, by this time any infection will have been overcome, although this is not always the case and may result in further immunological responses, such as granuloma formation.

Inflammation is often considered in terms of acute inflammation that includes all the events of the acute vascular and acute cellular response (1 and 2 above), and chronic inflammation that includes the events during the chronic cellular response and resolution or scarring (3 and 4).

It should be understood, however, that in addition to the occurrence of inflammatory responses in a localised fashion in tissue which is damaged, infected or subject to an autoimmune response inflammatory responses may also occur systemically, such as in the case with sepsis.

Accordingly, in light of the wide-ranging impact of inflammatory responses, there is an ongoing need to elucidate the complex mechanisms by which they function. By identifying these mechanisms there is thereby provided scope for developing means of appropriately modulating inflammatory responses.

Inhibin, activin, and follistatin are three families of polypeptides originally isolated and characterized from ovarian follicular fluid based on their modulation of follicle stimulating hormone release from pituitary cell culture. In addition to their effects on follicle stimulating hormone synthesis and secretion, inhibin and activin have other biological functions. By contrast, the physiological significance of follistatin was obscure, until it was discovered that follistatin is a binding protein to activin.

Activins, composed of two β-subunits, $β_A$, $β_B$, $β_C$ and/or $β_E$ are members of the transforming growth factor (TGF)-β superfamily [Vale et al., 1990, Handbook of Experimental Physiology, Vol. 95, Eds. Sporn & Roberts, Springer-Verlag, Berlin pp 211-248]. Multimeric protein forms of activin include the homodimeric forms (Activin A-$β_Aβ_A$, Activin B-$β_Bβ_B$, Activin C-$β_Cβ_C$, and Activin E-$β_Eβ_E$) and the heterodimeric forms (for example, Activin AB-$β_Aβ_B$, Activin AC-$β_Aβ_C$, or Activin AE-$β_Aβ_E$). The activins are multifunctional proteins. For example, Activin A, although originally identified as a regulator of follicle stimulating hormone release, is now known to exhibit the pleiotropic range of functional activities which are characteristic of most cytokines. Activins, like their related proteins, inhibins (which consist of a dimer of a structurally related but dissimilar α subunit and an activin β subunit) can bind to activin type II receptors. However, only activins are able to recruit type I receptors to form an active complex, triggering intracellular Smad signalling pathways and thereby influencing cellular function at the transcriptional level. At present, activin A, AB and B have been shown to demonstrate typical receptor-mediated agonist activity. Activin B has been reported to display less biological activity than activin A [Nakamura et al., *Journal of Biological Chemistry*, 267, 16385-16389, 1992]. This may be associated with variation in the availability of specific type I receptors, differentially recruited by activin A and B [Tsuchida et al., 2004 *Molecular and Cellular Endocrinology* 220, 50-65].

Follistatin functions as a biological regulator of activin. In fact, it was originally identified by its ability to suppress the secretion of follicle stimulating hormone, subsequently shown to be due to its property as an activin binding protein. Follistatin is a monomeric protein which binds to activin with high affinity and is believed to thereafter lead to lysosomal degradation of the complexed activin. Follistatin comprises a number of post-translational and glycosylation variants. However, the two major isoforms are the full length follistatin 315, which is believed to be the predominant circulating isoform, and the 288 isoform, which has a strong affinity for heparin sulphate proteoglycans and is largely a cell membrane-associated isoform (Phillips and de Kretser, 1998, *Frontiers in Neuroendocrinology* 19:287-322).

Activin affects the growth and differentiation of many cell types, stimulates the secretion of follicle-stimulating hormone from the pituitary gland and inhibits growth hormone, prolactin, and adrenocorticotropin release [Billestrup et al., *Molecular Endocrinology* 1990 4:356-362; Kitaoka et al., *Biochemical and Biophysical Research Communications* 1988 157:48-54; Vale et al., *Nature* 1986, 321:776-779]. Activin A was first characterized for its ability to stimulate follicle stimulating hormone (FSH) from the pituitary, a capacity shared by activin B [Nakamura et al., 1992, supra; Van Dijk et al., 1995, *Annals of the New York Academy of Science* 762, 319-330]. However, activin A is now known to have many more properties besides this initial function for which it was first isolated. Both activin A and B participate in foetal development, with their respective mouse knockouts [Vassali et al., 1994, *Genes and Development*, 8:414-427] presenting distinct phenotypic anomalies. Knockouts of activin A exhibit neonatal lethal phenotypic defects [Vassali et al., 1994, supra; Matzuk et al., 1995, *Nature* 374: 354-356] but substitution of the $β_A$ gene with $β_B$ provides partial rescue of this phenotype [Brown et al., 2000, *Nature Genetics*, 25:453-457], suggesting some overlap in the activities of activin A and B. In contrast to these observations there is evidence that activin B may have specific roles in processes such as embryonic mesoderm induction [Thomsen et al., 1990, *Cell* 63:485-493] and mammary gland development [Robinson et al., 1997, *Development* 124:2701-2708]. Of particular interest is that activin B is presumed to be the activin of relevance in intrapituitary regulation of FSH, as shown by neutralization studies [Corrigan et al., 1991, *Endocrinology* 128:1682-1684]. Additionally, distinct differences in expression patterns of activin A and B are evident during tissue repair [Hübner et al., 1996, *Developmental Biology* 173:490-498] and in association with models of liver fibrosis [De Bleser et al., 1997, *Hepatology*, 26:905-912]. Such evidence suggests that activin A and B play different roles in a range of biological and pathological processes.

Follistatin specifically binds several members of the TGF-β superfamily, but has by far the highest affinity of binding to activin. As a result, circulating follistatin 315 neutralizes activin activity by preventing the interaction of the cytokine with its type II receptors [de Winter et al., *Molecular and Cellular Endocrinology* 1996 116:105-114] and, furthermore, cell surface-bound follistatin 288 facilitates the lysosomal degradation of activin [Hashimoto et al., *Journal of Biological Chemistry* 1997 272:13835-13842]. Both follistatin and activin mRNAs show a broad tissue distribution [Meunier et al., *PNAS* 1988 85:247-251; Michel et al., *Biochemical and Biophysical Research Communications* 1990 173:401-407; Schneider et al., *European Journal of Endocrinology* 2000 142:537-544]. Follistatin and activin are detectable in serum [Demura et al., *Journal of Clinical Endocrinology and Metabolism* 1993 76:1080-1082; Demura et al., *Biochemical and Biophysical Research Communications* 1992 185:1148-1154; Gilfillan et al., *Clinical Endocrinology* 1994 41:453-461; Khoury et al., *Journal of Clinical Endocrinology and Metabolism* 1995 80:1361-1368; Knight et al., *Journal of Endocrinology* 1996 148:267-279; McFarlane et al., *European Journal of Endocrinology* 1996 134:481-489; Sakai et al., *Biochemical and Biophysical Research Communications* 1992 188:921-926; Sakamoto et al., *European Journal of Endocrinology* 1996 135:345-351; Tilbrook et al., *Journal of Endocrinology* 1996 149:55-63; Wakatsuki et al., *Journal of Clinical Endocrinology and Metabolism* 1996 81:630-634], and their concentrations in serum increase with age [Wakatsuki et al. 1996, supra; Loria et al., *European Journal of Endocrinology* 1998 139:487-492]. At present, however, the precise sources of follistatin and activin in serum are unknown. Current data suggest that tissue-specific balances of follistatin and activin govern the growth and differentiation of responsive cell types in an autocrine/paracrine manner [Michel et al., *Acta Endocrinologica* 1993 129:525-531; Phillips, *Trends in Endocrinology and Metabolism* 2001 12:94-96].

An emerging role for activin and follistatin in the body's innate immune response has been documented. For instance, activin and follistatin are secreted by various cell types in response to inflammatory compounds in vitro [Hübner et al., *Experimental Cell Research* 1996 228:106-113; Jones et al., *Endocrinology* 2000 141:1905-1908; Keelan et al., *Placenta* 2000 21:38-43; Michel et al., *Endocrinology* 1996 137:4925-4934; Phillips et al., *Journal of Endocrinology* 1998 156:77-82; Yu et al., *Immunology* 1996 88:368-374; Erämaa et al., Journal of Experimental Medicine 1992 176:1449-1452; Shao et al., *Cytokine* 1998 10:227-235; Mohan et al., *European Journal of Endocrinology* 2001 145:505-511]. Moreover, in some examples of inflammatory processes such as wound healing, inflammatory bowel disease and rheumatoid arthritis, increased activin and/or follistatin expression has been noted [Hübner et al., *Laboratory Investigation* 1997 77:311-318; Hübner et al., 1996, supra; Yu et al., *Clinical and Experimental Immunology* 1998 112:126-132]. However, since these very early and preliminary findings, the role of activin and follistatin in the context of inflammation, per se, has not been further elucidated, either in the context of their precise activities or in the context of the scope of the inflammatory conditions in which they function. In light of the extreme diversity in terms of the nature and extent of inflammatory responses which can occur, and the extremely pleiotropic activities of cytokines such as the various forms of activin, it is not surprising that the preliminary findings of the mid to late 1990's have not progressed to more substantial theories. In particular, activin A, activin B and follistatin are expressed by a wide variety of cell types and most organs in the body in response to a wide range of stimuli. Accordingly, their role in the context of inflammation cannot be predicted and is therefore far from clear.

In work leading up to the present invention it has been surprisingly determined that activins A functions as a crucial component of the cytokine cascade which regulates the inflammatory response. Specifically, activin A initiates the release, in vivo, of the pro-inflammatory cytokines and can, in fact, modulate the levels of pro-inflammatory cytokines which are released subsequently to an appropriate stimulus. Accordingly, although it has previously been observed that activin A levels are modulated during the onset and progress of an inflammatory response, until the advent of the present invention there had been no progress made in elucidating the precise role of this molecule in the context of inflammation.

It has still further been surprisingly determined that activin B levels are even more dramatically modulated in the context of an inflammatory response than are activin A levels. This is particularly surprising in light of what has been known to date in relation to the distinct roles of activins A and B. Still further, whereas immunoassays directed to the measurement of activin A have been available for use for some time, analysis of activin B has been inhibited by the absence of a specific immunoassay for this particular activin species. A very limited data set is available which suggests that circulating activin B levels alter during pregnancy or with ovarian function [Petraglia et al., 1993, *Endocrine Journal* 1:323-327; Woodruff et al., 1997, *Journal of Endocrinology* 152:167-174; Vihko et al., 1998, *Human Reproduction* 13:841-846; Vihko et al., 2003, *Acta Obstetricia et Gynecologica Scandinavica,* 80:570-574]. Kobayashi et al. (2000) [*Biol. Pharm. Bull.* 23(6):755-757] demonstrated that an increase in activin-$\beta_B$ mRNA is associated with liver regeneration and the development of fibrosis, although the authors do not postulate whether this is linked with changes to levels of activin AB, Activin B or inhibin. A study by Rosendahl et al. 2001 [*Am J Respir Cell Mol Biol* 25:60-68] examined a mouse model of allergen-induced airway challenge in the lung and focussed on examining associated changes in expression and distribution of TGF-β superfamily and TGF-β/activin receptors. This group reported that induced airway allergens produced only a very modest elevation of activin $\beta_B$ mRNA expression over control levels. Histological examinations did not provide any information on mature activin dimer protein synthesis or distribution (either activin A or B) nor was there any evidence provided that the modest increase in activin-$\beta_B$ mRNA levels was not, in fact, linked to changes in inhibin levels. Accordingly, the determination that activin B levels are in fact dramatically increased during inflammation relative to activin A levels is extremely unexpected in light of the very limited information which was available about the functioning of both the activin A and activin B molecules.

The findings of the present invention have now facilitated the development of methodology directed to modulating the inflammatory response by regulating the levels of functionally active activin A and activin B and, therefore, pro-inflammatory cytokine release. Accordingly, there are now provided both methods for the therapeutic or prophylactic treatment of conditions characterised by an unwanted or inappropriate inflammatory response and means for screening for regulators of pro-inflammatory cytokine release such as activin A and activin B mimetics, agonists or antagonists.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each nucleotide sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention is directed to a method of modulating the inflammatory response in a mammal, said method comprising modulating the functional activity of activin wherein upregulating activin fragments, derivatives, mutants or variants thereof to a functionally effective level in said mammal induces, maintains or upregulates the pro-inflammatory mediator cascade and downregulating activin to a functionally ineffective level in said mammal inhibits or retards the pro-inflammatory mediator cascade.

Another aspect of the present invention is directed to a method of modulating the inflamatory response in a mammal, said method comprising modulating the functional activity of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the pro-inflammatory mediator cascade.

In still another aspect the present invention is directed to a method of modulating a local inflammatory response in a mammal, said method comprising modulating the functional activity of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the local pro-inflammatory mediator cascade.

In yet another aspect the present invention is directed to a method of modulating a systemic inflammatory response in a mammal, said method comprising modulating the functional activity of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the systemic pro-inflammatory mediator cascade.

In still yet another aspect the present invention is directed to a method of modulating the inflammatory response in a mammal, said method comprising modulating the functional activity of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the pro-inflammatory cytokine cascade.

In yet still another aspect the present invention is directed to a method of modulating a local inflammatory response in a mammal, said method comprising modulating the functional activity of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the local pro-inflammatory cytokine cascade.

In a further aspect the present invention is directed to a method of modulating a systemic inflammatory response in a mammal, said method comprising modulating the functional activity of activin, which activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the systemic pro-inflammatory cytokine cascade.

In another further aspect the present invention is directed to a method of down-regulating the inflammatory response in a mammal, said method comprising administering to said mammal an effective amount of an agent for a time and under conditions sufficient to induce a functionally ineffective level of activin, which activin is activin A or an activin molecule comprising a $\beta_B$ subunit, fragments, derivatives, mutants or variants thereof, in said mammal.

In yet another further aspect there is provided a method of up-regulating the inflammatory response in a mammal, said method comprising administering to said mammal an effective amount of an agent for a time and under conditions sufficient to induce a functionally effective level of activin, which activin is activin A or an activin molecule comprising a $\beta_B$ subunit, fragments, derivatives, mutants or variants thereof, in said mammal.

Still another further aspect of the present invention contemplates a method of therapeutically and/or prophylactically treating a condition, or a predisposition to the development of a condition, characterised by an aberrant, unwanted or otherwise inappropriate inflammatory response in a mammal, said method comprising modulating the level of activin in said mammal where up-regulating activin fragments, derivatives, mutants or variants thereof to a functionally effective level up-regulates the pro-inflammatory mediator cascade and down-regulating activin to a functionally ineffective level inhibits or retards the pro-inflammatory mediator cascade.

Yet still another further aspect of the present invention contemplates a method of therapeutically and/or prophylactically treating a condition or a predisposition to the development of a condition, characterised by an aberrant, unwanted or otherwise inappropriate inflammatory response in a mammal, said method comprising modulating the level of activin, wherein activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level inhibits or retards the pro-inflammatory cytokine cascade.

In still yet another further aspect there is provided a method of therapeutically and/or prophylactically treating a condition, or a predisposition to the development of a condition, characterised by an unwanted acute inflammatory response in a mammal, said method comprising down-regulating the level activin, which activin is activin A or an activin molecule comprising a $\beta_B$ subunit, fragments, derivatives, mutants or variants thereof, wherein downregulating said activin to a functionally ineffective level inhibits or retards the pro-inflammatory cytokine cascade.

In another aspect there is provided a method of therapeutically and/or prophylactically treating a condition, or a predisposition to the development of a condition, characterised by an inadequate inflammatory response in a mammal, said method comprising modulating the level of activin, which activin is activin A or an activin molecule comprising a $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally effective level up-regulates the pro-inflammatory cytokine cascade.

Still another aspect of the present invention relates to the use of an agent capable of modulating the functionally effective level of activin, fragments, derivatives, mutants or variants thereof, in the manufacture of a medicament for the therapeutic and/or prophylactic treatment of a condition, or a predisposition to the development of a condition, characterised by an aberrant, unwanted or otherwise inappropriate inflammatory response in a mammal wherein up-regulating activin to a functionally effective level up-regulates the pro-inflammatory mediator cascade and down-regulating activin to a functionally ineffective level inhibits or retards the pro-inflammatory mediator cascade.

Yet another aspect of the present invention relates to the use of an agent capable of modulating the functionally effective level of activin, which activin is activin A or an activin molecule comprising a $\beta_B$ subunit, fragments, derivatives, mutants or variants thereof, in the manufacture of a medicament for the therapeutic and/or prophylactic treatment of a condition, or a predisposition to the development of a condition, characterised by an aberrant, unwanted or otherwise inappropriate inflammatory response in a mammal wherein up-regulating said activin to a functionally effective level in said mammal induces, maintains or upregulates the pro-inflammatory mediator cascade and downregulating said activin to a functionally ineffective level inhibits or retards the pro-inflammatory cytokine cascade.

In yet another further aspect, the present invention contemplates a pharmaceutical composition comprising the modulatory agent as hereinbefore defined together with one or more pharmaceutically acceptable carriers and/or diluents.

DETAILED DESCRIPTION OF THE INVENTION

Figure 1A:
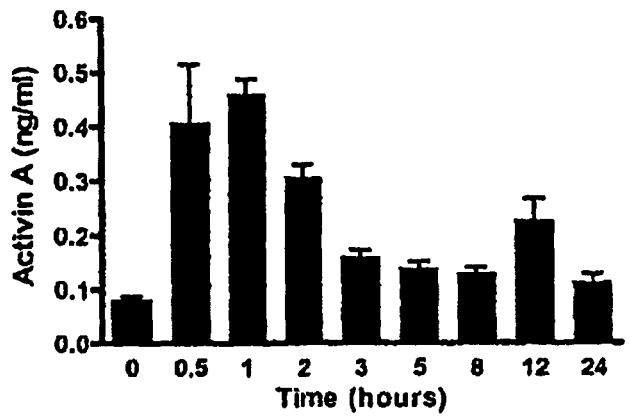
FIG. 1A is a graphical representation of activin A release following an inflammatory challenge, in the form of lipopolysaccharide (LPS), in mice.

The present invention is predicated, in part, on the surprising determination that the role of activins A and B in the inflammatory response occur in the context of these molecules being modulators of pro-inflammatory cytokine release. Specifically, activin A has been found to initiate the onset of the pro-inflammatory cytokine cascade. Similarly, but still more surprisingly, activin molecules comprising the $\beta_B$ subunit have now also been found to regulate the very early stages of the inflammatory response, despite otherwise exhibiting significant functional distinctiveness to activin A. Most surprisingly, however, this molecule exhibits significantly higher levels of expression than activin A at this time. Accordingly, these findings have now facilitated the rational design of means for modulating the inflammatory response and, in particular, for therapeutically or prophylactically treating conditions which are characterised by an inappropriate inflammatory response. Further, there is facilitated the identification and/or design of agents which specifically interact with or mimic activin A or an activin molecule comprising a $\beta_B$ subunit to modulate its functionality and thereby the onset or progression of an inflammatory response.

Accordingly, one aspect of the present invention is directed to a method of modulating the inflammatory response in a mammal, said method comprising modulating the functional activity of activin, fragments, derivatives, mutants or variants thereof, wherein upregulating activin to a functionally effective level in said mammal induces, maintains or upregulates the pro-inflammatory mediator cascade and downregulating activin to a functionally ineffective level in said mammal inhibits or retards the pro-inflammatory mediator cascade.

More particularly, the present invention is directed to a method of modulating the inflammatory response in a mammal, said method comprising modulating the functional activity of activin, which activin is activin A or an activin molecule comprising the $\beta_B$ subunit, fragments, derivatives, mutants or variants thereof, wherein upregulating said activin to a functionally effective level in said mammal induces, maintains or upregulates the pro-inflammatory mediator cascade and downregulating said activin to a functionally ineffective level in said mammal inhibits or retards the pro-inflammatory mediator cascade.

Without limiting the present invention to any one theory or mode of action, the inflammatory response is a complex response characterised by a series of physiological and/or immunological events which are induced to occur by the release of a cytokine cascade in response to any one of a variety of stimuli including, but not limited to, tissue injury, infection, an immune response (such as to a pathogen or an innocuous agent—as occurs with allergies), or disease (such as tumour formation or an autoimmune response).

The physiological events which characterise inflammation include:
(i) vasodilation
(ii) increased vascular permeability
(iii) cellular infiltration
(iv) changes to the biosynthetic, metabolic and catabolic profiles of affected organs
(v) activation of the cells of the immune system.

It should be understood that reference to an "inflammatory response" is a reference to any one or more of the physiological and/or immunological events or phases that are induced to occur in the context of inflammation and, specifically, in response to the signals generated by the cytokine cascade which directs the inflammatory response. For example IL-1, TNFα and IL-6 are well known for their functions as pro-inflammatory mediators. It should also be understood that an inflammatory response within the context of the present invention essentially includes a reference to a partial response, such as a response which has only just commenced, or to any specific phase or event of a response (such as the phases and events detailed in points (i)-(v), above, or any other effect related to inflammation including, but not limited to, the production of acute phase proteins—including complement components, fever and a systemic immune response). Further, it should also be understood that depending on any given set of specific circumstances, the end point of an inflammatory response may vary. For example, in some situations there may only occur an acute vascular response. To the extent that "acute" inflammation occurs, this is generally understood to include the events of both an acute vascular response and an acute cellular response. Some inflammatory responses will resolve at the acute stage while others may progress to become chronic cellular responses.

Without limiting the present invention to any one theory or mode of action, in certain circumstances the acute process, characterized by neutrophil infiltration and oedema, gives way to a predominance of mononuclear phagocytes and lymphocytes. This is thought to occur to some degree with the normal healing process but becomes exaggerated and chronic when there is ineffective elimination of foreign materials as in certain infections (e.g. tuberculosis) or following introduction of foreign bodies (e.g. asbestos) or deposition of crystals (e.g. urate crystals). Chronic inflammation is often associated with fusion of mononuclear cells to form multinucleated gigant cells, which eventually become a granuloma. Chronic inflammation is also seen under conditions of delayed hypersensitivity. The subject inflammatory response may be systemic or localised. Examples of systemic inflammatory responses include those which fall within the scope of systemic inflammatory response syndrome such as septic shock, toxic shock or septicaemia.

Examples of localised inflammatory responses include those which occur in the context of airway inflammation (for example, asthma, interstitial lung disease, cystic fibrosis, lung transplantation, bronchiolitis obliterans, emphysema, obstructive pulmonary disease, asbestosis, obstructive sleep apnoea, hypoxia or pulmonary hypertension), rheumatoid arthritis, multiple sclerosis, encephalitis, severe acute respiratory distress syndrome, inflammatory bowel disease, pancreatitis, atherosclerosis, meningitis, appendicitis, angiogenesis, psoriasis, neural protection, renal tubular necrosis, traumatic brain injury, allergic responses and wound healing (for example, pursuant to surgery, burns or other tissue injury). It should be understood, however, that some localised inflammatory responses can become systemic, for example as can occur when the onset of septic shock occurs as a complication of severe burns or abdominal wounds. In another example, septicaemia can result from the transition of a more localised bacterial infection to a circulatory infection.

Accordingly, in one preferred embodiment the present invention is directed to a method of modulating a local inflammatory response in a mammal, said method comprising modulating the functional activity of activin, which activin is activin A or an activin molecule comprising the $\beta_B$ subunit, fragments, derivatives, mutants or variants thereof, wherein upregulating said activin to a functionally effective level in said mammal induces, maintains or upregulates the local pro-inflammatory mediator cascade and down-regulating said activin to a functionally ineffective level in said mammal inhibits or retards the local pro-inflammatory mediator cascade.

More preferably, said local inflammatory response is acute.

In another preferred embodiment the present invention is directed to a method of modulating a systemic inflammatory response in a mammal, said method comprising modulating the functional activity of activin, which activin is activin A or an activin molecule comprising the $\beta_B$ subunit, fragments, derivatives, mutants or variants thereof, wherein upregulating said activin to a functionally effective level in said mammal induces, maintains or up-regulates the systemic pro-inflammatory mediator cascade and down-regulating said activin to a functionally ineffective level in said mammal inhibits or retards the systemic pro-inflammatory mediator cascade.

More preferably, said systemic inflammatory response is acute.

In accordance with these preferred aspects of the present invention, said acute inflammatory response is preferably down-regulated and occurs in the context of, or is otherwise associated with, septic shock, septicaemia, airway inflammation, appendicitis, meningitis, hepatic response to toxins or viruses, angiogenesis, psoriasis, neural protection, atherosclerosis, renal tubular necrosis, encephalitis, wound healing or traumatic injury such as occurs with injury, surgery and burns (e.g. traumatic brain injury).

Preferably, said airway inflammation occurs in the context of asthma, interstitial lung disease, cystic fibrosis, lung transplantation, SARS, bronchiolitis obliterans, emphysema, obstructive pulmonary disease, asbestosis, obstructive sleep apnoea, hypoxia or pulmonary hypertension.

Preferably, said acute systemic inflammatory response occurs in the context of systemic inflammatory response syndrome and even more particularly sepsis, septicaemia, toxic shock, septic shock, tissue trauma, meningitis or appendicitis.

In another preferred embodiment, said inflammatory disease is chronic.

Still more preferably, said chronic inflammatory response occurs in the context of, or is otherwise associated with multiple sclerosis, inflammatory bowel disease, rheumatoid arthritis, asthma, psoriasis or wound healing.

It should be understood that some conditions and diseases, such as inflammatory bowl disease or wound healing can be associated with both acute and chronic phases and are therefore detailed herein in both contexts.

Reference to "activin A" should be understood as a reference to all forms of activin A. Activin A is a dimeric protein which comprises two activin $\beta_A$ subunits. It should also be understood to include reference to a dimer comprising any isoforms which may arise from alternative splicing of activin $\beta_A$ mRNA or mutant or polymorphic forms of activin $\beta_A$. Reference to "activin A" should be understood to include reference to all forms of these molecules including all precursor, proprotein or intermediate forms thereof. Reference to activin A should also be understood to extend to any activin A protein, whether existing as a dimer, multimer or fusion protein.

Reference to "an activin molecule comprising a $\beta_B$ subunit" should be understood as a reference to a monomeric or multimeric molecule, preferably a dimer, which comprises at least one activin $\beta_B$ subunit. Reference to "activin $\beta_B$" should be understood as a reference to all forms of activin $\beta_B$. "Activin $\beta_B$ subunit" is also interchangeably referred to as "activin $\beta_B$". It should be understood to include reference to any isoforms which may arise from alternative splicing of activin $\beta_B$ mRNA or mutant or polymorphic forms of activin $\beta_B$. Reference to "activin $\beta_B$" is not intended to be limiting and should be read as including reference to all forms of activin $\beta_B$ including any protein encoded by the activin $\beta_B$ subunit gene, any subunit polypeptide such as precursor forms which may be generated, and any $\beta_B$ protein, whether existing as a monomer, multimer or fusion protein. Multimeric protein forms of activin $\beta_B$ include for example the homodimeric activin B ($\beta_B$-$\beta_B$) or the heterodimeric activin AB ($\beta_A$-$\beta_B$), activin BC ($\beta_B$-$\beta_C$), activin BD ($\beta_B$-$\beta_D$) or activin BE ($\beta_B$-$\beta_E$) proteins. Preferably, said activin molecule is activin B.

Reference to "modulating" should be understood as a reference to up-regulating or down-regulating the subject inflammatory response. Reference to "down-regulating" an inflammatory response should therefore be understood as a reference to preventing, reducing (eg. slowing) or otherwise inhibiting one or more aspects of an inflammatory response while reference to "up-regulating" should be understood to have the converse meaning. In the context of the present invention, modulation of the inflammatory response is achieved via up-regulation or down-regulation of the pro-inflammatory cytokine cascade. Although the preferred method is to down-regulate the inflammatory response in the context of conditions characterised by an unwanted inflammatory response, such as airway inflammation, sepsis, septicaemia, meningitis, rheumatoid arthritis or tissue trauma, the present invention nevertheless extends to up-regulating the inflammatory response in circumstances where it is desired that an inflammatory response occur. This may occur, for example, in situations where an inflammatory response is required to provide adjuvant-like activity. This may be particularly useful in the context of anti-tumour therapy. In still another example, the upregulation of host defense mechanisms may be desired.

Without limiting the present invention to any one theory or mode of action, inflammation is a complex biological process which involves the interaction, in a cascade fashion, of numerous soluble mediators. Briefly, the cascade of cytokines and other inflammatory mediators which act to induce an inflammatory response can be schematically depicted as follows:

| | |
|---|---|
| I. | Inflammatory Cytokines (TNF-α, IL-1, IL-6) |
| II. | Soluble Receptors (sTNFRs, sIL-6R, sFas) |

↓

| | |
|---|---|
| I. | Monocyte and T-Lymphocyte Activation |
| II. | Monocyte-Edothelial Cell Adhesive Interaction |

↓

-continued

| I. | Induction and Release of Adhesion Molecules (sICAM-1, sVCAM-1) |
| II. | Induction of Chemokine Synthesis (MCP-1, MIP-1α, RANTES) |
| III. | Overexpression of Hemopoietic Cytokines (M-CSF, GM-CSF) |

| I. | Further Cytokine Production |
| II. | Free Radical Generation |
| III. | III. NO Overproduction |
| IV. | Apoptosis |

| I. | Tissue Destruction |
| II. | Tissue Remodelling |
| III. | Loss of Functions |

Accordingly, reference to "pro-inflammatory mediator cascade" or "pro-inflammatory cytokine cascade" should be understood as a reference to the sequential interaction of soluble molecules which characterise the onset and progression of an inflammatory response. In particular, the onset of an inflammatory mediator cascade is characterised by the sequential up-regulation of expression of TNF-α, IL-1 and IL-6. However, the entire inflammatory process is nevertheless characterised by sequential changes in the levels of various cytokines (the term "cytokines" should be broadly understood to include reference to the interleukins, chemokines, monokines, colony stimulating factors and other such protein hormones). Despite prior observations that levels of activin are modulated in mammals experiencing an inflammatory response, the precise role of activin in this context was not understood. To this end, the pro-inflammatory cytokines are still generally understood to be constituted by TNF-α, IL-1 and IL-6. Still further, and without limiting the present invention in any way, TNF-α is secreted in response to various pro-inflammatory stimuli and exerts a wide variety of effects. At low concentrations, it acts as a paracrine and autocrine molecule, upregulating vascular adhesion molecules, activating neutrophils, and stimulating monocytes to secrete Interleukin 1, 6 and more TNF-α. At higher concentrations, TNF-α enters the serum and becomes an endocrine hormone. Here, it acts as a pyrogen, stimulates further cytokine liberation from mononuclear cells, activates the coagulation system, and suppresses bone marrow stem cell maturation. At even higher concentrations, INF-α has many deleterious effects, including hypotension (probably through induction of nitric oxide [NO] synthesis) and induction of disseminated intravascular coagulation (DIC).

IL-1 is also produced by activated mononuclear cells in response to pro-inflammatory stimuli. IL-1 has two forms: IL-1α and IL-1β. IL-1α is active as its 33 kD molecule; IL-1β needs to be cleaved further to a 17 kD biologically active peptide. The endocrine effects of high doses of IL-1β are similar to TNF-α, causing fever, DIC, and metabolic wasting. Activated monocytes also produce IL-6 in response to IL-1 and TNF-α stimulation. IL-6 then acts on hepatocytes and B cells to propagate the inflammatory process. Under IL-6 stimulation, hepatocytes secrete increased levels of acute phase reactants, such as fibrinogen. IL-6 also acts as a B-cell growth factor, thereby promoting antibody formation and release.

In terms of modulating the inflammatory response (particularly down-regulating the response), modulation of the cytokine cascade has been a primary focus. Attempts have been made to alter the pro-inflammatory cytokine cascade to block a particular inflammatory molecule, thereby theoretically altering the cascade and potentially benefiting the patient. TNF-α and IL-1 are two such molecules targeted for modulation. Therapies with anti-TNF-α antibody and IL-1 receptor antagonist have been tested. However, to date targeting one specific cytokine or inflammatory mediator for immunotherapy has not generally proven to be a useful proposition for treatment. In this regard, it has generally been regarded that since any cytokine or mediator is only one component of the cascade, neutralising one agent is unlikely to down-regulate the entire cascade. It is for these reasons that the present findings are so surprising. First, it has been determined that the pro-inflammatory mediator cascade, from its earliest stages, involves modulation in the level of activin A expression. Specifically, activin A levels are increased shortly after the inflammatory stimulus occurs and prior to TNF-α, IL-1 and IL-6 expression. Accordingly, activin A appears to be involved in the initiation of the pro-inflammatory cytokine cascade. Still further, it has been determined that down-regulating activin A functionality can, in fact, achieve the favourable outcome of down-regulating the inflammatory response. A role for activin B during the early stages of the pro-inflammatory cytokine cascade has also been surprisingly elucidated. Still more surprisingly, however, has been the determination that the levels of activin B which are observed during this phase of an inflammatory response are significantly higher than the corresponding activin A levels.

Accordingly, in a preferred embodiment the present invention is directed to a method of modulating the inflammatory response in a mammal, said method comprising modulating the functional activity of activin, which activin is activin A or an activin molecule comprising the $\beta_B$ subunit, fragments, derivatives, mutants or variants thereof, wherein up-regulating said activin to a functionally effective level in said mammal induces, maintains or up-regulates the pro-inflammatory cytokine cascade and down-regulating said activin to a functionally ineffective level in said mammal inhibits or retards the pro-inflammatory cytokine cascade.

Preferably, said activin is activin A and/or activin B.

In one embodiment the present invention is directed to a method of modulating a local inflammatory response in a mammal, said method comprising modulating the functional activity of activin A and/or activin B, fragments, derivatives, mutants or variants thereof, wherein up-regulating activin to a functionally effective level in said mammal induces, maintains or up-regulates the local pro-inflammatory cytokine cascade and down-regulating activin A and/or activin B to a functionally ineffective level in said mammal inhibits or retards the local pro-inflammatory cytokine cascade.

Preferably, said local inflammatory response is acute.

In another preferred embodiment the present invention is directed to a method of modulating a systemic inflammatory response in a mammal, said method comprising modulating the functional activity of activin A and/or activin B, fragments, derivatives, mutants or variants thereof, wherein up-regulating activin to a functionally effective level in said mammal induces, maintains or up-regulates the pro-inflammatory cytokine cascade and down-regulating activin A and/or activin B to a functionally ineffective level in said mammal inhibits or retards the systemic pro-inflammatory cytokine cascade.

Preferably, said systemic inflammatory is acute.

In accordance with these preferred aspects of the present invention, said acute inflammatory response is preferably down-regulated and occurs in the context of, or is otherwise associated with, septic shock, septicaemia, airway inflammation, appendicitis, meningitis, hepatic response to toxins or viruses, angiogenesis, psoriasis, neural protection, atherosclerosis, renal tubular necrosis, encephalitis, or wound healing or traumatic injury such as occurs with injury, surgery and burns (e.g. traumatic brain injury).

Preferably, said airway inflammation occurs in the context of asthma, interstitial lung disease, cystic fibrosis, lung transplantation, bronchiolitis obliterans, emphysema, obstructive pulmonary disease, SARS, asbestosis, obstructive sleep apnoea, hypoxia or pulmonary hypertension.

Preferably, said acute systemic inflammatory response occurs in the context of systemic inflammatory response syndrome and even more particularly sepsis, septicaemia, toxic shock, septic shock, tissue trauma, meningitis or appendicitis.

In another preferred embodiment, said inflammatory disease is chronic.

Still more preferably, said chronic inflammatory response occurs in the context of, or is otherwise associated with multiple sclerosis, inflammatory bowel disease, rheumatoid arthritis, asthma, psoriasis or wound healing.

In accordance with these preferred embodiments, said pro-inflammatory cytokine cascade corresponds to the expression of TNF-α, IL-1 and/or IL-6.

It should be understood that in terms of modulating the pro-inflammatory cytokine cascade, this may be achieved either by modulating the actual levels of these cytokines or by modulating their functionality. For example, and without limiting the present invention to any one theory or mode of action, it has been shown that administration of follistatin (this molecule functioning as an activin antagonist) prior to the LPS challenge of a mammal nevertheless results in the expression of an activin A peak at a concentration which is the same as is normally observed to occur during inflammation. However, due to binding of the follistatin to the activin A, thereby blocking the functionality of activin A, the concentration of TNF-α which is expressed drops by 50%. Interestingly, the concentration of expressed IL-6 is observed to increase 6 fold at a significantly earlier time point. In total, these changes in the pro-inflammatory cytokine profile nevertheless result in a decrease in the observed inflammatory response. These findings are based on protein measurement and therefore indicate secretion and/or release of mature activin A dimeric protein. Accordingly, follistatin pre-treatment does not appear to affect this process. However, where activin βA and/or βB mRNA are measured, follistatin pre-treatment does in fact ameliorate the synthesis mechanisms of both activin subunit genes. With respect to the activin βA subunit, the inhibition of the mRNA is not reflected in protein release. The same mechanism is postulated to apply in the context of activin βB. Accordingly, still without limiting the present invention in any way, there occurs a rapid release of essentially pre-stored protein and then a follistatin-regulated synthesis pathway that is separate from this release mechanism. Of most significance, however, is the unexpected determination that there is observed a small increase in activin βA mRNA following inflammatory challenge but a massive increase in activin βB mRNA by the same stimulation.

Reference herein to attaining either a "functionally effective level" or "functionally ineffective level" of activin should be understood as a reference to attaining that level of activin at which modulation of the inflammatory response can be achieved, whether that be up-regulation or down-regulation. In this regard, it is within the skill of the person of skill in the art to determine, utilising routine procedures, the threshold level of activin expression above which or below which inflammation is modulated.

It should be understood that reference to an "effective level" means the level necessary to at least partly attain the desired response. The amount may vary depending on the health and physical condition of the cellular population and/or individual being treated, the taxonomic group of the cellular population and/or individual being treated, the degree of up or down-regulation which is desired, the formulation of the composition which is utilised, the assessment of the medical situation and other relevant factors. Accordingly, it is expected that this level may vary between individual situations, thereby falling in a broad range, which can be determined through routine trials.

Modulating activin levels may be achieved by any suitable means including, but not limited to:
(i) Modulating absolute levels of activin such that either more or less activin is present in the cellular environment.
(ii) Agonizing or antagonizing activin protein functional activity such that the functional effectiveness of activin is either increased or decreased. For example, increasing the half life of activin may achieve an increase in the functionally effective level of activin without actually necessitating an increase in the absolute concentration of activin. Similarly, the partial antagonism of activin may act to reduce, although not necessarily eliminate, the functional effectiveness of said activin.
Accordingly, this may provide a means of down-regulating activin functioning without necessarily down-regulating absolute concentrations of activin.

In terms of achieving the up or down-regulation of activin, means for achieving this objective would be well known to the person of skill in the art and include, but are not limited to:
(i) Introducing into a cell a nucleic acid molecule encoding activin or in order to up-regulate the capacity of said cell to express activin.
(ii) Introducing into a cell a proteinaceous or non-proteinaceous molecule which modulates transcriptional and/or translational regulation of a gene, wherein this gene may be the activin gene or functional portion thereof or some other gene or gene region (eg. promoter region) which directly or indirectly modulates the expression of the activin gene.
(iii) Introducing into a cell the activin expression product (this should be understood to include the use of activin homologues).
(iv) Introducing a proteinaceous or non-proteinaceous molecule which functions as an antagonist to the activin expression product.
(v) Introducing a proteinaceous or non-proteinaceous molecule which functions as an agonist of the activin expression product.

The proteinaceous molecules described above may be derived from any suitable source such as natural, recombinant or synthetic sources and includes fusion proteins or molecules which have been identified following, for example, natural product screening. The reference to non-proteinaceous molecules may be, for example, a reference to a nucleic acid molecule or it may be a molecule derived from natural sources, such as for example natural product screening, or may be a chemically synthesised molecule. The present invention contemplates analogues of the activin expression product or small molecules capable of acting as agonists or antagonists. Chemical agonists may not necessarily be derived from the activin expression product but may share certain conformational similarities. Alternatively, chemical agonists may be specifically designed to meet certain physiochemical properties. Antagonists may be any compound capable of blocking, inhibiting or otherwise preventing activin from carrying out its normal biological function.

Antagonists include monoclonal antibodies and antisense nucleic acids which prevent transcription or translation of activin genes or mRNA in mammalian cells. Modulation of expression may also be achieved utilising antigens, RNA, ribosomes, DNAzymes, aptamers, antibodies or molecules suitable for use in cosuppression. Suitable antisense oligonucleotide sequences (single stranded DNA fragments) of activin may be created or identified by their ability to suppress the expression of activin. The production of antisense oligonucleotides for a given protein is described in, for example, Stein and Cohen, 1988 (Cancer Res 48:2659-68) and van der Krol et al., 1988 (Biotechniques 6:958-976).

In the context of antibodies, the present invention envisages the use of any suitable form of antibody including catalytic antibodies or derivatives, homologues, analogues or mimetics of said antibodies. Such antibodies may be monoclonal or polyclonal and may be selected from naturally occurring activin or its subunits or may be specifically raised to the activin dimer or its monomers (herein referred to as the "antigen"). In the case of the latter, the antigen may first need to be associated with a carrier molecule. Alternatively, fragments of antibodies may be used such as Fab fragments or Fab'$_2$ fragments. Furthermore, the present invention extends to recombinant and synthetic antibodies and to antibody hybrids. A "synthetic antibody" is considered herein to include fragments and hybrids of antibodies. The antigen can also be used to screen for naturally occurring antibodies.

Both polyclonal and monoclonal antibodies are obtainable by immunization with the antigen or derivative, homologue, analogue, mutant, or mimetic thereof and either type is utilizable therapeutically. The methods of obtaining both types of sera are well known in the art. Polyclonal sera are less preferred but are relatively easily prepared by injection of a suitable laboratory animal with an effective amount of the antigen, or antigenic parts thereof, collecting serum from the animal, and isolating specific sera by any of the known immunoadsorbent techniques. Although antibodies produced by this method are utilizable, they are generally less favoured because of the potential heterogeneity of the product.

The use of monoclonal antibodies is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495-499, 1975; *European Journal of Immunology* 6: 511-519, 1976).

Preferably, the antibody of the present invention specifically binds the antigen. By "specifically binds" is meant high avidity and/or high affinity binding of an antibody to a specific antigen. Antibody binding to its epitope on this specific antigen is stronger than binding of the same antibody to any other epitope, particularly those that may be present in molecules in association with, or in the same sample, as the specific antigen of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g. by use of appropriate controls.

The proteinaceous and non-proteinaceous molecules referred to in points (i)-(v), above, are herein collectively referred to as "modulatory agents". To the extent that it is sought to decrease activin activity, said modulatory agent is preferably:

(i) follistatin. This may be administered either as a protein or its overexpression may be induced in vivo such as via the adenovirus mediated system described by Takabe et al. 2003.

(ii) any agent that upregulates the expression or functioning of the α subunit of inhibin. The α subunit can dimerise with the β subunits of activin to form inhibin, thereby effectively downregulating activin levels.

(iii) inhibin. This molecule can bind to β-glycan and inhibit the actions of activin via its receptor. See for example the mechanism described by Xu et al. (1995) or the use of the Smad7 antagonist (Bernard et al. 2004).

(iv) any agent that upregulates levels of $\beta_C$ since this results in the formation of the inactive AC form of activin.

(v) activin neutralising antibody. For example, as described in Poulaki et al. (2004).

(vi) activin mutants which inhibit native activin from binding to its receptor. For example, as described in Harrison et al. 2004.

(vii) transfection or treatment with a mutant activin receptor which prevents normal activin signalling. See for example, the system described by Maeshima et al. (2004).

In this regard, reference to "follistatin" should be read as including reference to all forms of follistatin including, by way of example, the three protein cores and six molecular weight forms which have been identified as arising from the alternatively spliced mRNAs FS315 and FS288. Accordingly, it should also be understood to include reference to any isoforms which may arise from alternative splicing of follistatin mRNA or mutant or polymorphic forms of follistatin. It should still further be understood to extend to any protein encoded by the follistatin gene, any subunit polypeptide, such as precursor forms which may be generated, and any follistatin protein, whether existing as a monomer, multimer or fusion protein. An analogous definition applies to "inhibin".

Screening for the modulatory agents hereinbefore defined can be achieved by any one of several suitable methods including, but in no way limited to, contacting a cell comprising the activin gene or functional equivalent or derivative thereof with an agent and screening for the modulation of activin protein production or functional activity, modulation of the expression of a nucleic acid molecule encoding activin or modulation of the activity or expression of a downstream activin cellular target. Detecting such modulation can be achieved utilising techniques such as Western blotting, electrophoretic mobility shift assays and/or the readout of reporters of activin activity such as luciferases, CAT and the like.

It should be understood that the activin gene or functional equivalent or derivative thereof may be naturally occurring in the cell which is the subject of testing or it may have been transfected into a host cell for the purpose of testing. Further, the naturally occurring or transfected gene may be constitutively expressed—thereby providing a model useful for, inter alia, screening for agents which down regulate activin activity, at either the nucleic acid or expression product levels, or the gene may require activation—thereby providing a model useful for, inter alia, screening for agents which up-regulate activin expression. Further, to the extent that an activin nucleic acid molecule is transfected into a cell, that molecule may comprise the entire activin gene or it may merely comprise a portion of the gene such as the portion which regulates expression of the activin product. For example, the activin promoter region may be transfected into the cell which is the subject of testing. In this regard, where only the promoter is utilised, detecting modulation of the activity of the promoter can be achieved, for example, by ligating the promoter to a reporter gene.

For example, the promoter may be ligated to luciferase or a CAT reporter, the modulation of expression of which gene can be detected via modulation of fluorescence intensity or CAT reporter activity, respectively. In another example, the subject of detection could be a downstream activin regulatory target, rather than activin itself. Yet another example includes activin binding sites ligated to a minimal reporter. Modulation of activin activity can be detected by screening for the modulation of pro-inflammatory cytokine release. This is an example of an indirect system where modulation of activin expression, per se, is not the subject of detection. Rather, modulation of the down-stream activity which activin regulates is monitored.

These methods provide a mechanism for performing high throughput screening of putative modulatory agents such as the proteinaceous or non-proteinaceous agents comprising synthetic, combinatorial, chemical and natural libraries. These methods will also facilitate the detection of agents which bind either the activin nucleic acid molecule or expression product itself or which modulate the expression of an upstream molecule, which upstream molecule subsequently modulates activin expression or expression product activity. Accordingly, these methods provide a mechanism of detecting agents which either directly or indirectly modulate activin expression and/or activity.

The agents which are utilised in accordance with the method of the present invention may take any suitable form. For example, proteinaceous agents may be glycosylated or unglycosylated, phosphorylated or dephosphorylated to various degrees and/or may contain a range of other molecules used, linked, bound or otherwise associated with the proteins such as amino acids, lipid, carbohydrates or other peptides, polypeptides or proteins. Similarly, the subject non-proteinaceous molecules may also take any suitable form. Both the proteinaceous and non-proteinaceous agents herein described may be linked, bound otherwise associated with any other proteinaceous or non-proteinaceous molecules. For example, in one embodiment of the present invention said agent is associated with a molecule which permits its targeting to a localised region.

The subject proteinaceous or non-proteinaceous molecule may act either directly or indirectly to modulate the expression of activin or the activity of the activin expression product. Said molecule acts directly if it associates with the activin nucleic acid molecule or expression product to modulate expression or activity, respectively. Said molecule acts indirectly if it associates with a molecule other than the activin nucleic acid molecule or expression product which other molecule either directly or indirectly modulates the expression or activity of the activin nucleic acid molecule or expression product, respectively. Accordingly, the method of the present invention encompasses the regulation of activin nucleic acid molecule expression or expression product activity via the induction of a cascade of regulatory steps.

The term "expression" refers to the transcription and translation of a nucleic acid molecule. Reference to "expression product" is a reference to the product produced from the transcription and translation of a nucleic acid molecule. Reference to "modulation" should be understood as a reference to up-regulation or down-regulation.

"Derivatives" of the molecules herein described (for example activin A, activin B, follistatin or other proteinaceous or non-proteinaceous agents) include fragments, parts, portions or variants from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, active regions of the molecule. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular epitopes or parts of the entire protein fused to peptides, polypeptides or other proteinaceous or non-proteinaceous molecules. For example, follistatin, or derivative thereof may be fused to a molecule to facilitate its localisation to a particular site. Analogues of the molecules contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences which may be utilised in accordance with the method of the present invention may similarly be derived from single or multiple nucleotide substitutions, deletions and/or additions including fusion with other nucleic acid molecules. The derivatives of the nucleic acid molecules utilised in the present invention include oligonucleotides, PCR primers, antisense molecules, molecules suitable for use in cosuppression and fusion of nucleic acid molecules. Derivatives of nucleic acid sequences also include degenerate variants.

A "variant" or "mutant" of activin or follistatin should be understood to mean molecules which exhibit at least some of the functional activity of the form of activin or follistatin of which it is a variant or mutant. A variation or mutation may take any form and may be naturally or non-naturally occurring.

A "homologue" is meant that the molecule is derived from a species other than that which is being treated in accordance with the method of the present invention. This may occur, for example, where it is determined that a species other than that which is being treated produces a form of activin or follistatin, for example, which exhibits similar and suitable functional characteristics to that of the activin or follistatin which is naturally produced by the subject undergoing treatment.

Chemical and functional equivalents should be understood as molecules exhibiting any one or more of the functional activities of the subject molecule, which functional equivalents may be derived from any source such as being chemically synthesised or identified via screening processes such as natural product screening. For example chemical or functional equivalents can be designed and/or identified utilising well known methods such as combinatorial chemistry or high throughput screening of recombinant libraries or following natural product screening. Antagonistic agents can also be screened for utilising such methods.

For example, libraries containing small organic molecules may be screened, wherein organic molecules having a large number of specific parent group substitutions are used. A general synthetic scheme may follow published methods (eg., Bunin B A, et al. (1994) Proc. Natl. Acad. Sci. USA, 91:4708-4712; DeWitt S H, et al. (1993) Proc. Natl. Acad. Sci. USA, 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing activin analogues which exhibit properties such as more potent pharmacological effects. Activin or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practicing the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

In addition to screening for molecules which mimic the activity of activin one may identify and utilise molecules which function agonistically or antagonistically to activin in order to up or down-regulate the functional activity of activin in relation to modulating cellular growth. The use of such molecules is described in more detail below. To the extent that the subject molecule is proteinaceous, it may be derived, for example, from natural or recombinant sources including fusion proteins or following, for example, the screening methods described above. The non-proteinaceous molecule may be, for example, a chemical or synthetic molecule which has also been identified or generated in accordance with the methodology identified above. Accordingly, the present invention contemplates the use of chemical analogues of activin capable of acting as agonists or antagonists. Chemical agonists may not necessarily be derived from activin but may share certain conformational similarities. Alternatively, chemical agonists may be specifically designed to mimic certain physiochemical properties of activin. Antagonists may be any compound capable of blocking, inhibiting or otherwise preventing activin from carrying out its normal biological functions. Antagonists include monoclonal antibodies specific for activin or parts of activin. Preferably, said antagonist is follistatin.

Analogues of activin or of activin agonistic or antagonistic agents contemplated herein include, but are not limited to, modifications to side chains, incorporating unnatural amino acids and/or derivatives during peptide, polypeptide or protein synthesis and the use of crosslinkers and other methods which impose conformational constraints on the analogues. The specific form which such modifications can take will depend on whether the subject molecule is proteinaceous or non-proteinaceous. The nature and/or suitability of a particular modification can be routinely determined by the person of skill in the art.

For example, examples of side chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl--aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |

TABLE 1-continued

| Non-conventional amino acid | Code |
| --- | --- |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Crosslinkers can be used, for example, to stablise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

Modulation of said activin functional levels may be achieved via the administration of said activin, a nucleic acid molecule encoding said activin or an agent which effects modulation of said activin activity or said activin gene expression (herein collectively referred to as "modulatory agents"). Preferably, the subject method is utilised to down-regulate the inflammatory response in a mammal.

Accordingly, in a particularly preferred embodiment the present invention is directed to a method of down-regulating the inflammatory response in a mammal, said method comprising administering to said mammal an effective amount of an agent for a time and under conditions sufficient to induce a functionally ineffective level of activin, which activin is activin A or an activin molecule comprising a $β cytokine cascade and down-regulating said activin to a functionally ineffective level inhibits or retards the pro-inflammatory cytokine cascade.

Preferably, said activin is activin A and/or activin B.

Preferably, said pro-inflammatory cytokine cascade is characterised by the expression of TNF-α, IL-1 and/or IL-6.

Reference to an "aberrant, unwanted or otherwise inappropriate" inflammatory response should be understood as a reference to an excessive response, an inadequate response or to a physiologically normal response which is inappropriate in that it is unwanted or otherwise inappropriate. Examples of aberrant or otherwise unwanted inflammatory responses include those which occur in the context of septic shock, septicaemia, airway inflammation, appendicitis, meningitis, hepatic response to toxins or viruses, angiogenesis, psoriasis, neural protection, atherosclerosis, renal tubular necrosis, or wound healing or traumatic injury such as occurs with surgery and burns. In this regard, however, some forms of airway inflammation in fact reflect normal physiological responses which are unwanted, such as those which occur in the context of allergy or asthma. Examples of inadequate responses include the failure of any significant inflammatory response to occur as part of an immunisation regime.

Accordingly, the subject inflammatory response is preferably an unwanted acute inflammatory response of either the local or systemic type.

There is therefore preferably provided a method of therapeutically and/or prophylactically treating a condition, or a predisposition to the development of a condition, characterised by an unwanted acute inflammatory response in a mammal, said method comprising down-regulating the level of activin, which activin is activin A or an activin molecule comprising a $\beta_B$ subunit, fragments, derivatives, mutants or variants thereof, in said mammal wherein down regulating said activin to a functionally ineffective level inhibits or retards the pro-inflammatory cytokine cascade.

Preferably, said activin is activin A and/or activin B.

In accordance with this preferred embodiment of the present invention, said condition is septic shock, septicaemia, airway inflammation, appendicitis, meningitis, encephalitic, hepatic response to toxins or viruses, angiogenesis, psoriasis, neural protection, atherosclerosis, renal tubular necrosis, or wound healing or traumatic injury such as occurs with injury, surgery and burns (e.g. traumatic brain injury).

Preferably, said airway inflammation occurs in the context of asthma, interstitial lung disease, cystic fibrosis, lung transplantation, bronchiolitis obliterans, emphysema, obstructive pulmonary disease, SARS, asbestosis, obstructive sleep apnoea, hypoxia or pulmonary hypertension.

More preferably, said condition is systemic inflammatory response syndrome and even more particularly sepsis, septicaemia, toxic shock, septic shock, tissue trauma, meningitis or appendicitis.

In another preferred embodiment, said inflammatory disease is chronic.

Still more preferably, said chronic inflammatory response occurs in the context of, or is otherwise associated with multiple sclerosis, inflammatory bowel disease, rheumatoid arthritis, asthma, psoriasis or wound healing.

In another preferred embodiment there is provided a method of therapeutically and/or prophylactically treating a condition, or a predisposition to the development of a condition, characterised by an inadequate inflammatory response in a mammal, said method comprising modulating the level of activin, which activin is activin A or an activin molecule comprising a $\beta_B$ subunit, fragments, derivatives, mutants or variants thereof, in said mammal wherein up-regulating said activin to a functionally effective level up-regulates the pro-inflammatory cytokine cascade.

Preferably, said activin is activin A and/or activin B.

These therapeutic and prophylactic aspects of the present invention are preferably achieved by administering an effective amount of a modulatory agent, as hereinbefore defined, for a time and under conditions sufficient to appropriately modulate the pro-inflammatory cytokine cascade.

An "effective amount" means an amount necessary at least partly to attain the desired response, or to delay the onset or inhibit progression or halt altogether, the onset or progression of the particular condition being treated. The amount varies depending upon the health and physical condition of the individual to be treated, the taxonomic group of the individual to be treated, the degree of protection desired, the formulation of the composition, the assessment of the medical situation, and other relevant factors. It is expected that the amount will fall in a relatively broad range that can be determined through routine trials.

Preferably, to the extent that one is seeking to down-regulate an inflammatory response, said agent is follistatin or functional fragments, derivative, homologue or mimetic thereof, an agent that upregulates the levels of the α subunit of inhibin, inhibin, an agent that upregulates the levels of $\beta_C$, an activin neutralising antibody or an activin mutant.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the modulatory agent together with other proteinaceous or non-proteinaceous molecules which may facilitate the desired therapeutic or prophylactic outcome. For example, one may combine the method of the present invention with radiotherapy or chemotherapy.

Administration of molecules of the present invention hereinbefore described [herein collectively referred to as "modulatory agent"], in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 µg to about 1 mg of modulatory agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in a convenient manner such as by the oral, intravenous (where water soluble), respiratory, transdermal, intraperitoneal, intramuscular, subcutaneous, intradermal or suppository routes or implanting (e.g. using slow release molecules). The modulatory agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, transdermally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip, patch and implant. Preferably, said means of administration is inhalation with respect to the treatment of airway inflammation and intravenously, intramuscularly or transdermally for other conditions.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effects. By "sequential" administration is meant a time difference of from seconds, minutes, hours or days between the administration of the two types of molecules. These molecules may be administered in any order.

In accordance with the present invention, although the preferred method is to therapeutically treat unwanted acute inflammatory responses, in certain circumstances one may also seek to treat chronic inflammatory conditions. It is appreciated that achieving the down-regulation of a chronic inflammatory response is unlikely to reverse any tissue remodelling (scar formation) which has already occurred. However, such a method could prevent the occurrence of any further tissue damage. With respect to the prophylactic applications of the present invention, there are many circumstances where one may wish to institute a preventative treatment regime. For example, one may institute such a regime in patients who are predisposed to developing an autoimmune condition, patients who have suffered a tissue trauma such as severe burns, patients undergoing an organ transplant, cystic fibrosis patients, asthma/allergy sufferers or those prone to breathing disorders such as sleep apnoea.

Another aspect of the present invention relates to the use of an agent capable of modulating the functionally effective level of activin fragments, derivatives, mutants or variants thereof, in the manufacture of a medicament for the therapeutic and/or prophylactic treatment of a condition, or a predisposition to the development of a condition, characterised by an aberrant, unwanted or otherwise inappropriate inflammatory response in a mammal wherein up-regulating activin to a functionally effective level up-regulates the pro-inflammatory mediator cascade and down-regulating activin to a functionally ineffective level inhibits or retards the pro-inflammatory mediator cascade.

More particularly, the present invention relates to the use of an agent capable of modulating the functionally effective level of activin, which activin is activin A or an activin molecule comprising a $\beta_B$ subunit, fragments, derivatives, mutants or variants thereof, in the manufacture of a medicament for the therapeutic and/or prophylactic treatment of a condition, or a predisposition to the development of a condition, characterised by an aberrant, unwanted or otherwise inappropriate inflammatory response in a mammal wherein up-regulating said activin to a functionally effective level up-regulates the pro-inflammatory cytokine cascade and down-regulating said activin to a functionally ineffective level inhibits or retards the pro-inflammatory cytokine cascade.

Preferably, said inflammatory response is an acute inflammatory response of either the acute or systemic type.

In accordance with these preferred aspects of the present invention, said acute inflammatory response is preferably down-regulated and said condition is septic shock, septicaemia, airway inflammation, appendicitis, meningitis, hepatic response to toxins or viruses, angiogenesis, psoriasis, neural protection, atherosclerosis, renal tubular necrosis, wound healing or traumatic injury such as occurs with injury, surgery and burns and said inflammatory response is down-regulated.

Preferably, said airway inflammation occurs in the context of asthma, interstitial lung disease, cystic fibrosis, lung transplantation, bronchiolitis obliterans, emphysema, obstructive pulmonary disease, SARS, asbestosis, obstructive sleep apnoea, hypoxia or pulmonary hypertension.

Preferably, said acute systemic inflammatory response occurs in the context of systemic inflammatory response syndrome and even more particularly sepsis, septicaemia, toxic shock, septic shock, tissue trauma, meningitis or appendicitis.

In another preferred embodiment, said inflammatory disease is chronic.

Still more preferably, said chronic inflammatory response occurs in the context of, or is otherwise associated with multiple sclerosis, inflammatory bowel disease, rheumatoid arthritis, asthma, psoriasis or wound healing.

In yet another further aspect, the present invention contemplates a pharmaceutical composition comprising the modulatory agent as hereinbefore defined together with one or more pharmaceutically acceptable carriers and/or diluents. Said agents are referred to as the active ingredients The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 μg and 2000 mg of active compound.

The agent may also be prepared for administration via the airway in either a particulate or soluble form. For example, the agent may be administered via an oral inhaler or a nebuliser.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding activin A or a modulatory agent as hereinbefore defined. The vector may, for example, be a viral vector.

The present invention is defined by the following non-limiting examples.

Example 1

Materials and Methods

Animals and General Experimental Details.

All experiments were conducted in accordance with the NHMRC Australian Code of Practice for the Care of Animals for Scientific Purposes (1997) and were approved by the Monash University Animal Ethics Committee.

One hundred and twenty six male C57BI/6 mice (4-8 weeks), were randomly allocated into two groups; Group 1 consisted of nine sub-groups of eight animals (total n=72) while Group 2 consisted of nine subgroups of six animals (n=54). All animals were kept in standard animal housing with access to food and water throughout the experiment. Lipopolysaccharide (LPS) (E. coli serotype 0127:B8, Sigma, St. Louis, Mo., USA) was purified using a phenol-water extraction method as previously described (Manthey et al. 1994, J Immunol 153:2653-63), and administered as an intraperitoneal bolus injection of 100 μg in 100 μl of isotonic, non-pyrogenic saline solution per mouse. Recombinant human follistatin-288 (rhfollistatin-288; Biotech, Australia) was administered as an intraperitoneal injection of 1 μg in 100 μl of isotonic, non-pyrogenic saline solution, 30 minutes prior to LPS. Group 1 received injections of LPS and rhfollistatin-288 while Group 2 received an injection of LPS alone. Mice were then anaesthetized with an inhalant form of isoflurane (Abbott Australasia LTD, Kurnell, Australia), and sacrificed for blood collection at 30 minutes, 1, 2, 3, 5, 8, 12 and 24 hours and one group was sacrificed without an injection to act as controls for basal levels. Blood was collected into a 1.5 ml centrifuge tube containing 50 μl of ethylene diaminetetraacetic acid (EDTA, BDH Laboratory Supplies, Poole, UK) and centrifuged at 250 g at room temperature with plasma removed and stored at −20° C. until assayed for activin A, follistatin, TNFα, IL-6 and IL-1β.

Assays

Activin A was measured by ELISA as previously described using human recombinant activin A as a standard (Knight et al., J Endocrinol 148:267-79). This ELISA measures both free and follistatin-bound activin and does not cross react significantly with other isoforms of activin (Knight et al., supra). The mean sensitivity was 0.01 ng/ml, and the mean intra- and inter-assay coefficients of variations (CVs) were 3.9% and 5.1% respectively.

Follistatin concentrations in serum were measured with a radioimmunoassay as previously described (O'Connor et al., Hum Reprod. 14:827-832). The standard and tracer employed was rhfollistatin-288. As with the Activin A ELISA, this RIA measures both free and bound forms of follistatins. The mean assay sensitivity was 2.7 ng/ml. $ED_{50}$ was 13.3 ng/ml, and the intra- and inter-assay CVs were 6.4% and 10.2%, respectively.

Mouse cytokines TNFα, IL-6 and IL-1β were measured by ELISA (R&D Systems, Minneapolis, Minn., USA). These assays use mouse recombinant proteins as standards and monoclonal antibodies for detection. The sensitivity of TNFα assay was 0.5 ng/ml, and the intra- and inter-assay CVs were <10%. The sensitivity of the IL-6 assay was 0.2 ng/ml and the intra- and inter-assay CVs were <10% and 12% respectively. The sensitivity of the IL-1β was ng/ml and the intra- and inter-assay CVs were <10% and <11%, respectively.

Data Analysis

All data was analysed using a one way ANOVA with a paired t-test used to compare differences between time points in the different treatment groups.

Results

The Role of Activin A in Mice Following an Intraperitoneal LPS Challenge

Figure 1B:
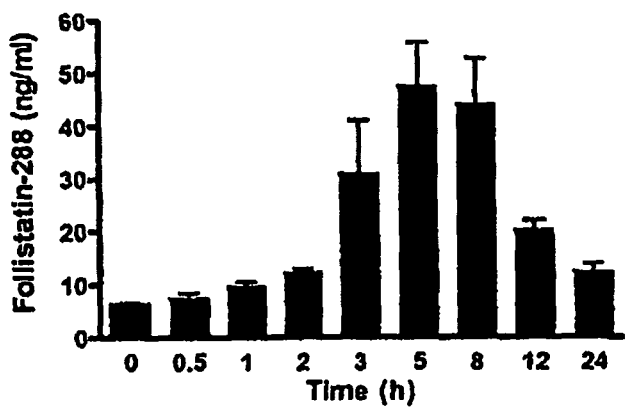
FIG. 1B is a graphical representation of follistatin release in response to LPS.
Figure 1C:
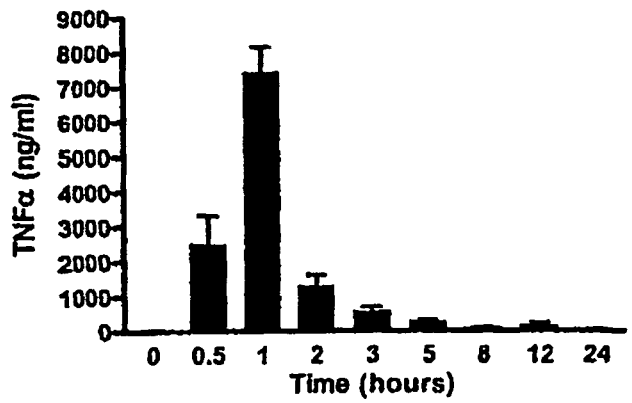
FIG. 1C is a graphical representation of TNFα release in response to LPS.
Figure 1D:
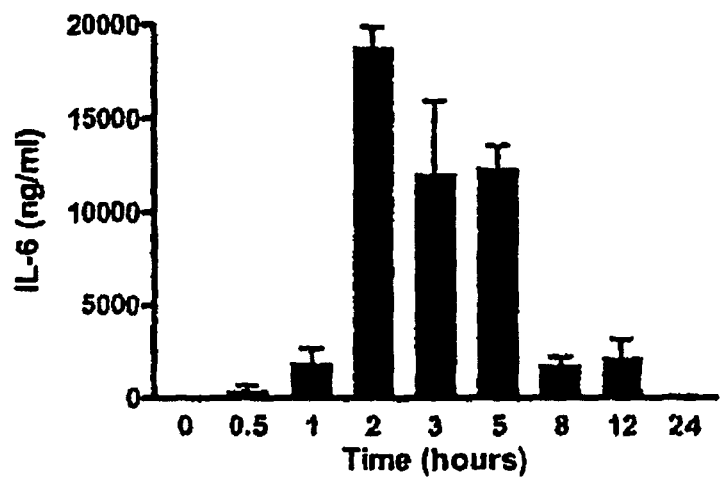
FIG. 1D is a graphical representation of IL-6 release in response to LPS.
Figure 1E:
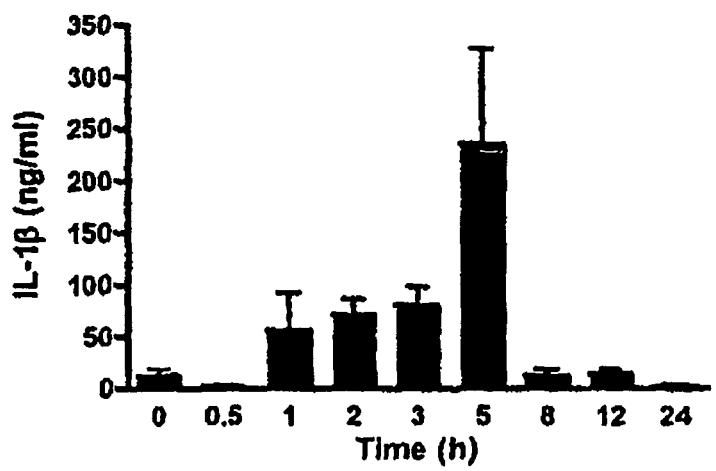
FIG. 1E is a graphical representation of IL-1β release in response to LPS.

A robust release of activin A was observed in the mice following an injection of re-extracted LPS. Levels of activin A increased within 30 minutes following LPS administration and peaked at 1 hour returning to baseline levels between 3 to 8 hours, followed by a subsequent increase at 12 hours before returning again to baseline levels at 24 hours (FIG. 1A). Following LPS administration, follistatin was released into the circulation but was delayed compared to activin A, increasing at 3 hours and remaining elevated until 24 hours (FIG. 1B). The release of TNFα into the circulation was observed to follow the classic monophasic peak, increasing at 0.5 hours (p<0.01) post LPS administration, peaking at 1 hour and returning to basal levels at 5 to 8 hours (FIG. 1C). Serum IL-6 was elevated subsequent to elevations in TNFα, increasing between 1 and 2 hours, peaking at 2 hours (p<0.01) and remaining elevated until between 5 (p<0.01) and 8 hours (FIG. 1D). The levels of IL-1β in the circulation were significantly lower than TNFα or IL-6 (30-50 fold) with IL-1β increasing 1 hour post injection and peaking at 5 hours (p<0.01) before returning to basal levels at 8 hours (FIG. 1E).

Figure 2A:
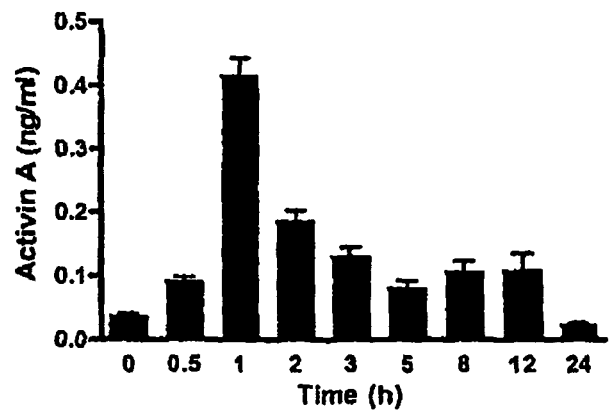
FIG. 2A is a graphical representation of activin A release following an injection of LPS in mice that received an injection of recombinant human follistatin-288 (rhfollistatin-288) 30 minutes prior to LPS.
Figure 2B:
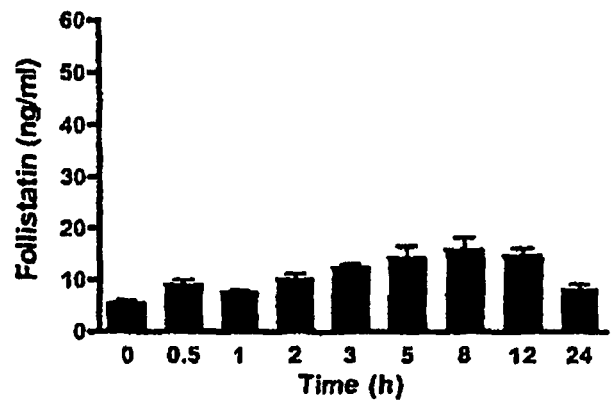
FIG. 2B is a graphical representation of release of follistatin in mice following administration of rhfollistatin-288 30 minutes prior to LPS.
Figure 2C:
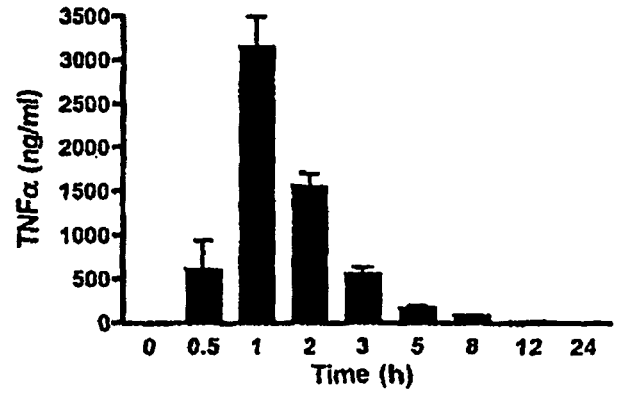
FIG. 2C is a graphical representation of the level of TNFα released in mice following administration of rhfollistatin-288 30 minutes prior to LPS.
Figure 2D:
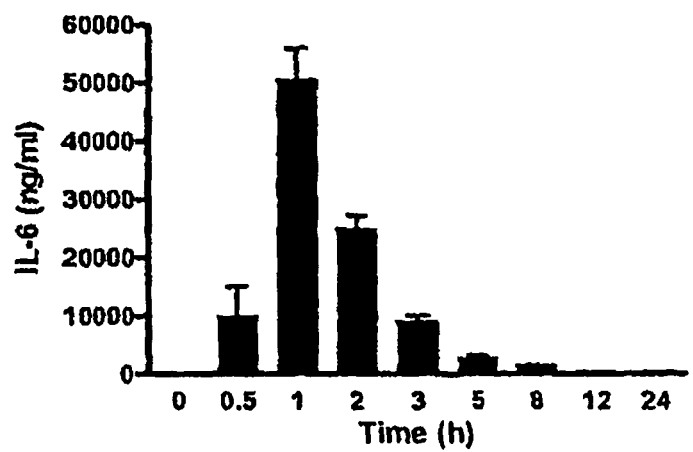
FIG. 2D is a graphical representation of the level of interleukin-6 released following injection of rhfollistatin-288 followed by an injection of LPS.
Figure 2E:
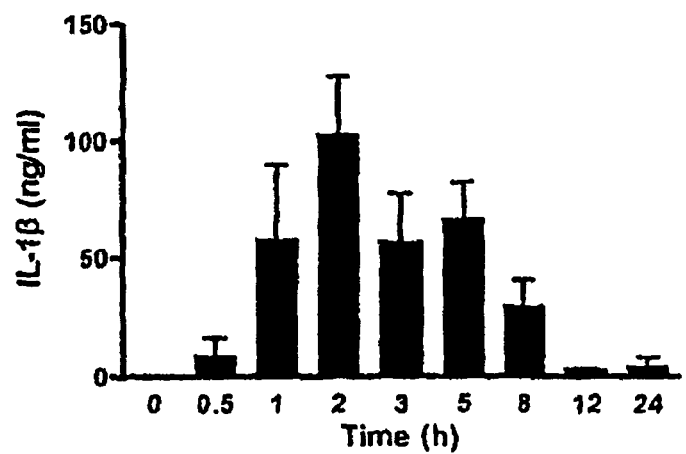
FIG. 2E is a graphical representation of the level of IL-1β released following injection of follistatin followed by LPS.

The peak release of activin A was unaffected by the administration of rhfollistatin-288. Following LPS administration activin A release into the circulation was still rapid and robust peaking at 1 hour and returning to basal levels within 5 hours (FIG. 2A). Interestingly, the concentration of circulatory mouse follistatin-288 was significantly suppressed over the entire peak period, 5-8 hours (p<0.03) following LPS administration in mice injected with rhfollistatin-288 (FIG. 2B). Additionally, TNFα release was significantly suppressed (50% suppression) by administration of rhfollistatin-288 prior to injection of LPS (p<0.01) although the profile of release was not significantly altered (FIG. 2C). Conversely, IL-6 release was altered in both absolute amounts and temporally. Interestingly, IL-6 peak concentrations were significantly increased (p<0.01) in mice administered rhfollistatin-288 prior to LPS by approximately 2 fold (FIG. 2D). Furthermore, increases in IL-6 occurred earlier in the presence of rhfollistatin-288, peaking at 1 hour as compared to 2 hours in mice receiving LPS alone. Release of IL-1β was not as evident in the presence of rhfollistatin-288 when compared to mice that received LPS alone (FIG. 2E). Additionally, the profile also shifted such that elevations in serum concentrations occurred earlier in the presence of rhfollistatin-288, peaking at 2 hours compared to 5 hours in mice receiving LPS alone (p<0.01). However, it should be noted that there was not a significant difference in the concentrations of IL-1β at any time point.

Example 2

Activin and Follistatin in a Mouse Model of Experimental Allergic Asthma

Pilot data from our ovalbumin (OVA) sensitisation and challenge model of allergic asthma highlights major changes in activin expression during the evolution of the pulmonary inflammatory response.

Figure 3:
FIG. 3 is an image of activin A expression in (A) bronchial epithelium and inflammatory infiltrate, (B) diffuse expression on submucosal smooth muscle and vascular structures (arrows) and (C) expression on bronchial epithelium and discrete inflammatory cells (arrows). A and B, asthma; C, cystic fibrosis. Immunoperoxidase, original magnification ×400.
Figure 4:
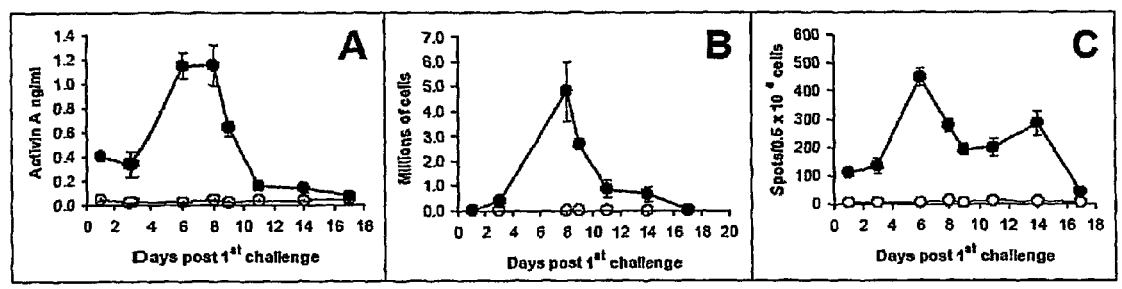
FIG. 4 is a graphical representation of kinetics of activin A expression and lung inflammation in our OVA murine model. (A) Activin concentration in BALF as measured by ELISA, (B) absolute eosinophil numbers in BAL, and (C) frequency of IL-4-producing mediastinal lymph node cells as measured by ELISPOT. Mean±SEM, n=5 mice per group per timepoint.

Compartmentalisation of activin and follistatin is observed in a mouse model of allergic asthma, and activin expression in various cellular sites in lung tissue from asthmatic and cystic fibrosis patients (FIG. 3). The kinetics of activin secretion have been mapped finding that the peak concentration in BALF (FIG. 4A) coincides with peak inflammation and eosinophilia (FIG. 4B), and the production of IL-4 (FIG. 4C).

Figure 5:
FIG. 5 is an image of activin A expression in saline control (A) and OVA sensitized mice after 4 challenges (B), and 10 days after the 4th challenge (C). Arrows indicate loss of activin A expression in hypertrophied bronchial epithelium (B), and patchy expression at day 17 (C).

Immunohistochemical analysis of activin expression in the lung shows that activin is expressed in airway epithelium from control (saline) mice (FIG. 5A). However, after 4 OVA challenges (day 8) the airway undergo profound changes, with epithelial cell hypertrophy and marked loss of activin expression (FIG. 5B). These alterations persist until day 17 (10 days after final challenge), although activin expression becomes variable between adjacent airway and even within the same airway (FIG. 5C). Collectively, these findings indicate that pre-stored activin is released into the surrounding tissue during the inflammatory response. A general trend toward normal airway morphology and activin expression at the later time points suggests that this remodelling process is reversible. Finally, preliminary immunohistochemical analysis reveals loss of follistatin expression in bronchial epithelium after OVA challenge very similar to the pattern seen for activin.

Example 3

Characterisation of Pulmonary Expression of Activin and Follistatin

Activin and Follistatin mRNA Expression and Activin Receptor Compartmentalisation in the Mouse Using a sensitisation and challenge protocol with OVA as allergen we have found a correlation between magnitude of the inflammatory response and differential regulation of activin and follistatin expression in bronchial epithelium versus BALF has been found. The finding that activin protein is dramatically decreased in bronchial epithelial cells mandates that activin and follistatin expression should be assessed at multiple time-points during and following the immunisation protocol. Mice are sensitised with OVA (50 µg in aluminium hydroxide) on days 0 and 12, and challenged via intratracheal intubation with OVA (25 µg) on days 24, 26, 28 and 30 (Hardy et al., 2003, *Am J Respir Crit Care Med* 167:1393-1399). Control mice receive saline instead of OVA. Mice are killed (n=6 per group) after each of 4 allergen challenges, and on days 2, 4, 7, 10 and 20 after the final OVA challenge. Immunohistochemistry is performed on formalin-fixed lung. Activin and follistatin are detected with specific antibodies (E4, raised against the human activin βA subunit; 2E6, raised against human recombinant follistatin) which cross-react with mouse; isotype matched antibodies serve as controls. Primary antibodies are detected with appropriate anti-mouse-horseradish peroxidase antibodies. Measurement of activin A in BALF and serum is according to an established enzyme linked ELISA protocol (Knight et al., 1996, supra) using human recombinant activin A standard. Follistatin concentration in BALF and serum are measured using a discontinuous radioimmunoassay (O'Connor et al., 1999, supra). An established real-time RT-PCR protocol is used to quantitate activin and follistatin mRNA in lung tissue. Immunohistochemistry (Santa Cruz Biotechnology) is also used to evaluate expression of type I and II activin receptors to determine which cells might be responsive to activin. In a smaller number of time-points non-radioactive in situ hybridisation is performed to determine the localisation of activin receptor mRNAs to measure any change in the compartmentalisation of mRNAs concomitant with the shift in protein localisation. Activin and follistatin staining intensity in epithelium and bronchial submucosa is scored using double blind analysis on a scale of 0=absent, 1=weak, 2=moderate, and 3=high intensity. Ten bronchioles of internal diameter 150-200 µm from each mouse are analysed to arrive at scores for individual mice.

Activin and Follistatin Expression in Human Airway Disease

A detailed immunochemical analysis of activin and follistatin expression in normal, asthmatic and cystic fibrosis lung tissue and BAL (see methods above) is performed. Tissue specimens are obtained from stored and prospective lung tissue samples resected at the time of transplantation (severe cystic fibrosis n=20), with the co-operation of the Heart Lung Transplantation Service, The Alfred Hospital, Melbourne. Asthmatic tissue are available from stored resected lung tissue and prospective endobronchial biopsy tissue from asthmatic patients undergoing bronchoscopy for intercurrent diagnostic reasons (n=10). Age-matched control airway from non-smokers with no known history of airway disease are collected from fresh post mortem specimens provided by The Department of Anatomical Pathology (n=20). Tissue is collected from proximal airway (right lower lobe bronchus) at the time of lung resection. Specimens are fixed in each of: (1) chilled acetone with protease inhibitors at −20° C. for later embedding in glycol methacrylate (GMA), and (2) ethanol and formalin for subsequent paraffin embedding.

Example 4

Defining the Relationship Between Activin and Follistatin Expression and Pulmonary Inflammation Key aspects of the allergic inflammatory response are measured in order to characterise the relationship between activins and follistatin and magnitude of the inflammatory response. Mice (n=6 per group) are sensitised and challenged with OVA (as outlined in Aim 1), and killed after each of 4 allergen challenges, and on days 2, 4, 7, 10 and 20 after the final OVA challenge. Serum is collected from whole blood, and tested for presence of OVA-specific IgE and $IgG_1$ by sandwich ELISA. Lung tissue is fixed in formalin prior to paraffin embedding; sections are stained with haematoxylin and eosin and periodic acid-Schiff for microscopic assessment of inflammation and for determination of mucus-producing cell frequency. BAL and mediastinal lymph node single-cell suspensions are counted. BAL cell cytospots are Giemsa stained and differential counts performed on ≥200 cells per mouse; cells are identified by morphologic criteria Frequency of IL-4, IL-5, IL-13 and IFN-γ producing cells in OVA-stimulated mediastinal lymph nodes are determined by ELISPOT (BD Biosciences and R&D Systems). ELISPOT plates are read on an AID ELISPOT Reader. BALF is collected after cell counts have been performed, and stored at −70° C. for subsequent analysis of the above cytokines by sandwich ELISA. Additionally, formalin-fixed lung tissue from control, asthmatic and cystic fibrosis patients is immunohistochemically stained to detect mast cells (AA1, Dako), eosinophils (eosinophil major basic protein, eosinophil peroxidase, BD Biosciences), T lymphocytes (CD3, Dako) and macrophages (CD68, PGM1, Dako). Cells are counted using a 3-layer amplification system with streptavidin biotin-peroxidase and AEC (Sigma-Aldrich) as the substrate. Counts are performed using an image analyser (Image-Pro Plus, MediaCybernetics) to a depth of 150 μm below the basement membrane and expressed as cells per $mm^2$. The expression of key Th2 cytokines are measured in BALF from patients and controls (BD Biosciences).

Example 5

Correlating Activin and Follistatin Expression with Airway Remodelling

Remodelling events in stored and prospective samples from normal (n=20), asthmatic (n=10) and cystic fibrosis (n=20) human lung are analysed. Morphometric image analysis and immunohistochemistry are used to measure key indices of the remodelling response including: (i) thickening of the sub-epithelial basement membrane, (ii) fibroblast proliferation, (iii) myofibroblast hyperplasia, (iv) airway smooth muscle hypertrophy/hyperplasia, and (v) angiogenesis. Sub-epithelial basement membrane thickness and angiogenesis are measured using well established protocols (Li et al., 1997, *Am J Respir Crit Care Med* 156:229-233; Wilson et al., 1997, *Clin Exp Allergy* 27:363-371; Orsida et al., 1999, *Thorax* 54:289-295). Airway smooth muscle hypertrophy and hyperplasia are assessed on haematoxylin & eosin stained sections (Image-Pro Plus) by measuring smooth muscle cell diameter in μm (diameter across the nucleus) and percentage smooth muscle in the bronchial submucosa (Benayoun et al., 2003, *Am J Respir Crit Care Med* 167:1360-1368). Additionally, airway smooth muscle hypertrophy are assessed immunohistochemically by scoring intensity of α-smooth muscle actin and myosin light chain kinase expression (Sigma-Aldrich) on a scale of 0-3 (see Aim 1) (Benayoun et al., 2003, supra). Fibroblast proliferation is assessed immunohistochemically on formalin-fixed sections using antibody specific for proliferating cell nuclear antigen (PCNA, Dako). Fibroblasts are identified using morphological criteria and staining for prolyl-4-hydroxylase (Dako). The number of PCNA-positive fibroblasts below the basement membrane are counted, normalised to the basement membrane length and expressed per $mm^2$ of quantifiable biopsy area (Image-Pro Plus). All parameters are measured on at least 2 serial sections for each patient.

Example 6

Investigating Whether Follistatin Treatment Prevents Pulmonary Inflammation and Enhances Resolution in a Murine Model Follistatin Modulation of Activin Expression and Release—Murine Model of Acute Asthma Activin function is regulated by a number of binding proteins, the best studied being its interaction with the high-affinity binding protein follistatin. Binding to human recombinant follistatin effectively blocks interaction with the activin receptor, thereby neutralising the biological actions of activin A (Phillips, 2000, *Bioessays* 22:689-696). Using mouse asthma models, the ability of follistatin to modulate activin expression and release in lung, BAL and serum is assessed, comparing different follistatin doses and routes of administration. Intraperitoneal injection of 1 μg follistatin per adult mouse 0.5 hour prior to LPS injection blocks the rise in follistatin seen 4 hours later, and suppresses release of proinflammatory cytokines (TNF-α and IL-1β), while activin release is unimpaired. Thus follistatin treatment blocks activin-induced effects, but not its release. Initially, mice (n=6 per group) receive i.p. 1 μg follistatin per mouse, 0.5 hour prior to each of the four OVA challenges. This route of follistatin delivery is compared with intranasal and intratracheal administration testing varying doses and timings of administration. Control mice receive saline. Activin A and follistatin expression is monitored by ELISA in BALF, and by RT-PCR and immunohistochemistry in the lung (see Aim 1) following each of the four OVA challenges, and on days 2, 4, 7, 10 and 20 after the final OVA challenge. The latter time point reveals whether activin A expression returns to pre-challenge levels in untreated OVA mice, and gives an indication as to the duration of the follistatin-induced blockade of activin.

Secondly, a determination if made of whether neutralisation of activin A by follistatin lessens the severity and duration of the allergic pulmonary inflammation. The ability of follistatin to attenuate pulmonary inflammation by measuring key 'allergic' parameters including specific IgE and $IgG_1$, eosinophilia, mucus hypersecretion, and cytokine production is investigated. Mice are killed following each of the four OVA challenges, and on days 2, 4, 7, 10 and 20 after the final OVA challenge. Blood, BAL, lungs and mediastinal lymph nodes are collected for enumeration of inflammatory cells, OVA-specific IgE and $IgG_1$, eosinophilia, mucus production and ELISPOT analysis of IL-4, IL-5, IL-13, and IFN-γ. (methods as per Aim 1). Since TGF-β is also involved in immunoregulation and tissue remodelling, TGF-β concentration in BALF is measured (R&D Systems) and TGF-β expression in tissue sections is measured by immunohistochemistry (Santa Cruz Biotechnology) to determine whether its production is modulated by activin/follistatin (Lee et al., 2001, *J Exp Med* 194:809-821). These data provide information regarding the ability of activin neutralisation to ameliorate allergic pulmonary inflammation.

Follistatin Modulation of Activin Expression and Release—Murine Model of Chronic Asthma Repeat antigen dosing at non-tolerogenic time intervals for up to six weeks is performed in murine model of chronic asthma (2 challenges/week on Monday and Thursday) to induce sustained airway inflammation and chronic remodelling (Coyle et al., 1996, *J Immunol* 156:2680-2685). Mice are treated with follistatin according to the dose and route optimised above. The effects of follistatin treatment on remodelling in this mouse model are assessed by measuring: (i) sub-epithelial basement membrane thickening, (ii) angiogenesis, (iii) smooth muscle hypertrophy, and (iv) mucus cell induction (Lee et al., 2001, supra; Kumar et al., 2002, *Clin Exp Allergy* 32:1104-1111). Sub-epithelial basement membrane thickness, angiogenesis and smooth muscle hypertrophy are assessed. Metaplasia and/or hyperplasia of mucus-secreting goblet cells is assessed. These data provide information regarding the ability of follistatin to inhibit the airway remodelling response.

Statistical Analysis

The distribution of each data set is tested for normality before analysis. Normally distributed data is analysed using one-way ANOVA with Bonferroni's correction for multiple comparisons. Individual comparisons between groups is made using a two-tailed Student's t-Test. Relationships between activin/follistatin expression and either inflammation or remodelling indices is analysed using Pearson's correlation.

Data that are not normally distributed are analysed using the non-parametric Kruskal-Wallis Test followed by Dunn's Multiple Comparisons post-hoc test. Individual comparisons between groups are made using a two-tailed Mann-Whitney U-Test for non-parametric data. Relationships between activin/follistatin expression and either inflammation or remodelling indices are explored using Spearman's rank correlation. A P value of ≤0.05 will be considered significant.

Example 7

Profound Changes in Activin $\beta_B$ During Localised and Systemic Inflammation Materials and Methods
Experimental Design For the systemic LPS model, male C57/BL mice were injected intraperitoneally (ip) with 100 μg phenol-purified LPS (Sigma: *E. Coli* (0127:B8). Control mice, injected with PBS, were sacrificed at time 0 and remaining animals (6/time point) at 0.5, 1, 3, 5, 8, 12 and 24 hours and following LPS injection. In an independent experiment, the effects of activins were neutralized by the pretreatment of mice with the activin binding protein, follistatin, which is able to bind and ablate the effects of activin forms [Nakamura et al., 1990, *Science* 247:836-838]. In this experiment, mice were pretreated ip with human recombinant follistatin 288 (1 μg) 30 minutes prior to an injection of LPS. Mice were sacrificed 30 minutes after the follistatin injection (time 0) and at the same times, relative to LPS, as indicated above. At the time of sacrifice, tissues to be examined for expression levels were placed in ice cold Trizol (Invitrogen Life Technologies) and stored at −80 C for later RNA extraction. Tissues were also placed in formalin prior to transfer to 70% ethanol for later fixation and immunohistochemical studies.

For the acute hepatic inflammation model, male C57/BL6 mice were injected ip with 750 μl/kg BW $CCl_4$ (Sigma). Control mice, injected with PBS, were sacrificed at time 0 and remaining animals were sacrificed at 1, 2, 4, 8, 12, 24, 36, 48 and 72 hours following $CCl_4$ injection. Tissues were collected as described earlier for RNA extraction and immunohistochemical studies.

RNA extractions were performed on 3-5 tissue samples from each time point described above. RNA was extracted using Trizol according to the manufacturer's recommendations. For each sample, approximately 10 μg of RNA was treated with DNAse I (Ambion Inc.) in accordance with the manufacturer's protocol. RNA concentrations for each sample were determined and 1 μg was reverse transcribed to give cDNA using Superscript III reverse transcriptase kit (Invitrogen Life technologies) and using the protocol supplied by the manufacturer. Real time analysis for expression levels were made for the following genes: GAPDH, activin $\beta_A$ subunit, and activin $\beta_B$ subunit. Inhibin α-subunit mRNA expression was also examined using standard thermocycler methods but expression levels were consistently too low to permit quantitative analysis (data not shown).

The specific primers utilized for the real-time quantification of the genes were (5'- to 3'):

```
GAPDH
                                            (SEQ ID NO: 1)
    F tactggcatcttcaccacca (Product 394 bp)

activin β_A
                                            (SEQ ID NO: 2)
    F ggctaacagaaccaggacca (Product 325 bp)

activin β_B
                                            (SEQ ID NO: 3)
    F gacacgcatagccagactca (Product 399 bp)

inhibin α-subunit
                                            (SEQ ID NO: 4)
    F cttatgtattccggccatcc (Product 326 bp)

GAPDH
                                            (SEQ ID NO: 5)
    R gtgagcttcccattcagctc (Product 394 bp)

activin β_A
                                            (SEQ ID NO: 6)
    R cttcttcccatctccatcca (Product 325 bp)

activin β_B
                                            (SEQ ID NO: 7)
    R acttgccctctccaagaaca (Product 399 bp)

inhibin α-subunit
                                            (SEQ ID NO: 8)
    R cctagtgtgggctaccagga (Product 326 bp)
```

The primers were designed specifically for use with the Roche light cycler real-time PCR system. PCR products were isolated and sequenced and BLAST analysis used to confirm they represented the desired gene products. Real time analyses were conducted using Roche SYBR green mastermix (Light cycler Fast start DNA Master SYBR green, Roche Diagnostics GmbH) with conditions optimised for maximal sensitivity. Annealing temperatures for all primers were 60 C. Standards and QCs used throughout the analyses were prepared from pooled cDNA derived from experimental samples in which expression levels of the genes of interest were high. Serial dilutions of the standard cDNA was to cover a 300-fold expression range. Experimental cDNA samples were diluted into the standard curve range and all cDNA was aliquoted and stored at −20. Each sample was analysed for all three gene products of interest, at least twice in independent analytical runs. Between assay QC reproducibility for all gene products gave CVs of <22%.

Immunohistochemistry

Paraffin sections were dewaxed and antigens retrieved by immersing slides in 0.01M citrate buffer, pH 6.0, heating in a microwave (high for 2.5 minutes or 5 minutes for βA or βB respectively, then low for 5 minutes for both), cooling at 4 C for ~20 minutes, and washing in water for 5 minutes. Endogenous peroxidase was blocked in 3% $H_2O_2$ for 10 minutes, and slides blocked for 1 hour (10% normal rabbit serum+CAS block, Zymed Laboratories Inc., CA, #00-8120) for activin βA or 20% normal goat serum/0.1% Tween 20 in Tris-buffered saline (TBS) for 1 hour for activin βB. The blocking solution was tapped off and the sections were incubated with antibodies specific for the activin βA-subunit (E4, 10 μg/ml in 1% bovine serum albumin (BSA)/TBS, Oxford Brookes University) or activin βB subunit (2 μg/ml diluted in blocking solution, Jones et al. 2000) overnight at 4 C. After washing, the activin βA slides were incubated in rabbit anti-mouse $IgG_{2b}$-HRP (Zymed, #61-0320) diluted 1:500 for 2 hours and washed twice in Tris-buffered NaCl (TBS) 0.05% Tween-20 pH 7.5, then MilliQ $H_2O$. Reaction product was developed with 3,3'-diaminobenzidine tetrahydrochloride (DAB) substrate kit (Zymed #00-2014), and sections counterstained in hematoxylin for 15 seconds. All wash steps were in TBS/0.05% Tween-20. For the activin βB slides, the sections were washed and then incubated with Dako Envision HRP (rabbit, #K4003) for 1 hour at room temperature. The sections were washed again in TBS/Tween and the reaction product was developed with DAB, followed by counterstaining as for activin βA. Negative control sections were incubated with purified mouse myeloma IgG2B protein (Zymed #02-6300) instead of the activin βA-specific antibody or non-immunized rabbit IgG (Dako #X0903) instead of the activin βB-specific antibody.

Data Analysis

For each sample, activin βA and βB mRNA expression levels were expressed relative to the GAPDH expression level for that sample. Thereafter, all time 0 data were normalized to 1 and data at subsequent time points was expressed relative to that time point. All data are depicted as mean±SEM values. Values were typically derived from the 3 tissue samples assessed per time point, but more samples were assessed in controls and at some early time points.

Results

Figure 6:
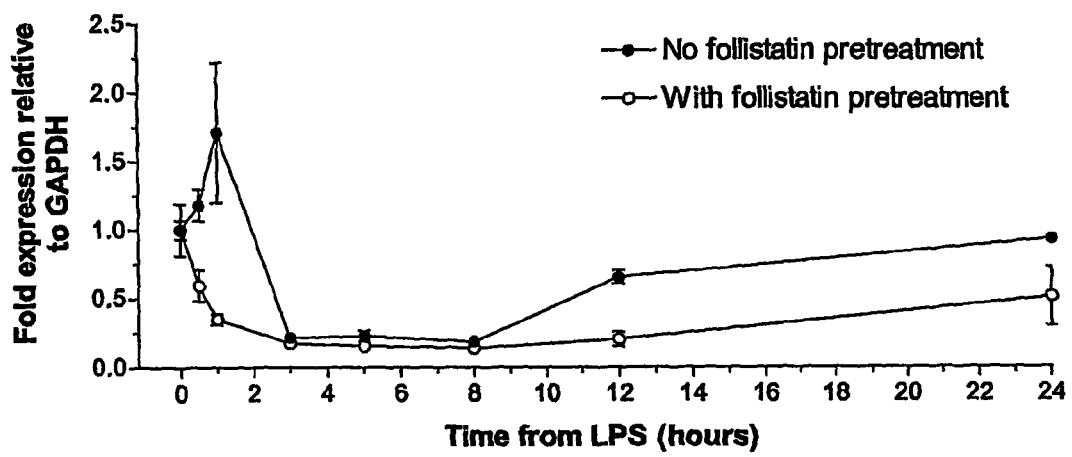
FIG. 6 is a graphical representation of quantitative mRNA levels for activin $\beta_A$ (upper panel) and βB (lower panel) subunits in livers of mice challenged with a single intraperitoneal injection of LPS. Mice were either treated with LPS alone (no follistatin pretreatment, solid circles) or 1 µg of human recombinant follistatin 288 thirty minutes before LPS (follistatin pretreatment, open circles). Data are represented as mean±SEM at each timepoint assessed relative to LPS, with expression levels expressed relative to the expression of the housekeeping gene, GADPH. All time 0 data were normalized to a value of 1 and data at subsequent time points were expressed relative to that time point.
Figure 6:
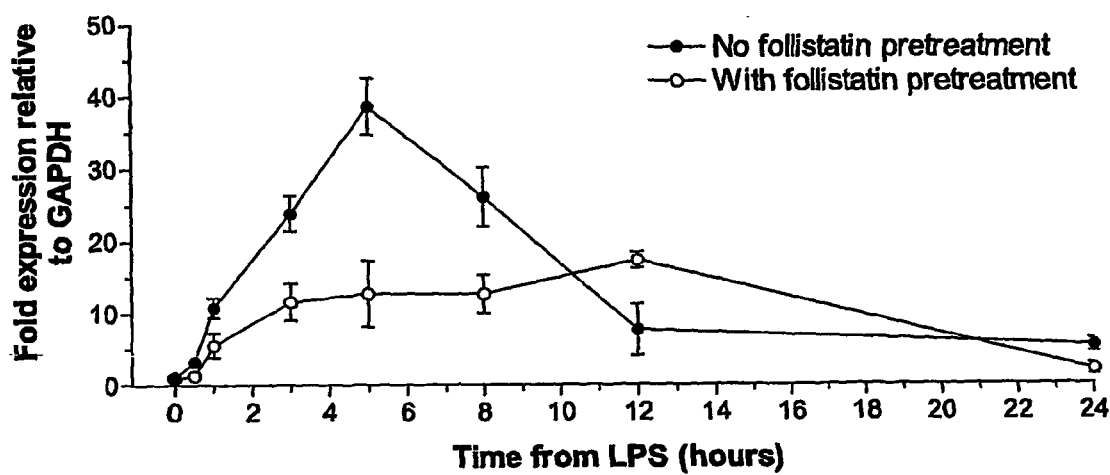

In a mouse model of acute systemic inflammation following challenge with LPS, liver mRNA levels for the activin βA and βB subunits were examined. Activin βA subunit mRNA showed a minor increase (<2-fold control levels) in expression level 1 hour after LPS, but between 1 and 3 hours expression levels fell markedly and from 3 to 8 hours a clear suppression (to <25% of control levels) was evident (FIG. 6, upper panel). By 12 hours, expression was approaching control levels and by 24 hours had returned to pretreatment levels. Treatment with the activin binding protein and antagonist, follistatin, resulted in an immediate suppression in activin βA subunit mRNA levels.

In contrast, liver βB subunit mRNA levels displayed a completely different profile to the activin βA subunit, rising immediately after LPS to reach a maximal expression level at 5 hours, at which time, expression averaged over 35-fold control levels (FIG. 6, lower panel). Between 5 and 12 hours this expression fell progressively but at 12 hours, expression was still elevated (on average, 7-fold control levels). At 24 hours after LPS treatment, activin βB mRNA levels were still ~5-fold above control levels. As for activin βA subunit expression, activin βB subunit expression patterns were altered by the follistatin pretreatment, with clear suppression of the LPS-associated effects on βB subunit expression.

Figure 7:
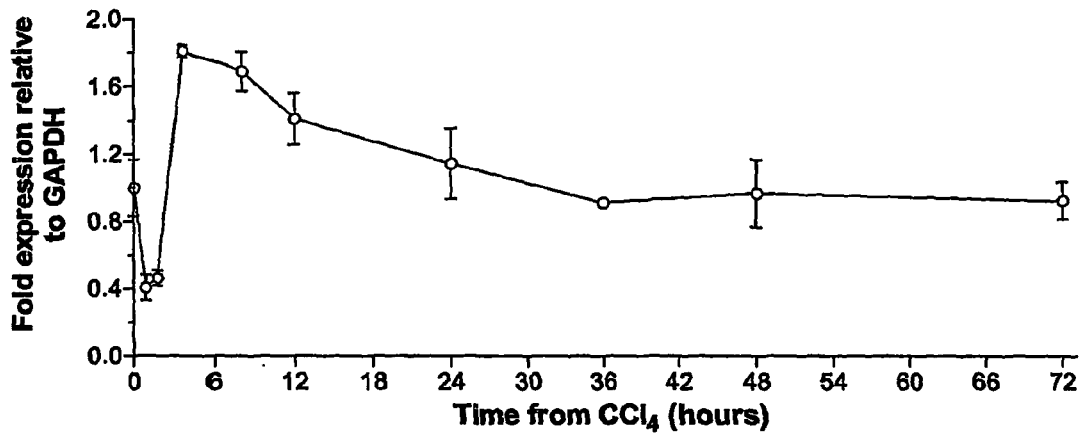
FIG. 7 is a graphical representation of quantitative mRNA levels for activin $\beta_A$ (upper panel) and βB (lower panel) subunits in livers of mice challenged with a single intraperitoneal injection of $CCl_4$. Data are represented as mean±SEM at each timepoint assessed relative to $CCl_4$, with expression levels expressed relative to the expression of the housekeeping gene, GADPH. All time 0 data were normalized to a value of 1 and data at subsequent time points were expressed relative to that time point.
Figure 7:
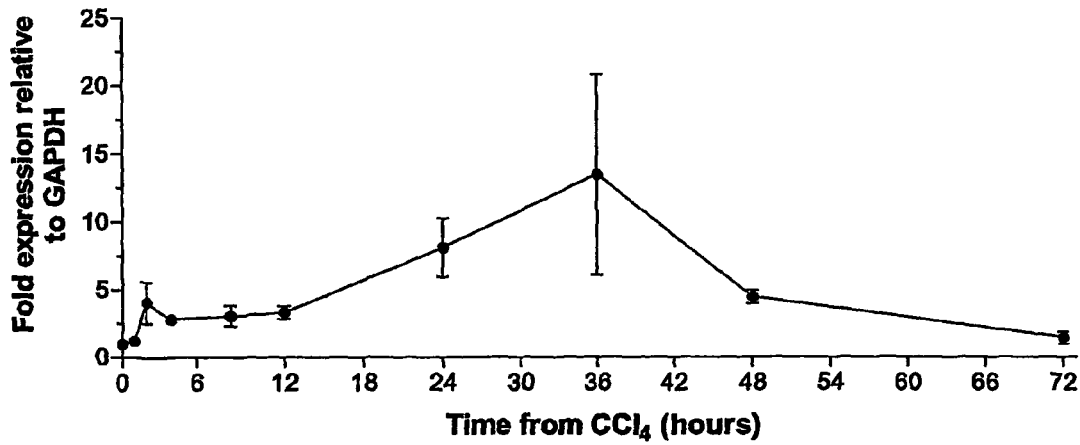

In the acute hepatic inflammation model following challenge with $CCl_4$, activin βA subunit expression fell slightly following $CCl_4$ treatment (FIG. 7, upper panel), such that at 1 and 2 hours, average expression levels were only 40-50% of control levels. In contrast, by 4 hours after injection, average βA mRNA was moderately (80%) elevated and then declined to around pre-treatment levels by 36 hours. In contrast to the activin βA subunit, activin βB showed the greatest changes in expression at 24 and 36 hours after $CCl_4$ injection, with a 13.5-fold increase above control levels (FIG. 7, lower panel).

In both inflammatory models, expression of the inhibin α-subunit was examined but expression levels were consistently too low to permit quantitative analysis. Therefore it is unlikely that the profound changes in activin βB subunit mRNA resulted in the formation of elevated inhibin dimers (an α-βB dimer or inhibin B), but dimerized to form activin B (a dimer of βB-βB). Given the only marginal changes in activin βA mRNA, it is relatively unlikely that the increased βB mRNA expression resulted in significant formation of the heterodimer, activin AB (βA-βB).

Figure 8:
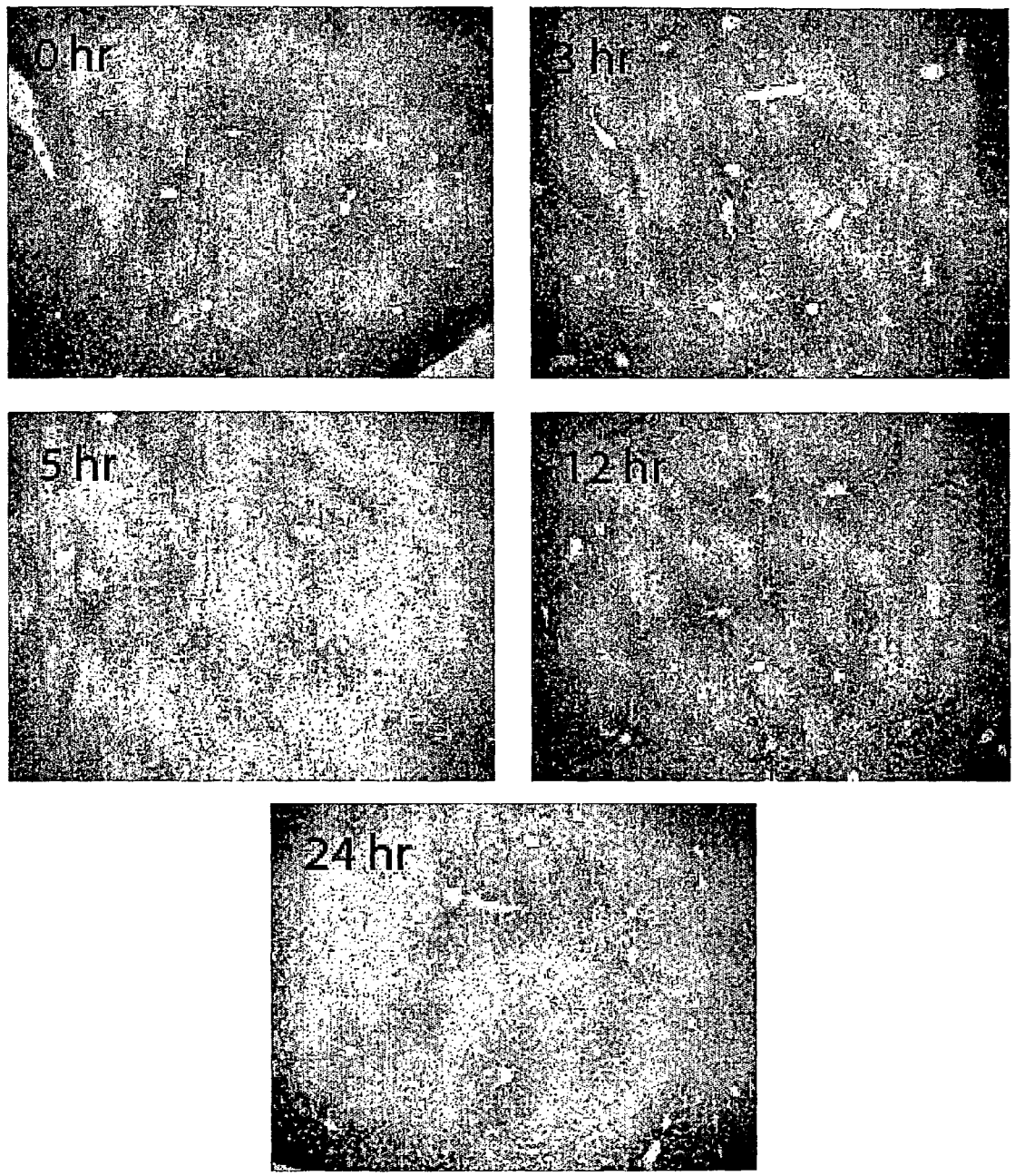
FIG. 8 is an image of the immunolocalization of the activin $\beta_A$ subunit in livers of mice at various timepoints following LPS treatment. The activin $\beta_A$ subunit was localized to hepatocytes in untreated animals (t=0 hr) but predominantly around the central hepatic veins. Immunolocalization appeared diminished at 5 hours following LPS challenge, but returned to pre-treatment localization patterns by 12 hours (X 50).
Figure 9:
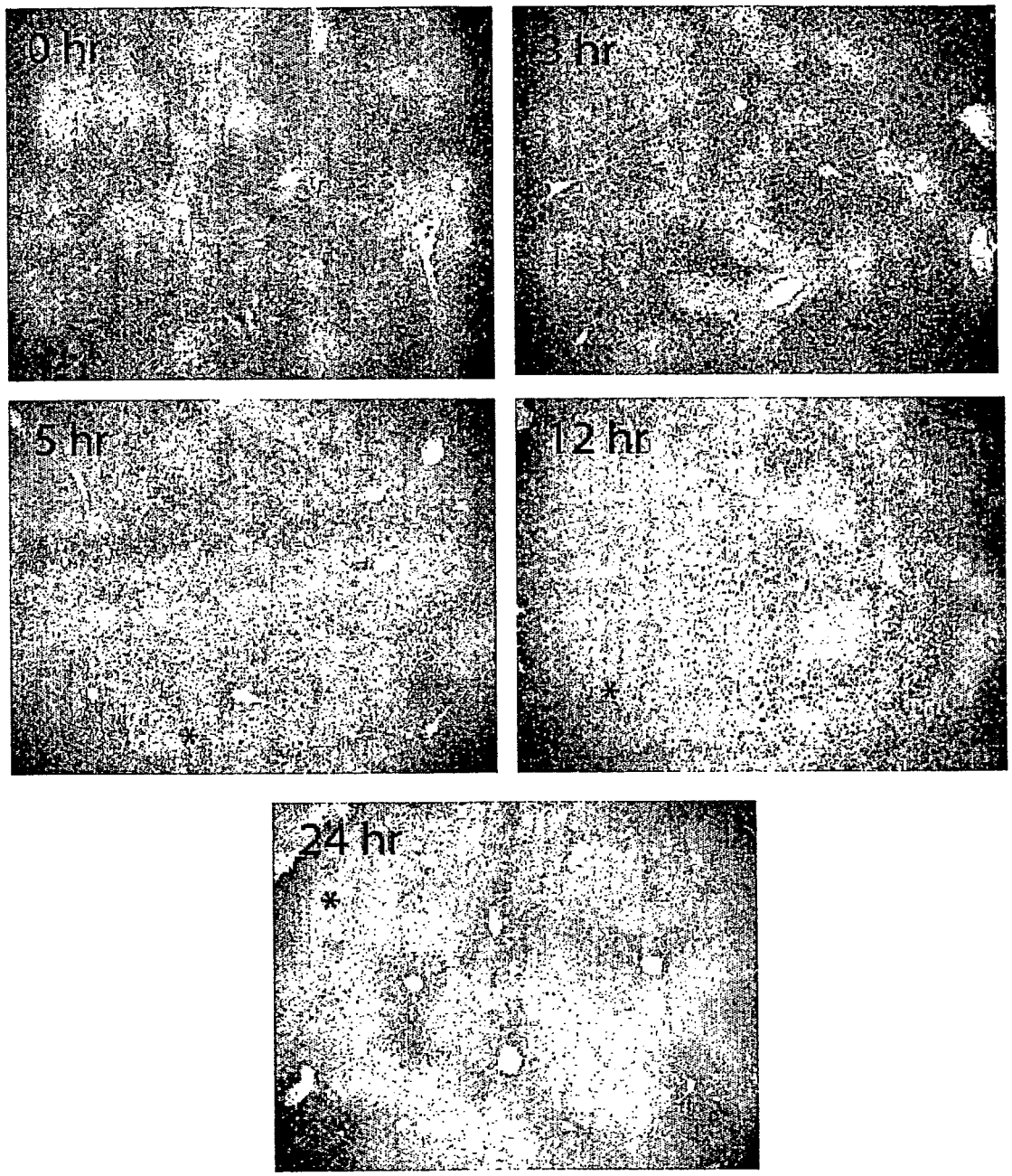
FIG. 9 is an image of the immunolocalization of the activin βB subunit in livers of mice at various timepoints following LPS treatment. The activin βB subunit was localized to hepatocytes in untreated animals (t=0 hr), in areas surrounding portal tracts but not central veins. Immunolocalization appeared diminished at 5 hours following LPS challenge, but returned to pre-treatment localization patterns by 12 hours. Note also the loss of localization in peripheral hepatocytes (asterisks) (X 50).
Figure 10:
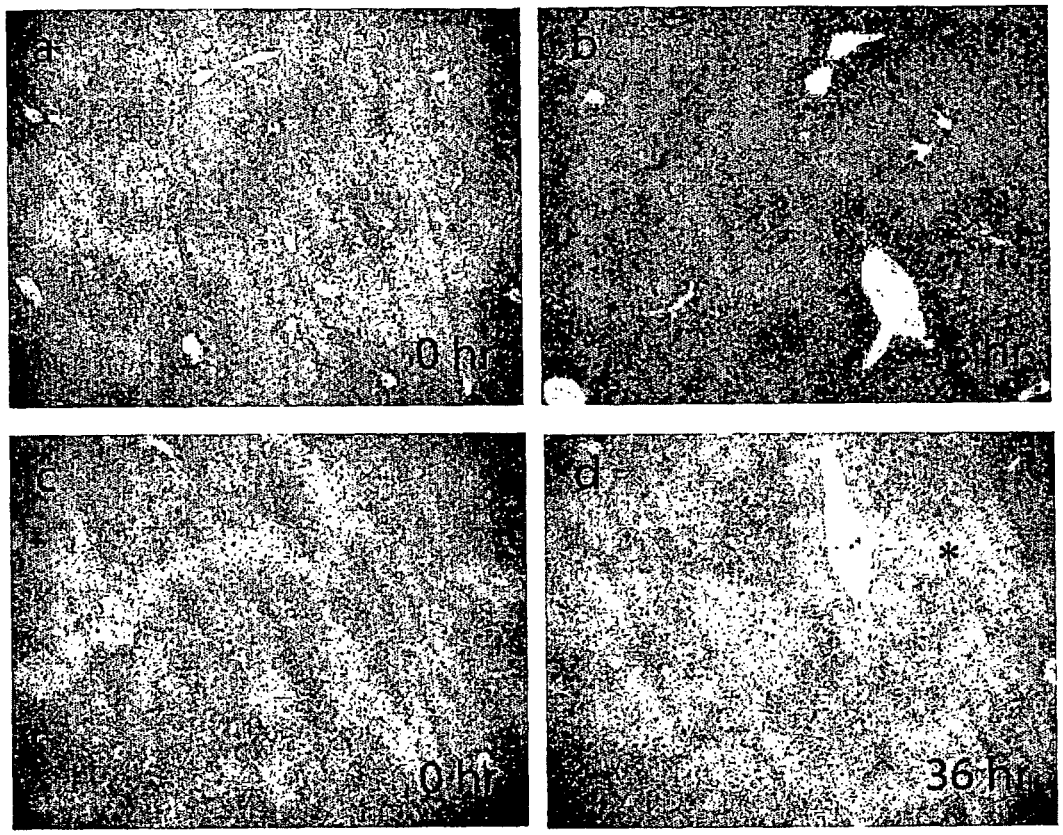
FIG. 10 is an image of the immunolocalization of the activin $\beta_A$ subunit (panels a and b) and activin βB subunit (panels c and d) in livers of mice at 0 or 36 hours following $CCl_4$ challenge. As for LPS treatment, the activin βB subunit was localized to areas surrounding the portal tract but not central veins whereas the activin $\beta_A$ subunit predominantly localized to hepatocytes surrounding central veins. Note also the localization of activin $\beta_A$ subunit at the 36 hour timepoint in areas of hepatocyte apoptosis/necrosis, while localization for the activin $\beta_B$ subunit is absent from these areas (asterisks) (X50).

Using antibodies specific for the activin βA and βB subunits, the liver immunolocalization was investigated in both the acute systemic model of LPS challenge and the acute hepatic inflammatory model using $CCl_4$. Localization of the activin βA subunit in normal liver was in hepatocytes and more specifically those predominantly around the central veins (FIG. 8). Following LPS challenge, the localization appeared to diminish around 5 hours after LPS and returned to a pre-treatment distribution by 12 hours. For the activin βB subunit, however, localization was most evident in hepatocytes surrounding the portal tract areas of the liver and less so around the central veins (FIG. 9). However, the localization appeared to diminish at 5 hours following LPS and returned to pre-treatment patterns by 12 hours. There also appeared to be a loss of hepatocyte localization in peripheral areas of the liver (FIG. 9). In the $CCl_4$ model of acute hepatic inflammation, subunits localized to the hepatocytes surrounding the central vein and portal tracts for the βA and βB subunits respectively (FIG. 10a and 10b). However, 36 hours after $CCl_4$ treatment, there appeared to be localization for the activin βA subunit (FIG. 10c) in hepatocytes that were destined to become apoptotic/necrotic, whereas there was no or little localization for the activin βB subunit in these areas (FIG. 10d).

Example 8

Activin and Follistatin are Elevated in Patients with Severe Traumatic Brain Injury Background Traumatic Brain Injury (TBI) is one of the major causes of morbidity and mortality in young adults (Van Baalen et al., 2003, *Disability and Rehabilitation* 25 9-18). Activation of various immunological pathways occurs subsequent to the TBI, including the release of various cytokines, activation of brain glial cells and various cellular and tissue injury responses. A number of inflammatory-responsive cytokines have been detected in the serum and cerebrospinal fluid (CSF) of TBI patients, arising from the post-traumatic inflammatory response. The measurement of activin A and its binding protein, follistatin, has not been determined in this setting and was the purpose of this study. These results show that both proteins and, particularly activin, are responsive and elevated in the CSF of patients with TBI. As a consequence, these findings provide new scope for novel diagnostic and therapeutic opportunities based around this component of the inflammatory response initiated by TBI.

Materials and Methods

Patients were admitted to The Alfred Hospital, Melbourne, following TBI due largely to motor vehicle accidents. The six patients assessed in this subset of a larger study were all male, and had ages ranging from 16-50 years. They had a Glascow Coma Score (GCS) of 3-7 upon admittance to the Alfred Emergency Department. In most cases, paired serum and CSF samples from these patients were obtained following ethical consent being signed by a next-of-kin. The samples were collected daily relative to the TBI. Samples were centrifuged at 170 g for 10 minutes, aliquoted and frozen until analysis.

Serum activin A concentrations were determined as previously described using an enzyme-linked immunosorbent assay (ELISA) (Knight et al. 1996, supra). The assay measures 'total' activin A, that is both free and bound components. The assay standard was human recombinant activin A (National Hormone and Pituitary Program (NHPP), Torrance, Calif., USA). The mean assay sensitivity was 0.01 ng/ml, and the mean intra- and inter-assay coefficients of variation (CV's) were both <9%.

Follistatin concentrations in serum were measured with a radioimmunoassay validated for human follistatin as previously described (O'Connor et al. 1999, supra), which also measures both free and bound forms. The standard employed was human recombinant follistatin 288, the assay sensitivity was 2.0 ng/ml and the intra- and interassay coefficients of variation were both <4.9%.

For CSF samples, the activin and follistatin assays were as described above. However, the standard diluent used was 0.05% BSA in PBS to match the protein concentration in the samples. A 20% solution of BSA in PBS (25 µL) was added to the wells in the activin A ELISA before the addition of CSF samples, as this was found to enhance the reproducibility of the assays.

Results

Figure 11:
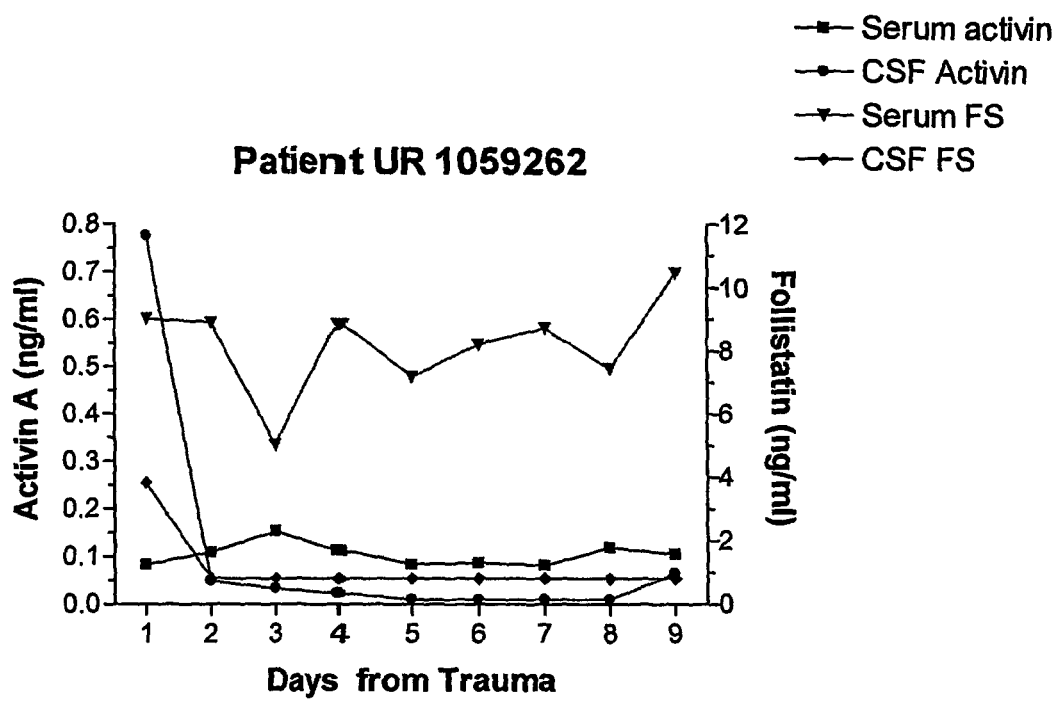
FIG. 11 is a graphical representation of the serum and cerebrospinal fluid (CSF) concentrations of activin A and follistatin in head trauma patients (Panels A-E) taken at various days following the incidence of trauma.
Figure 11:
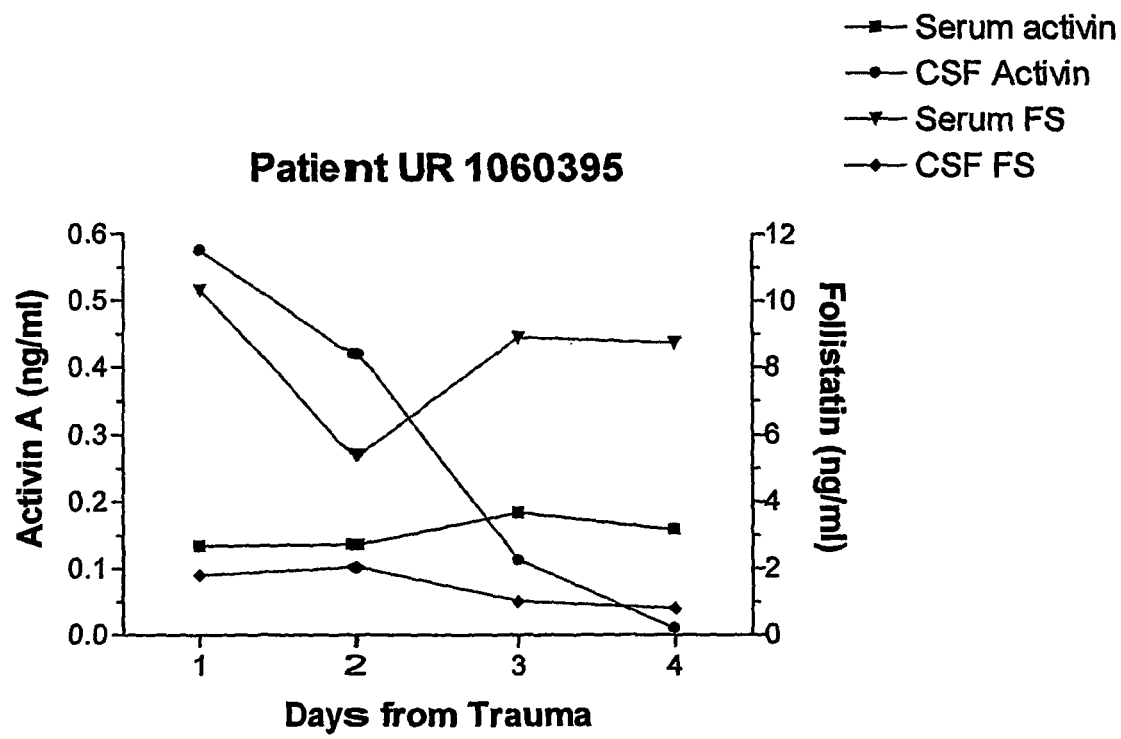
Figure 11:
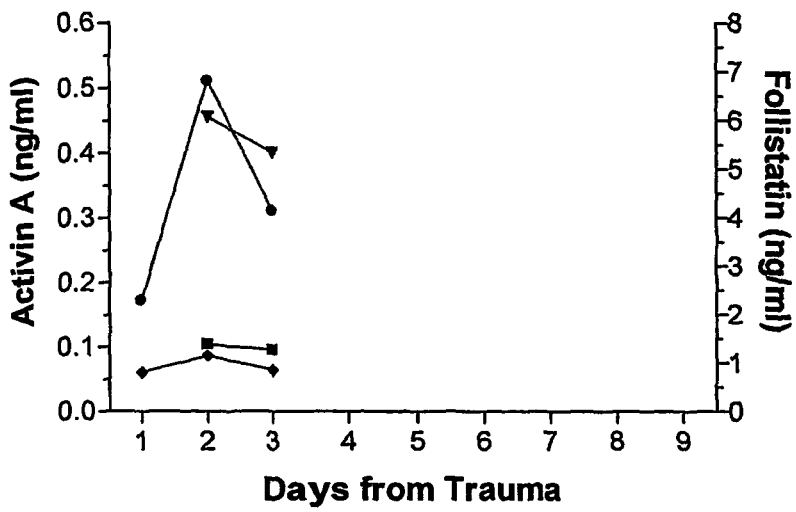
Figure 11:
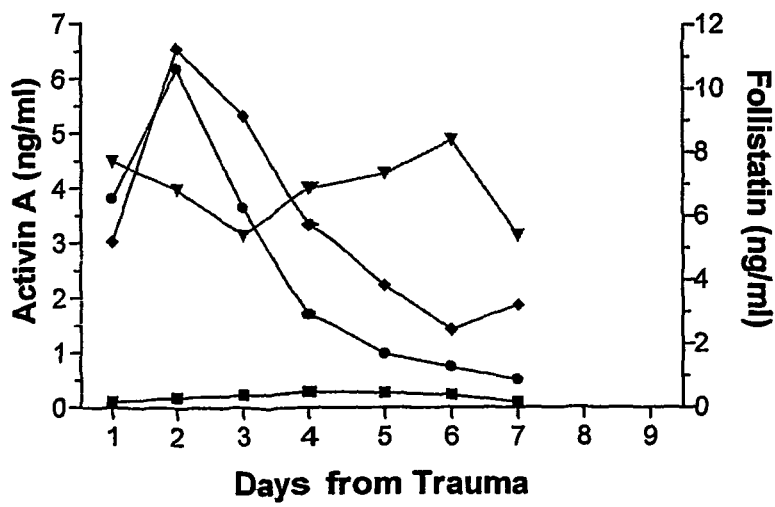
Figure 11:
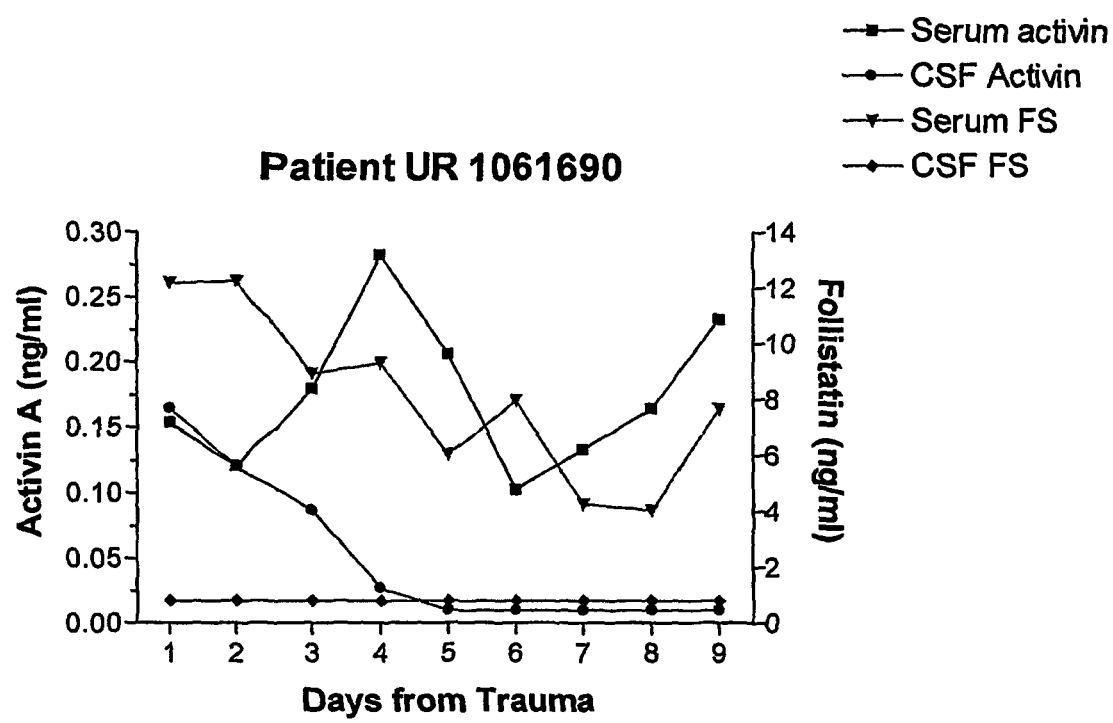
Figure 12:
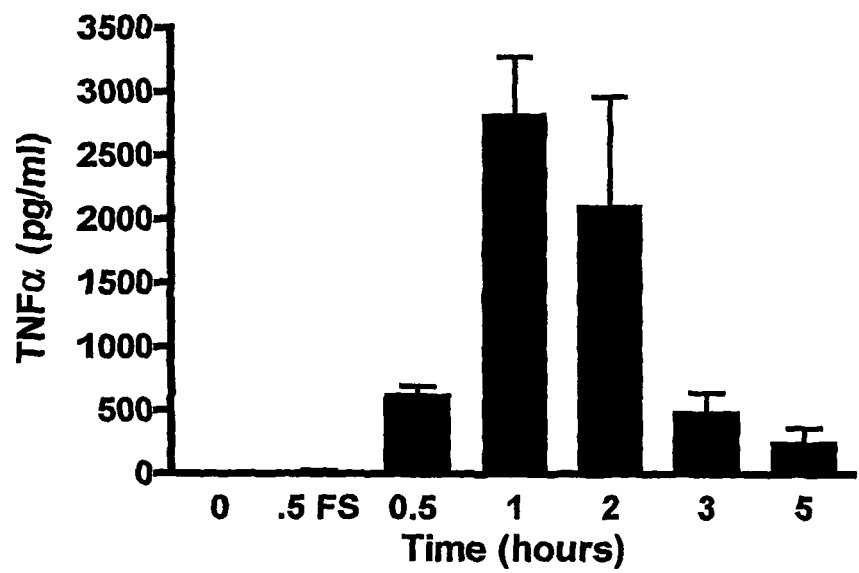
FIG. 12 is a graphical representation of the cytokine release in mice administered 0.5 µg of follistatin prior to LPS.
Figure 12:
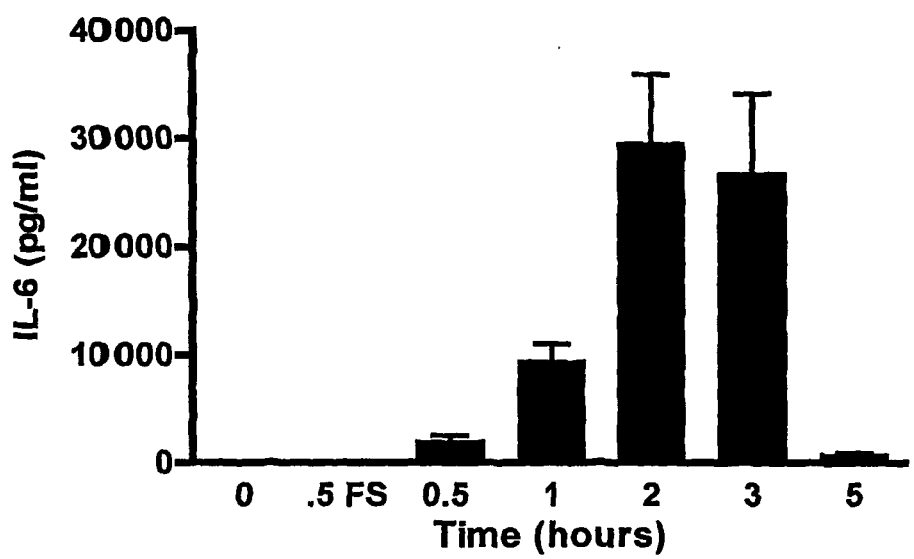
Figure 13:
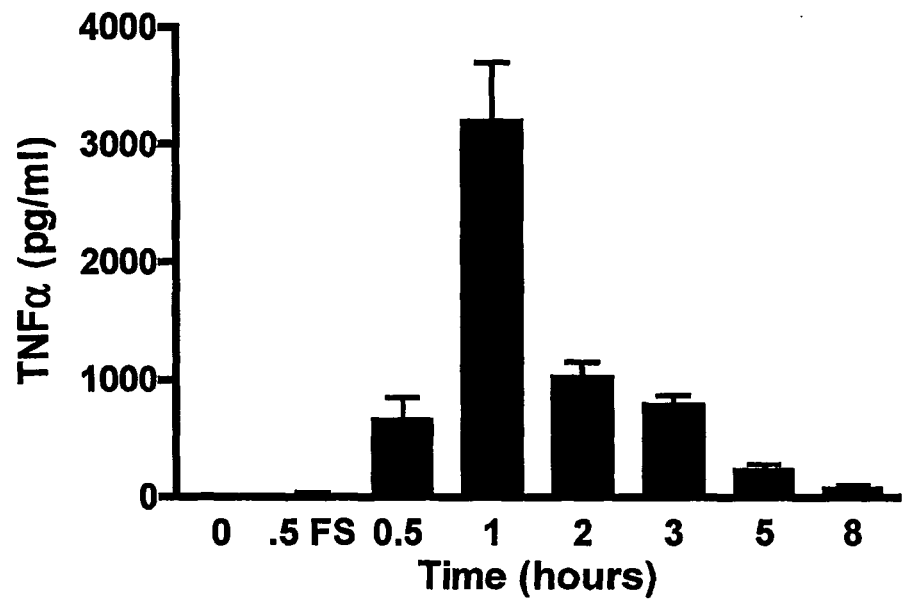
FIG. 13 is a graphical representation of the cytokine release in mice administered 2 µg of follistatin prior to LPS.
Figure 13:
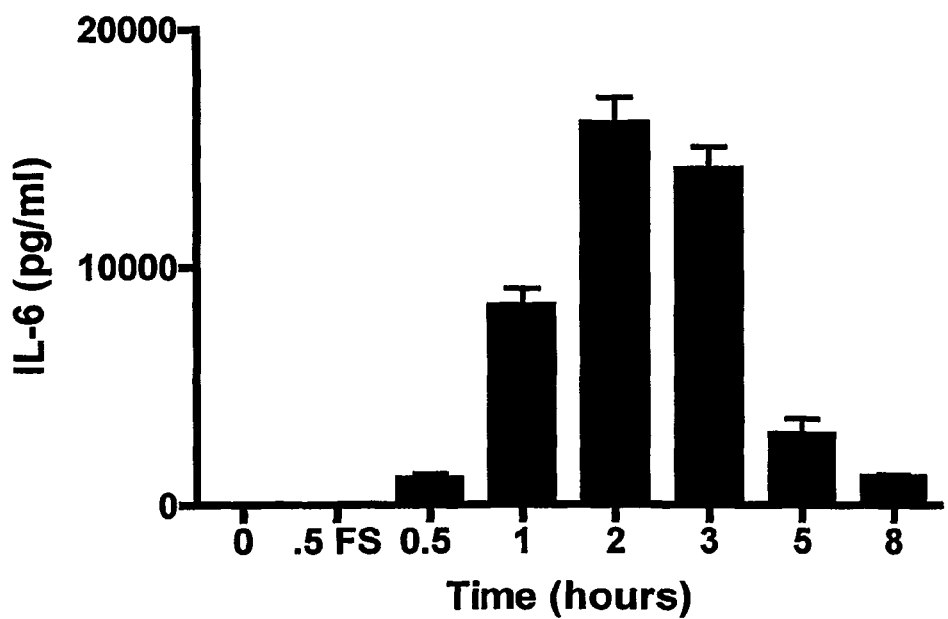
Figure 14:
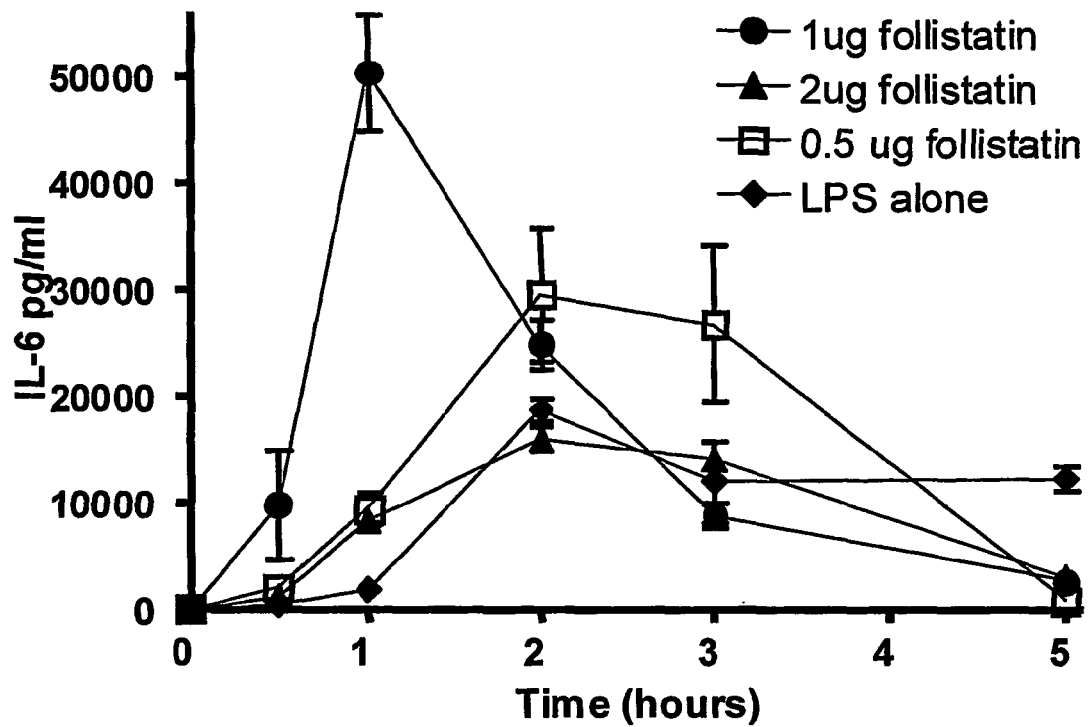
FIG. 14 is a graphical representation of the IL-6 release in mice administered 0-2 µg of follistatin prior to LPS.
Figure 15A:
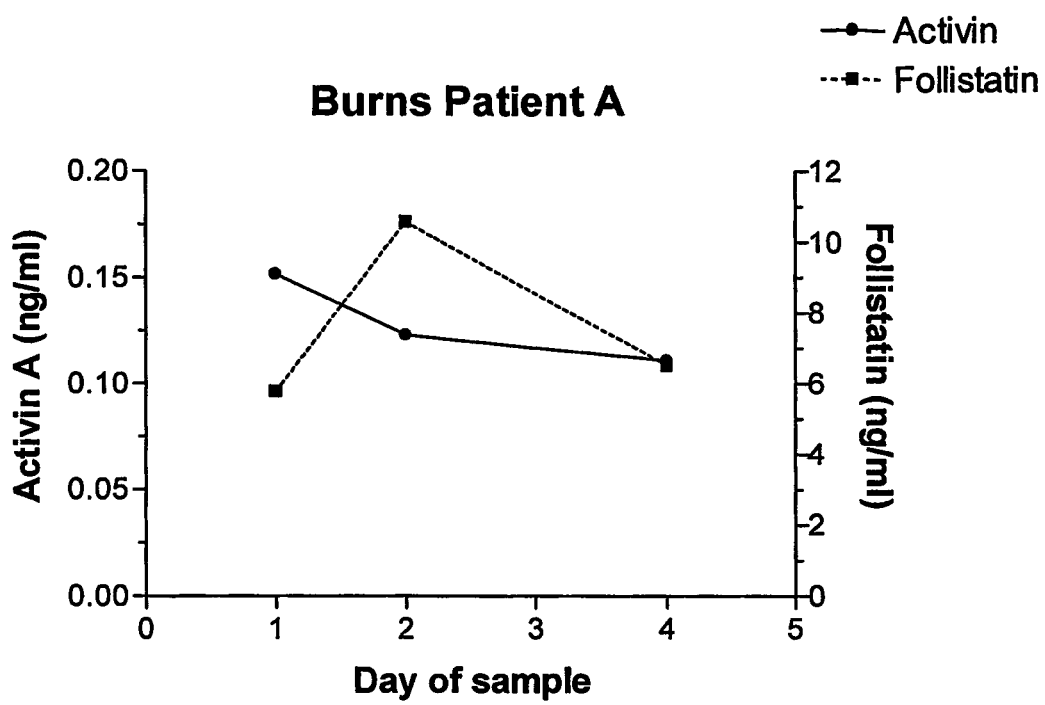
FIG. 15 is a graphical representation of plasma activin A and follistatin concentrations in four patients (Panels A-D) with moderate burns injury. The day of sampling relates to the first day in which a sample was taken and not necessarily relative to the day of burns injury.
Figure 15B:
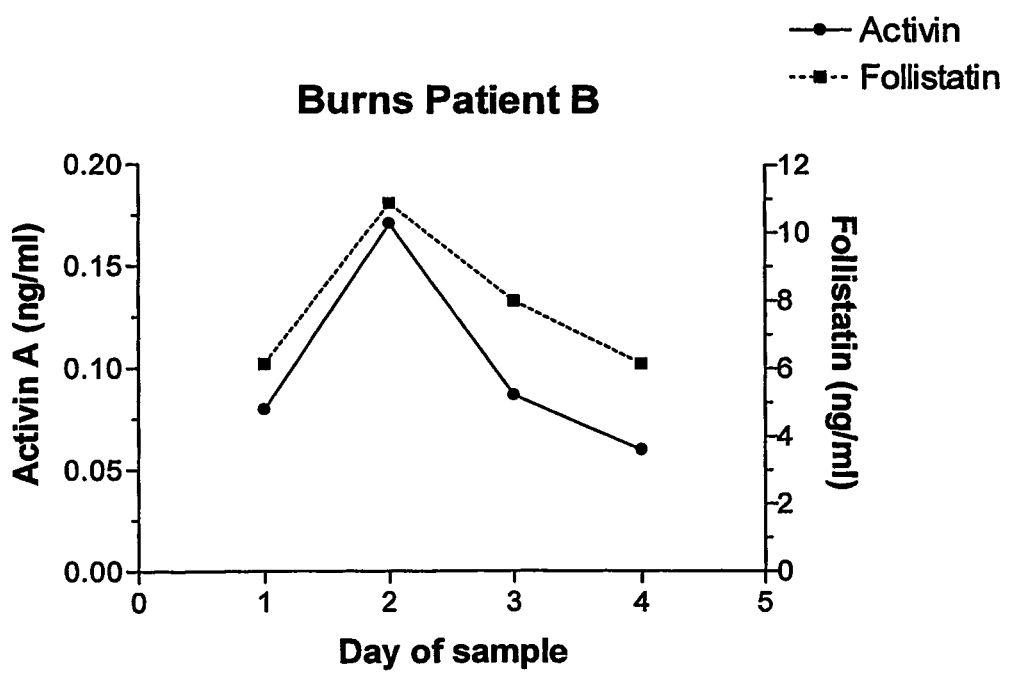
Figure 15C:
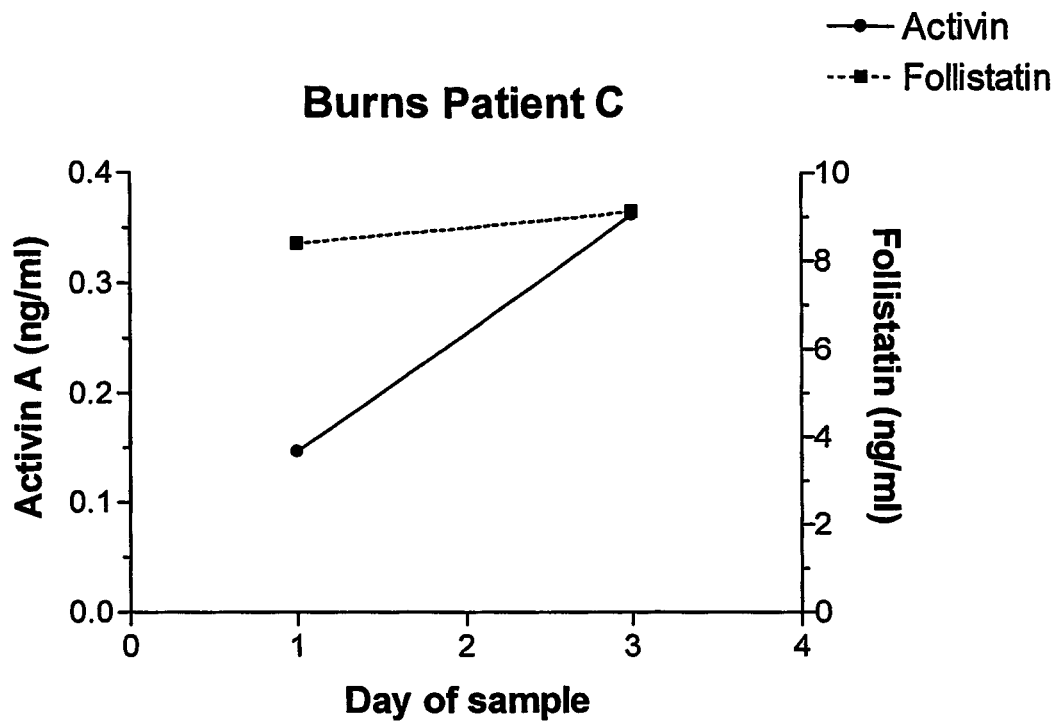
Figure 15D:
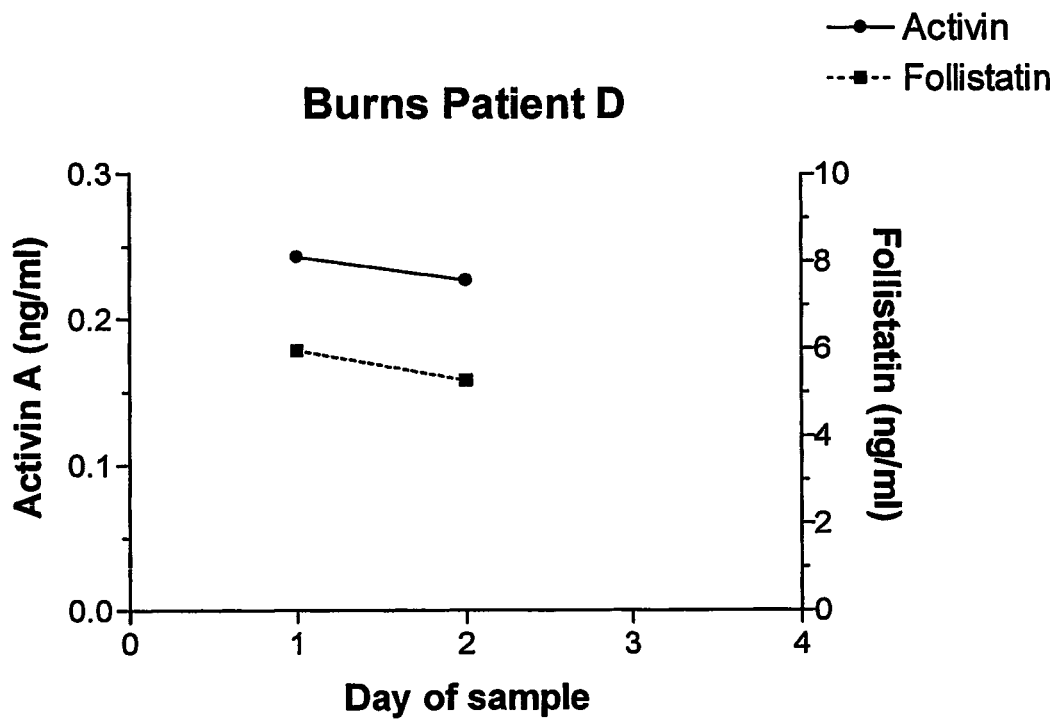

Analysis of this set of TBI patients showed that concentrations of activin were elevated following TBI (FIG. 11). This was particularly the case for activin A in the CSF. The temporal pattern and the levels of activin in the CSF varied slightly for each patient, but in general the levels were highest in an individual patient 1-2 days after the TBI incident. For follistatin, there was in some of the patients a minor increase in serum or CSF levels, but not to the extent seen for CSF activin. As the CSF activin concentrations showed an elevation following TBI, this likely reflects activation of inflammatory pathways within the Central Nervous System (CNS) and particularly the brain, and suggests the trauma and inflammation is largely confined to this organ and not part of a systemic inflammatory response.

Example 9

The Role of Activin and Follistatin in Lipopolysaccharide Induced Cytokine Release Background Activin A is released in response to the administration of lipopolysaccharide (LPS) in mice. This release occurs early in the ensuing cytokine cascade and appears to precede the release of the key pro-inflammatory cytokines tumor necrosis factor-α (TNFα) and interleukin-6 (IL-6). When the activin antagonist, follistatin, was administered prior to injection of LPS, the release of these cytokines was altered. This indicated that activin has a role in modulating the release of these cytokines as part of the inflammatory response and that follistatin could be used as a therapeutic adjuvant to modify cytokine release during inflammatory disease.

Methods

The methods employed for the following experiments are the same as those described in Example 1 with the exception that two different doses of follistatin were used to identify dose dependent effects on the activity of activin in the modulation of cytokine release in an LPS induced inflammatory response. The two doses used following the Exampled 1 experiment, which used 1 µg of follistatin, were 2 µg and 0.5 µg.

Results

Activin and follistatin release profile do not change significantly between doses of 0.5 µg, 1 µg or 2 µg of follistatin prior to LPS stimulation. The level of suppression of TNF release as the same following three separate doses of follistatin (0.5, 1 and 2 µg) prior to administration of LPS. The release of IL-6 increases approximately 250% in mice administered 1 µg of follistatin prior to LPS as compared to the increase observed in mice administered LPS alone. However, IL-6 release is only increased by 50% in mice administered 0.5 µg of follistatin prior to LPS. The release of IL-6 in mice administered 2 µg of follistatin prior to LPS is the same as that observed in mice injected with LPS alone.

Conclusions

The release of TNFα was similar following the administration of the 0.5, 1 and 2 µg dose of follistatin. (FIGS. 12, 13 and 2A and 2B).

IL-6 release in mice administered 1 µg of follistatin prior to LPS increased (≈50000 pg/ml) as compared to the release of IL-6 in mice that were administered LPS alone (≈20000 pg/ml). When the dose of follistatin was doubled to 2 µg, the release of IL-6 did not increase. Rather it actually decreased back to the levels observed in mice administered LPS alone (≈20000 pg/ml). However, in mice administered 0.5 µg of follistatin prior to LPS administration, IL-6 release increased (≈30000 pg/ml) to levels above that observed in mice administered LPS but did not increase to the same extent as observed in mice administered 1 µg of follistatin prior to LPS. This demonstrates an effect of follistatin on the modulation of cytokine release by activin in a dose dependant manner up to a dose of 1 µg/mouse with the higher dose of 2 micrograms leading to a suppression to levels found in mice given LPS alone. The dose of follistatin used to modulate the cytokine response is a critical component of any therapeutic application.

It appears that the dose of follistatin required to block the ability of activin to modulate TNFα release is not as high as that required to modulate IL-6 release. This may be related to the different temporal release patterns of TNFα and IL-6, with TNFα being release earlier than IL-6 and therefore potentially more sensitive to the presence of an early stimulatory factor in the inflammatory response such as activin.

Example 10

Activin and Follistatin are Expressed During the Healing Process of Burns

Background

Burns represent a serious injury with their severity dependent on the surface area of the body affected by the burn as well as the depth of the burn, namely partial or full thickness. Minor burns produce a local injury with a local inflammatory response followed by a process of healing. The latter can restore the skin to its pre-burn condition or may result in a scar due to a fibrotic process involving deposition of collagen.

In more serious burns, there occurs a profound inflammatory response involving the transudation of fluid as well the death of tissue from the thermal injury. There can be profound changes in fluid balance leading to shock and death. During the healing process, with large burns, there is insufficient skin for grafting purposes leaving open surfaces susceptible to infection and inflammation. Often the inflammation leads to fibrotic processes that result in deposition of collagen and severe scarring.

The present example analysis levels of activin A and follistatin in the circulation of patients with burns. Also studied are the local expression of activin A and follistatin in biopsies taken from patients with burns at different stages of healing.

Material and Methods

The levels of activin A and follistatin were measured in serum samples from 4 patients with burns at different stages after the thermal injury. Additionally, tissue samples taken from the area of injury in patients (n=3) with burns as part of their routine management at the Alfred Hospital Burns Unit were examined by light microscopy using sections stained by haematoxylin and eosin as well as by immunocytochemistry to determine the expression of activin A and follistatin.

Serum activin A concentrations were determined as previously described using an enzyme-linked immunosorbent assay (ELISA) (Knight et al. 1996, supra). The assay measures 'total' activin A, that is both free and bound components. The assay standard was human recombinant activin A from Biotech Australia (Robertson et al. 1992). The mean assay sensitivity was 0.01 ng/ml, and the mean intra- and inter-assay coefficients of variation (CV's) were both <9%.

Follistatin concentrations in serum were measured with a radioimmunoassay validated for human follistatin as previously described (O'Connor et al. 1999, supra), which also measures both free and bound forms. The standard employed and that used as the tracer was human recombinant follistatin 288 (National Hormone and Pituitary Program (NHPP), Torrance, Calif., USA), the assay sensitivity was 2.0 ng/ml and the intra- and interassay coefficients of variation were both <4.9%.

For the immunolocalisation of tissue sections for activin and follistatin, paraffin sections were dewaxed and antigens retrieved by immersing slides in 0.01M citrate buffer, pH 6.0, heating in a microwave (high for 2.5 minutes, low for 5 minutes), cooling at 4° C. for ~20 minutes, and washing in water for 5 minutes. Endogenous peroxidase was blocked in 3% $H_2O_2$, and slides blocked for 1 hour (CAS block, Zymed Laboratories Inc., CA, #00-8120). Sections were incubated in activin $\beta_A$-(E4, $IgG2_b$) or follistatin-specific (2E6) antibody (IgM) at 10 µg/ml overnight at 4° C. After washing, slides were incubated in anti-mouse $IgG_{2b}$-HRP (Zymed, #61-0320) or IgM-HRP (Zymed #61-6820) diluted 1:500, for 2 hours, and washed twice in Tris-buffered NaCl (TBS) 0.05% Tween-20 pH 7.5, then MilliQ $H_2O$. Reaction product was developed with 3,3'-diaminobenzidine tetrahydrochloride substrate kit (Zymed #00-2014), and sections counterstained in haematoxylin for 15 seconds. All wash steps were in TBS/0.05% Tween-20. Antibodies were diluted in 1% BSA/TBS.

Results

In the four patients (FIG. 15, panels A-D), the levels of activin A and follistatin varied showing peaks as in figure B and very high levels were seen in one of the patients (panel D). In the latter patient the levels are very significantly elevated above those seen and reach levels seen in patients with septicaemia (Michel et al., 2003, *European Journal of Endocrinology* 148: 559-564). From these preliminary studies it is concluded that the levels of activin A and follistatin in serum may vary significantly during the course of an injury due to burns and in some patients the levels reach those found in patients with septicaemia. These studies are consistent with the concept that the inflammatory response associated with burns initiates increased activin A levels which in turn stimulate follistatin similar to examples given of the changes in these levels in mice given an LPS challenge.

Sites of expression of activin A and follistatin in tissue samples taken from the burned areas at different time points after the injury demonstrate that a variety of cell types are capable of producing these proteins.

Figure 16:
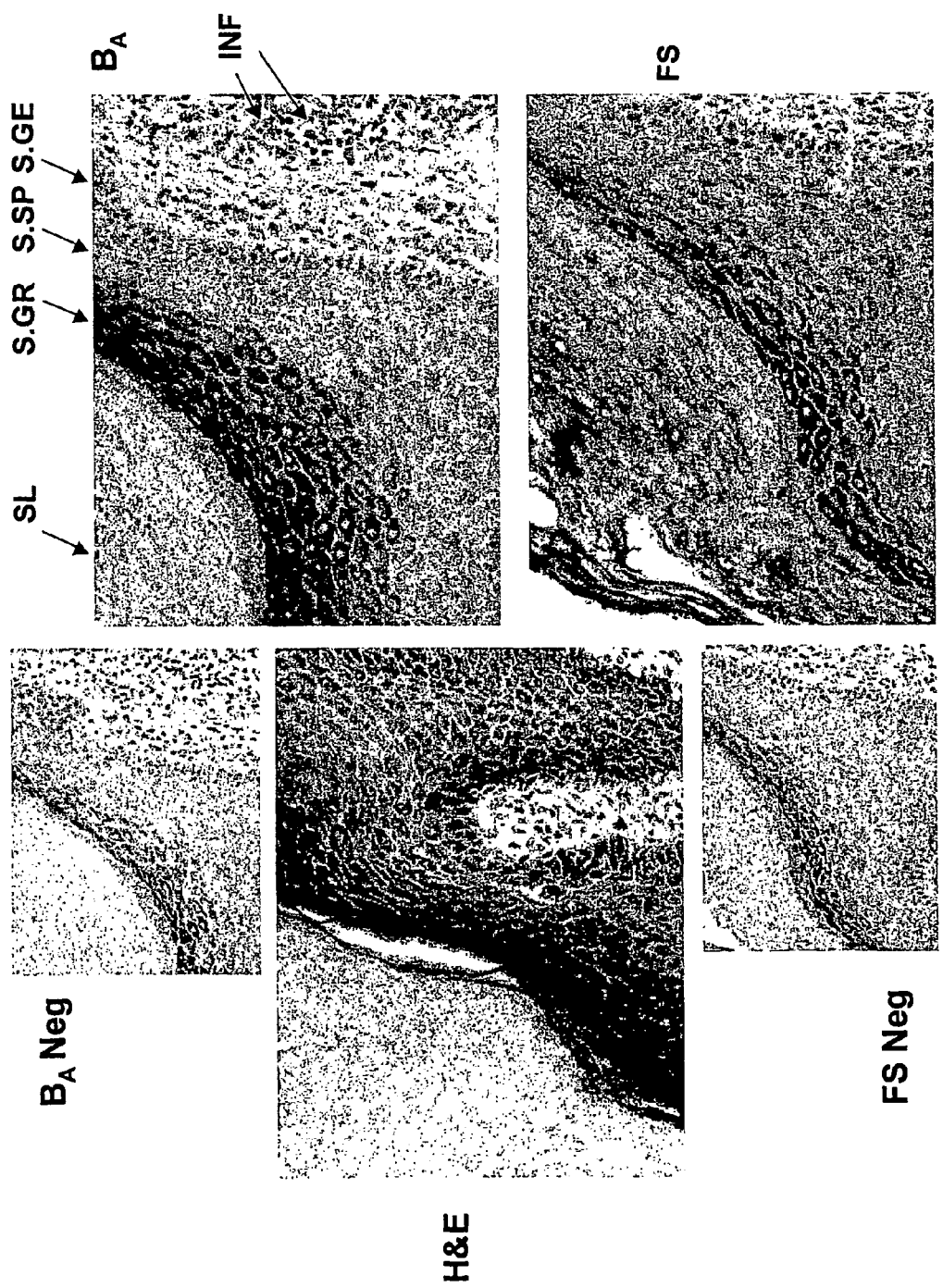
FIG. 16 is an image of skin showing immunocytochemistry of the immunocytochemistry of activin A ($\beta_A$) and follistatin (FS) is shown by brown colour. H&E represents a section stained by haematoxylin and eosin (H&E). SL=stratum lucidum; SGR=stratum granulosum; SSp=stratum spinosum; SGE=stratum germinativum; INF=inflammatory cells.
Figure 17:
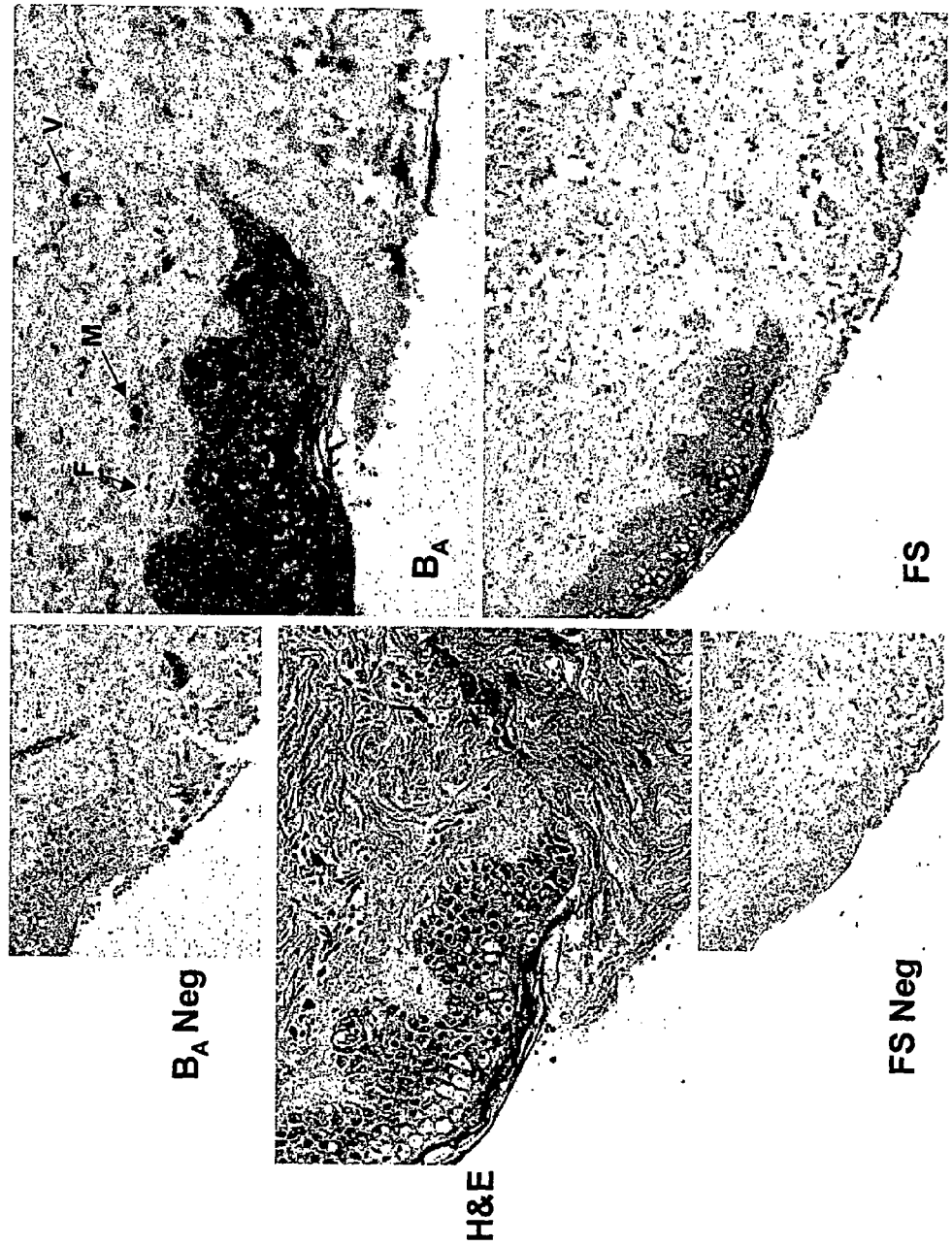
FIG. 17 is an image of a section showing epithelialised and bare areas of burn showing marked dermal fibrosis with fibroblast, macrophage and blood vessels marked by arrows. The brown colour product denotes activin or follistatin positivity.

Expression of activin A is detected by the localisation of the $\beta_A$ subunit and in the epidermis of the skin, activin A was localised in a patchy manner in the basal stratum germinativum (S.GE), to a limited degree in the stratum spinosum (S.Sp) and more heavily in the stratum granulosum (S.GR) just underneath the stratum lucidum (SL) when present (FIGS. 16 and 17). Follistatin is mildly expressed in the stratum germinativum, to a greater extent in the stratum spinosum but to a markedly decrease degree in the stratum granulosum. Where the stratum lucidum is present in thickened keratinised skin, follistatin was localised to the cells in this region (FIGS. 16 and 17). Note sections stained with haematoxylin and eosin (H&E) to assist with cell identification.

Figure 18:
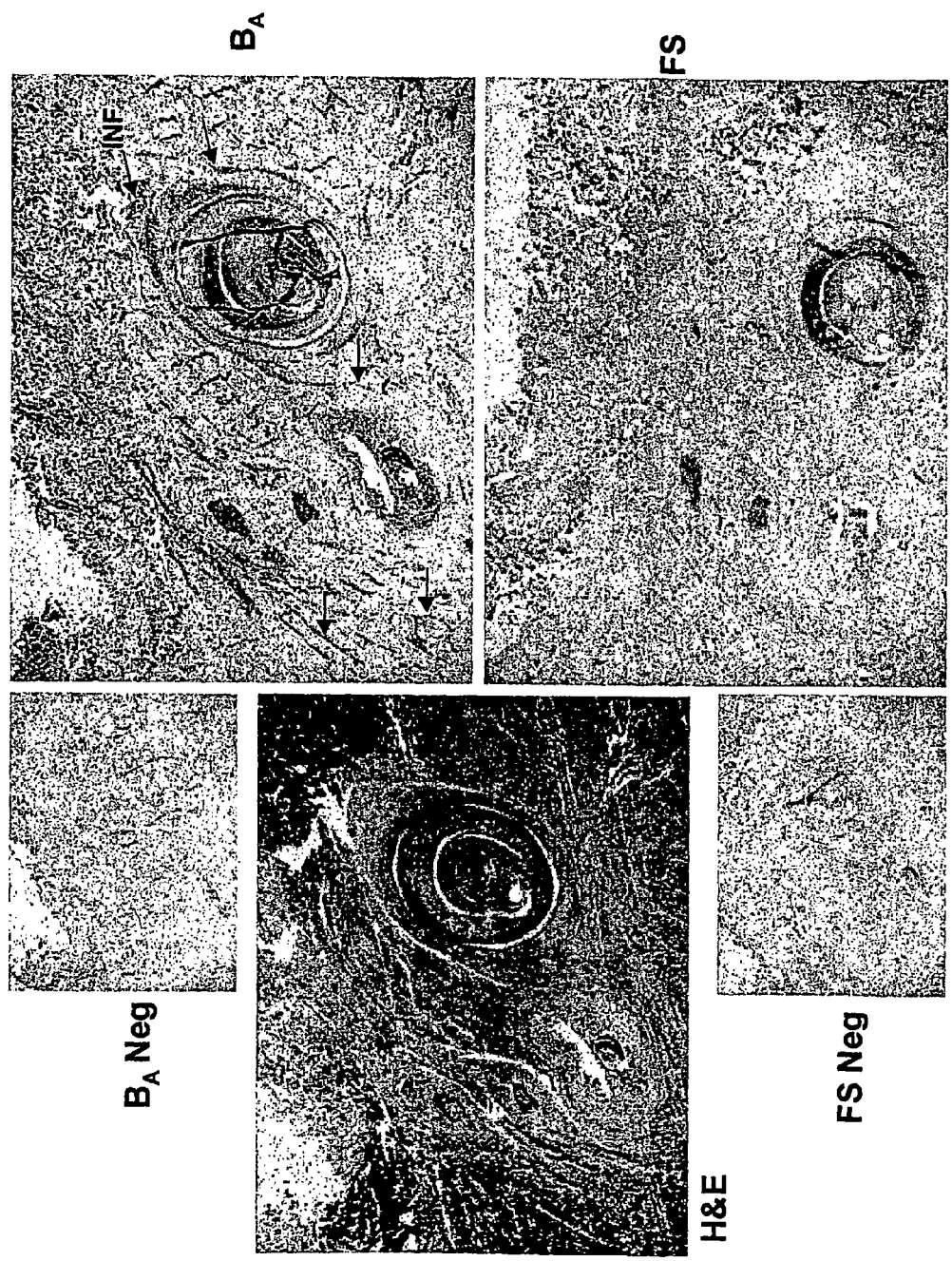
FIG. 18 is an image of a biopsy from area lacking epithelium and showing marked fibrosis with arrows indicating small blood vessels showing activin A localisation and an area of inflammatory cells (INF). Note follistatin shows markedly less intensity of stain.
Figure 19:
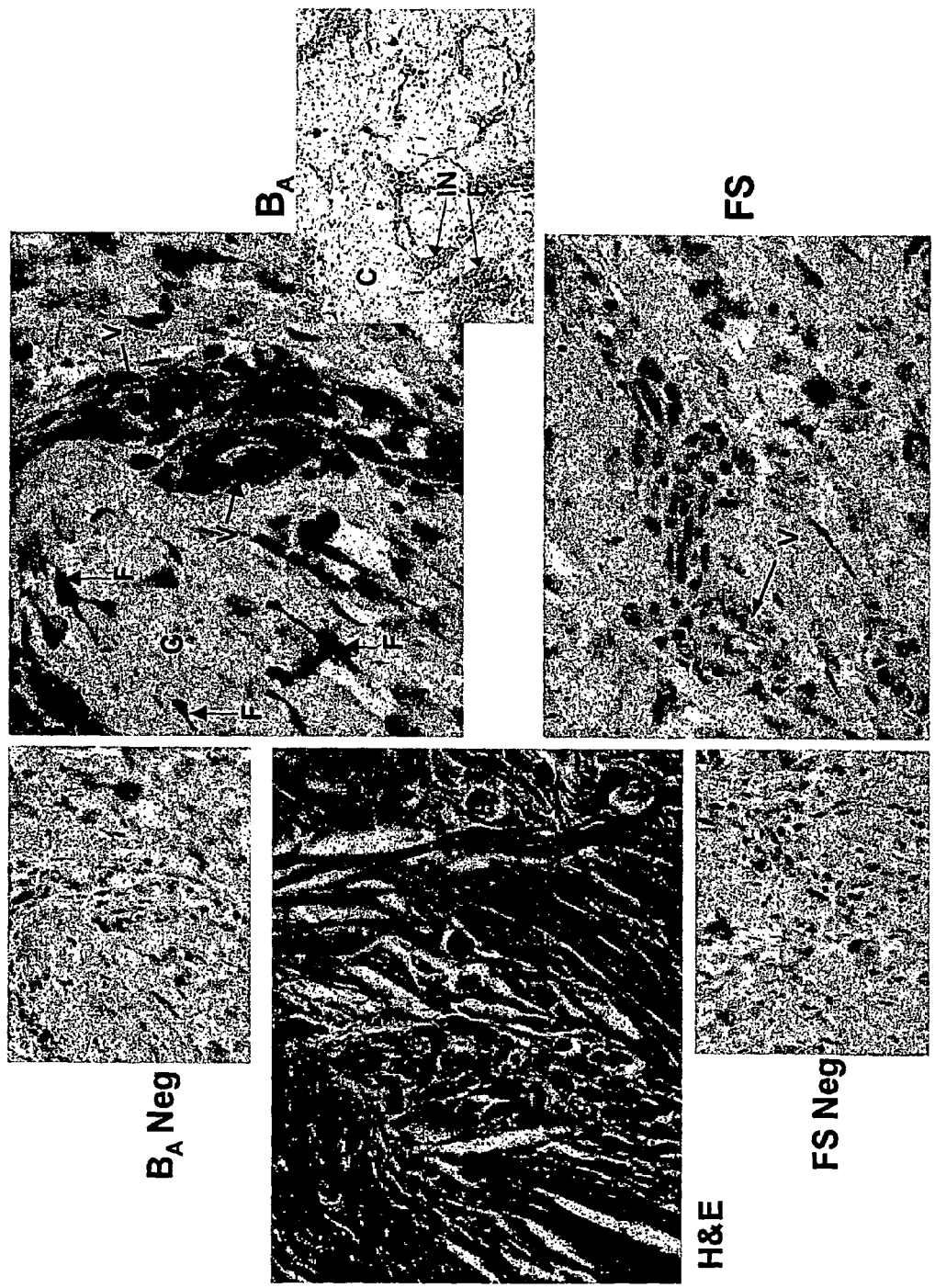
FIG. 19 is an image from a higher magnification showing dermal areas of fibrosis with amorphous appearing areas of collagen (C). Fibroblasts (F) showing activin A and markedly less follistatin intensity. Blood vessels also show localisation (V).
Figure 20:
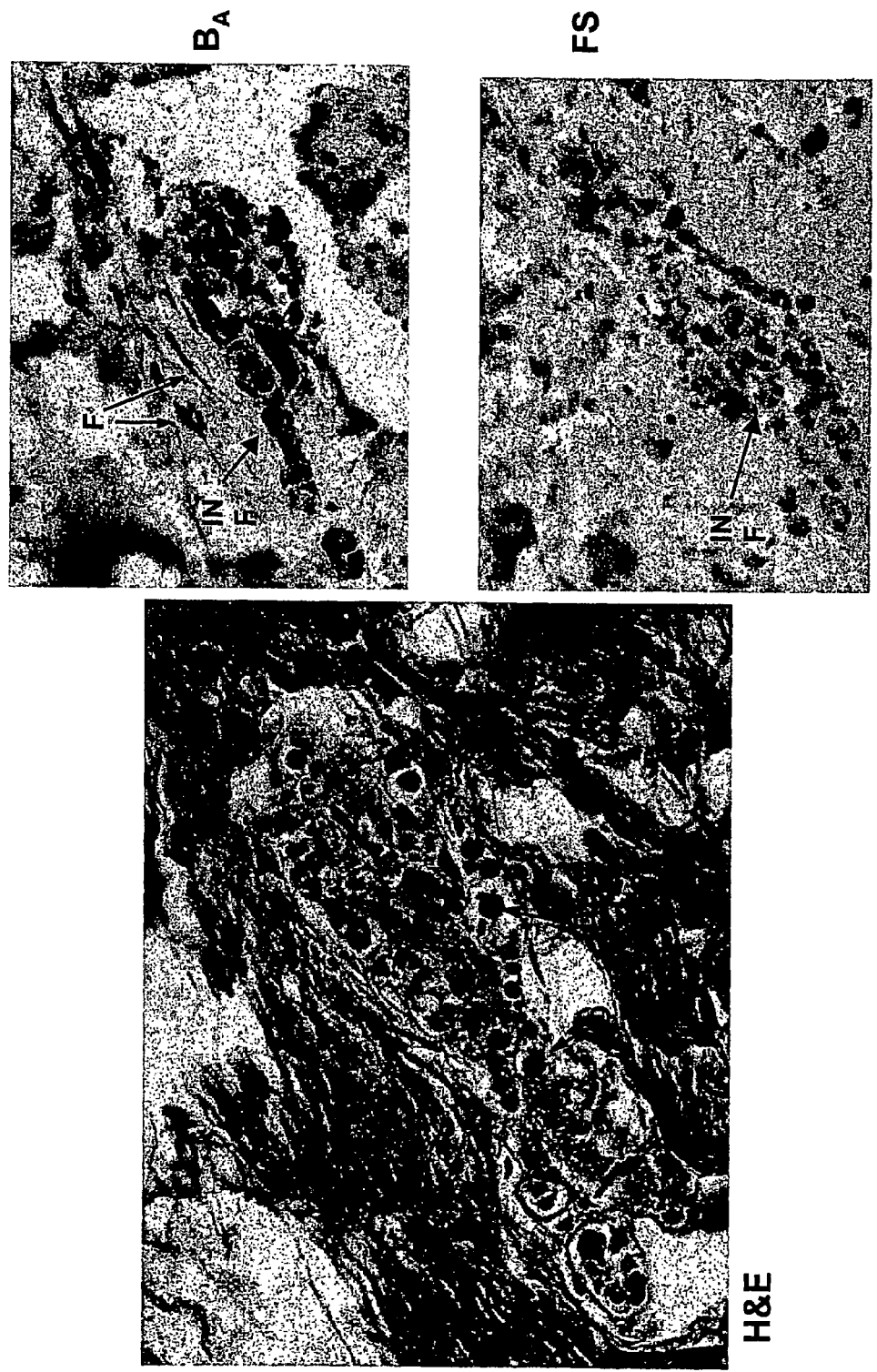
FIG. 20 is an image of an H&E stained section showing collection of dying (D) and inflammatory cells. Other areas show activin A and follistatin localisation in fibroblasts (F) and inflammatory cells (INF).

In the dermis, activin A is found in the endothelium of capillaries and small vessels (V), in macrophages and monocytes and polymorphonuclear leucocytes when present (FIGS. 18-20). Fibroblasts (F) contain activin A. Follistatin is present in endothelial cells and in low amount in macrophages (M) and fibroblasts (FIGS. 18-20). In biopsies from patients with poor healing, inflammation and fibrosis characterised by aggregations of collagen (C), there was up-regulation of activin A in fibroblasts, in macrophages and monocytes and in leucocytes (INF) (FIGS. 18-20). In some areas, there are collections of macrophages, monocytes, leucocytes and degenerating cells (D) and each shows significant localisation of activin A whereas that of follistatin is patchy and of lesser intensity (FIG. 18-20). The increased vascularity in these regions shows clear and increased localisation of activin A in endothelial cells (V) (see arrows FIG. 18) (FIGS. 18-20).

The increased localisation of active A in fibroblasts is likely to be responsible for the dermal fibrosis occurring after burns injury to skin given that others have found a correlation between the activin A up-regulation in lung tissue after bleomycin treatment and the lung fibrosis that results (Matsuse et al., 1995, *American Journal of Respiratory Cell and Molecular Biology* 13 17-24). Similar correlations were also found between activin A up-regulation and pulmonary fibrosis in humans (Matsuse et al., 1996, *American Journal of Pathology* 148 707-713) and Ohga et al. (Ohga et al., 1996, *Biochemical and Biophysical Research Communications* 228 391-396)

showed that activin A promotes the proliferation of lung fibroblasts and their differentiation to myofibroblasts which produce collagen.

Given that follistatin neutralises the actions of activin A and can attenuate the development of hepatic fibrosis, it can be used to prevent the development of fibrosis induced by the inflammatory reaction caused by burns. The elevated activin A and follistatin seen in some patients after burns indicates the involvement of activin A in this inflammatory process analogous to the changes induced by LPS in mice. The previous example showing that follistatin, given before the LPS challenge in mice, can alter the pattern of cytokines, provides evidence that blocking the biological actions of activin can alter the cytokine cascade. These data further indicate that blocking the biological actions of activin A induced by thermal injury by follistatin would block the actions of activin A that are a consequence of tissue injury.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Alexander C, Rietschel E T, 2001, Bacterial lipopolysaccharides and innate immunity. *J Endotoxin Res* 7:167-202

Benayoun, L., A. Druilhe, M. C. Dombret et al. 2003. Airway structural alterations selectively associated with severe asthma. *Am J Respir Crit Care Med* 167:1360-1368.

Bernard D J 2004 Both SMAD2 and SMAD3 mediate activin-stimulated expression of the follicle-stimulating hormone beta subunit in mouse gonadotrope cells. *Molecular Endocrinology* 18 606-623

Billestrup N, Gonzalez-Manchon C, Potter E & Vale W. Inhibition of somatotroph growth and growth hormone biosynthesis by activin in vitro. *Molecular Endocrinology* 1990 4 356-362.

Brown C W, Houston-Hawkins D E, Woodruff T K & Matzuk M M 2000 Insertion of Inhbb into the Inhba locus rescues the Inhba-null phenotype and reveals new activin functions. *Nature Genetics* 25 453-457

Bunin B A, et al. (1994) Proc. Natl. Acad. Sci. USA, 91:4708-4712

Corrigan A Z, Bilezikjian L M, Carroll R S, Bald L N, Schmelzer C H, Fendly B M, Mason A J, Chin W W, Schwall R H & Vale W 1991 Evidence for an autocrine role of activin B within rat anterior pituitary cultures. *Endocrinology* 128 1682-1684

Coyle, A. J., S. Tsuyuki, C. Bertrand, S. Huang, M. Aguet, S. S. Alkan, and G. P. Anderson. 1996. Mice lacking the IFN-gamma receptor have impaired ability to resolve a lung eosinophilic inflammatory response associated with a prolonged capacity of T cells to exhibit a Th2 cytokine profile. *J Immunol* 156:2680-2685.

De Bleser P J, Niki T, Xu G, Rogiers V & Geerts A 1997 Localization and cellular sources of activins in normal and fibrotic rat liver. *Hepatology* 26 905-912

Demura R, Suzuki T, Tajima S, Mitsuhashi S, Odagiri E, Demura H et al. Human plasma free activin and inhibin levels during the menstrual cycle. *Journal of Clinical Endocrinology and Metabolism* 1993 76 1080-1082.

Demura R, Suzuki T, Tajima S, Mitsuhashi S, Odagiri E, Eto Y et al. Competitive protein binding assay for activin A/EDF using follistatin determination of activin levels in human plasma. *Biochemical and Biophysical Research Communications* 1992 185 1148-1154.

de Winter J P, ten Dijke P, de Vries C J, van Achterberg T A, Sugino H, de Waele P et al. Follistatins neutralize activin bioactivity by inhibition of activin binding to its type II receptors. *Molecular and Cellular Endocrinology* 1996 116 105-114.

DeWitt S H, et al. (1993) Proc. Natl. Acad. Sci. USA, 90:6909-6913

Douillard and Hoffman, Basic Facts about Hybridomas, in *Compendium of Immunology Vol II*, ed. by Schwartz, 1981

Erämaa M, Hurme M, Stenman U H, Ritvos O (1992), Activin A/erythroid differentiation factor is induced during human monocyte activation. *J Exp Med* 176:1449-52

Fodor S P, Read J L, Pirrung M C, Stryer L, Lu A T, Solas D. (1991) *Science* 251(4995):767-73

Gilfillan C P & Robertson D M. Development and validation of a radioimmunoassay for follistatin in human serum. *Clinical Endocrinology* 1994 41 453-461.

Hardy, C. L., L. Kenins, A. C. Drew, J. M. Rolland, and R. E. O'Hehir. 2003. Characterization of a mouse model of allergy to a major occupational latex glove allergen Hev b 5. *Am J Respir Crit Care Med* 167:1393-1399.

Harrison C A, Gray P C, Fischer W H, Donaldson C, Choe S & Vale W 2004 An activin mutant with disrupted ALK4 binding blocks signaling via type II receptors. *Journal of Biological Chemistry* 279 28036-28044

Hashimoto O, Nakamura T, Shoji H, Shimasaki S. Hayashi Y & Sugino H. A novel role of follistatin, an activin-binding protein, in the inhibition of activin action in rat pituitary cells. Endocytotic degradation of activin and its acceleration by follistatin associated with cell-surface heparan sulfate. *Journal of Biological Chemistry* 1997 272 13835-13842.

Hübner G & Werner S. Serum growth factors and proinflammatory cytokines are potent inducers of activin expression in cultured fibroblasts and keratinocytes. *Experimental Cell Research* 1996 228 106-113.

Hübner G, Brauchle M, Gregor M & Werner S. Activin A: a novel player and inflammatory marker in inflammatory bowel disease? *Laboratory Investigation* 1997 77 311-318.

Hübner G, Hu Q, Smola H & Werner S. Strong induction of activin expression after injury suggests an important role of activin in wound repair. *Developmental Biology* 1996 173 490-498.

Jones R L, Salamonsen L A, Critchley H O D, Rogers P A W, Affandi B and Findlay J K, 2000, Inhibin and activin subunits are differentially expressed in endometrial cells and leukocytes during the menstrual cycle, in early pregnancy and in women using progestin-only contraception. *Molecular Human Reproduction* 6:1107-1117.

Keelan J A, Zhou R L & Mitchell N M. Activin A exerts both pro- and anti-inflammatory effects on human term gestational tissues. *Placenta* 2000 21 3843.

Khoury R H, Wang Q F, Crowley W F Jr, Hall J E, Schneyer A L, Toth T et al. Serum follistatin levels in women: evidence against an endocrine function of ovarian follistatin. *Journal of Clinical Endocrinology and Metabolism* 1995 80 1361-1368.

Kitaoka M, Kojima I & Ogata E. Activin-A: a modulator of multiple types of anterior pituitary cells. *Biochemical and Biophysical Research Communications* 1988 157 48-54.

Knight P G, Muttukrishna S, Groome N P (1996), Development and application of a two-site enzyme immunoassay for the determination of 'total' activin-A concentrations in serum and follicular fluid. *J Endocrinol* 148:267-79

Kobayashi T, Niimi S, Hashimoto O, and Hayakawa T, (2000) *Biol. Pharm. Bull.* 23(6):755-757

Kohler and Milstein, *Nature* 256: 495-499, 1975; *European Journal of Immunology* 6: 511-519, 1976

Kumar, R. K., C. Herbert, M. Yang et al. 2002. Role of interleukin-13 in eosinophil accumulation and airway remodelling in a mouse model of chronic asthma. *Clin Exp Allergy* 32:1104-1111.

Lee, C. G., R. J. Homer, Z. Zhu et al. 2001. Interleukin-13 induces tissue fibrosis by selectively stimulating and activating transforming growth factor beta(1). *J Exp Med* 194: 809-821.

Li, X., and J. W. Wilson. 1997. Increased vascularity of the bronchial mucosa in mild asthma. *Am J Respir Crit Care Med* 156:229-233.

Loria P., Petraglia F, Concari M, Bertolotti M, Martella P, Luisi S et al. Influence of age and sex on serum concentrations of total dimeric activin A. *European Journal of Endocrinology* 1998 139 487-492.

Maeshima K, Maeshima A, Hayashi Y, Kishi S & Kojima I 2004 Crucial role of activin A in tubulogenesis of endothelial cells induced by vascular endothelial growth factor. *Endocrinology* 145 3739-3745

Manthey C L, Perera P Y, Henricson B E, Hamilton T A, Qureshi N, Vogel S N (1994), Endotoxin-induced early gene expression in C3H/HeJ (Lpsd) macrophages. *J Immunol* 153:2653-63

Matsuse T, Fukuchi Y, Eto Y, Matsui H, Hosoi T, Oka T, Ohga E, Nagase T & Orimo H 1995 Expression of immunoreactive and bioactive activin A protein in adult murine lung after bleomycin treatment. *American Journal of Respiratory Cell and Molecular Biology* 13 17-24.

Matsuse T, Ikegami A, Ohga E, Hosoi T, Oka T, Kida K, Fukayama M, Inoue S, Nagase T, Ouchi Y et al. 1996 Expression of immunoreactive activin A protein in remodeling lesions associated with interstitial pulmonary fibrosis. *American Journal of Pathology* 148 707-713

Matzuk M M, Kumar T R, Vassalli A, Bickenbach J R, Roop D R, Jaenisch R & Bradley A 1995 Functional analysis of activins during mammalian development. *Nature* 374 354-356

McFarlane J R, Foulds L M, Pisciotta A, Robertson D M & de Kretser D M. Measurement of activin in biological fluids by radioimmunoassay, utilizing dissociating agents to remove the interference of follistatin. *European Journal of Endocrinology* 1996 134 481-489.

Meunier H, Rivier C, Evans R M & Vale W. Gonadal and extragonadal expression of inhibin α, βA and βB subunits in various tissues predicts diverse functions. *PNAS* 1988 85 247-251.

Michel U, Albiston A & Findlay J K. Rat follistatin: gonadal and extragonadal expression and evidence for alternative splicing. *Biochemical and Biophysical Research Communications* 1990 173 401-407.

Michel U, Esselmann J & Nieschlag E. Expression of follistatin messenger ribonucleic acid in Sertoli cell-enriched cultures: regulation by epidermal growth factor and protein kinase C-dependent pathway but not by follicle-stimulating hormone and protein kinase A-dependent pathway. *Acta Endocrinologica* 1993 129 525-531.

Michel U, Schneider O, Kirchhof C, Meisel S, Smirnov A, Wiltfang J et al. Production of follistatin in porcine endothelial cells: differential regulation by bacterial compounds and the synthetic glucocorticoid RU 28362. *Endocrinology* 1996 137 4925-4934.

Michel U, Ebert S, Phillips D & Nau R 2003 Serum concentrations of activin and follistatin are elevated and run in parallel in patients with septicemia. *European Journal of Endocrinology* 148 559-564

Mohan A, Asselin J, Sargent I L, Groome N P & Muttukrishna S. Effect of cytokines and growth factors on the secretion of inhibin A, activin A and follistatin by term placental villous trophoblasts in culture. *European Journal of Endocrinology* 2001 145 505-511.

Nakamura T, Takio K, Eto Y, Shibai H, Titani K & Sugino H 1990 Activin-binding protein from rat ovary is follistatin. *Science* 247 836-838

Nakamura T, Asashima M, Eto Y, Takio K, Uchiyama H, Moriya N, Ariizumi T, Yashiro T, Sugino K, Titani K et al. 1992 Isolation and characterization of native activin B. *Journal of Biological Chemistry* 267 16385-16389

O'Connor A E, McFarlane J R, Hayward S, Yohkaichiya T, Groome N P, de Kretser D M (1999), Serum activin A and follistatin concentrations during human pregnancy: a cross-sectional and longitudinal study. *Hum Reprod.* 14:827-832

Orsida, B. E., X. Li, B. Hickey, F. Thien, J. W. Wilson, and E. H. Walters. 1999. Vascularity in asthmatic airway: relation to inhaled steroid dose. *Thorax* 54:289-295.

Petraglia F, Garg S, Florio P, Sadick M, Gallinelli A, Wong W-L, Krummen L, Comitini G, Mather J & Woodruff T K 1993 Activin A and activin B measured in maternal serum, cord blood serum and amniotic fluid during human pregnancy. *Endocrine Journal* 1 323-327

Phillips D J, de Kretser D M, Pfeffer A, Chie W N & Moore L G. Follistatin has a biphasic response but follicle-stimulating hormone is unchanged during an inflammatory episode in growing lambs. *Journal of Endocrinology* 1998 156 77-82.

Phillips and deKretser, 1998, *Frontiers in Neuroendocrinology* 19:287-322

Phillips D J. New developments in the biology of inhibins, activins and follistatins. *Trends in Endocrinology and Metabolism* 2001 12 94-96.

Phillips, D. J. 2000. Regulation of activin's access to the cell: why is mother nature such a control freak? *Bioessays* 22:689-696.

Poulaki V, Mitsiades N, Kruse F E, Radetzky S, Iliaki E, Kirschof B & Joussen A M 2004 Activin A in the regulation of corneal vascularization and vascular endothelial growth factor expression. *American Journal of Pathology* 164 1293-1302

Robinson G W & Hennighausen L 1997 Inhibins and activins regulate mammary epithelial cell differentiation through mesenchymal-epithelial interactions. *Development* 124 2701-2708

Rosendahl, A., D. Checchin, T. E. Fehniger et al. 2001. Activation of the TGF-beta/activin-Smad2 pathway during allergic airway inflammation. *Am J Respir Cell Mol Biol* 25:60-68.

Russell C E, Hedger M P, Brauman J N, de Kretser D M, Phillips D J (1999), Activin A regulates growth and acute phase proteins in the human liver cell line, HepG2. *Mol Cell Endocrinol* 148:129-36

Sakai R, Shiozaki M, Tabuchi M & Eto Y. The measurement of activin/EDF in mouse serum: evidence for extragonadal production. *Biochemical and Biophysical Research Communications* 1992 188 921-926.

Sakamoto Y, Shintani Y, Harada K, Abe M, Shitsukawa K & Saito S. Determination of free follistatin levels in sera of normal subjects and patients with various diseases. *European Journal of Endocrinology* 1996 135 345-351.

Schneider O, Nau R & Michel U. Comparative analysis of follistatin-, activin beta A- and activin beta B-mRNA steady-state levels in diverse porcine tissues by multiplex S1 nuclease analysis. *European Journal of Endocrinology* 2000 142 537-544.

Shao L, Frigon N L, Jr, Sehy D W, Yu A L, Lofgren J, Schwall R, Yu J (1992), Regulation of production of activin A in human marrow stromal cells and monocytes. *Exp Hematol* 20:1235-42

Shao L E, Frigon N L, Jr, Yu A, Palyash J, Yu J (1998), Contrasting effects of inflammatory cytokines and glucocorticoids on the production of activin A in human marrow stromal cells and their implications. *Cytokine* 10:227-35

Stein and Cohen, 1988 (Cancer Res 48:2659-68)

Takabe K, Wang L L, Leal A M O, MacConell L A, Wiater E, Tomiya T, Ohno A, Verma I M & Vale W 2003 Adenovirus-mediated overexpression of follistatin enlarges intact liver of adult rats. *Hepatology* 38 1107-1115

Thomsen G, Woolf T, Whitman M, Sokol S. Vaughan J, Vale W & Melton D A 1990 Activins are expressed early in *Xenopus* embryogenesis and can induce axial mesoderm and anterior structures. *Cell* 63 485-493

Tilbrook A J, de Kretser D M, Dunshea F R, Klein R, Robertson D M, Clarke I J et al. The testis is not the major source of circulating follistatin in the ram. *Journal of Endocrinology* 1996 149 55-63.

Tsuchida K, Nakatani M, Yamakawa N, Hashimoto O, Hasegawa Y & Sugino H 2004 Activin isoforms signal through type I receptor serine/threonine kinase ALK7. *Molecular and Cellular Endocrinology* 220 59-65

Ulevitch R J, Tobias P S, 1999, Recognition of gram-negative bacteria and endotoxin by the innate immune system. *Curr Opin Immunol* 11:19-22

Vale W, Rivier J, Vaughan J, McClintock R, Corrigan A, Woo W et al. (1986) Purification and characterization of an FSH releasing protein from porcine ovarian follicular fluid. *Nature* 321 776-779.

Vale et al. (1990) In peptide growth factors and their receptors: Handbook of Experimental Physiology, Vol. 95, Eds. Sporn & Roberts, Springer-Verlag, Berlin pp 211-248]

van der Krol et al., 1988 (Biotechniques 6:958-976)

Van Baalen B, Odding E, Maas A I R, Ribbers G M, Bergen M P & Stam H J 2003 Traumatic brain injury: classification of initial severity and determination of functional outcome. *Disability and Rehabilitation* 25 9-18

Van Dijk W & Mackiewicz A 1995 Interleukin-6-type cytokine-induced changes in acute phase protein glycosylation. *Annals of the New York Academy of Science* 762 319-330

Vassalli A, Matzuk M M, Gardner H A R, Lee K-F & Jaenisch R 1994 Activin/inhibin βB subunit gene disruption leads to defects in eyelid development and female reproduction. *Genes and Development* 8 414-427

Vihko K K, Bläuer M, Kujansuu E, Vilska S, Albäck T, Tuimala R, Tuohimaa P & Punnonen R 1998 Activin B: detection by an immunoenzymometric assay in human serum during ovarian stimulation and late pregnancy. *Human Reproduction* 13 841-846.

Vihko K K, Bläuer M, Puistola U & Tuohimaa P 2003 Activin B in patients with granulosa cell tumors: serum levels in comparison to inhibin. *Acta Obstetricia et Gynecologica Scandinavica* 80 570-574

Wakatsuki M, Shintani Y, Abe M, Liu Z H, Shitsukawa K & Saito S. Immunoradiometric assay for follistatin: serum immunoreactive follistatin levels in normal adults and pregnant women. *Journal of Clinical Endocrinology and Metabolism* 1996 81 630-634.

Wilson, J. W., and X. Li. 1997. The measurement of reticular basement membrane and submucosal collagen in the asthmatic airway. *Clin Exp Allergy* 27:363-371.

Woodruff T K, Sluss P, Wang E, Janssen I & Mersol-Barg M S 1997 Activin A and follistatin are dynamically regulated during human pregnancy. *Journal of Endocrinology* 152 167-174.

Xu J, McKeehan K, Matsuzaki K & McKeehan W L 1995 Inhibin antagonizes inhibition of liver cell growth by activin by a dominant-negative mechanism. *Journal of Biological Chemistry* 270 6308-6313

Yu J, Shao L E, Frigon N L Jr, Lofgren J & Schwall R. Induced expression of the new cytokine, activin A, in human monocytes: inhibition by glucocorticoids and retinoic acid. *Immunology* 1996 88 368-374.

The invention claimed is:

1. A method of treating cystic fibrosis in a mammal in need thereof, said method comprising administering follistatin to said mammal.

2. The method of claim 1, wherein the follistatin is administered as follistatin 315.

3. The method of claim 1, wherein the follistatin is administered as follistatin 288.

4. The method of claim 1, wherein the follistatin is administered by a route selected from the group consisting of injection, oral administration, oral inhalation, or a nebulizer.

5. The method of claim 1, wherein the mammal is human.

6. The method according to claim 1, wherein the method treats localized inflammatory responses associated with the cystic fibrosis.

7. The method according to claim 1, wherein the method treats airway inflammation associated with the cystic fibrosis.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
tactggcatc ttcaccacca                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
ggctaacaga accaggacca                                              20
```

```
<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gacacgcata gccagactca                                                   20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cttatgtatt ccggccatcc                                                   20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
gtgagcttcc cattcagctc                                                   20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
cttcttccca tctccatcca                                                   20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
acttgccctc tccaagaaca                                                   20

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
cctagtgtgg gctaccagga                                                   20
```